(12) United States Patent
Buchsbaum et al.

(10) Patent No.: US 6,552,005 B1
(45) Date of Patent: Apr. 22, 2003

(54) MOLECULAR CHEMOTHERAPY ENHANCEMENT OF RADIOTHERAPY

(75) Inventors: Donald J. Buchsbaum, South Birmingham, AL (US); C. Ryan Miller, Homewood, AL (US); G. Yancey Gillespie, Birmingham, AL (US); Robert J. Garver, Jr., Hoover, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/706,190

(22) Filed: Nov. 3, 2000

Related U.S. Application Data

(63) Continuation-in-part of application No. 09/408,055, filed on Sep. 29, 1999.
(60) Provisional application No. 60/102,391, filed on Sep. 29, 1998.

(51) Int. Cl.$^7$ .............................. A61R 48/00; C12N 5/00
(52) U.S. Cl. ....................... 514/44; 424/93.2; 435/69.1; 435/455; 435/320.1
(58) Field of Search .................. 514/274, 44; 424/93.2; 435/455, 320.1, 69.1

(56) References Cited

U.S. PATENT DOCUMENTS

| | | | | |
|---|---|---|---|---|
| 5,641,755 A | * | 6/1997 | Weichselbaum et al. | 424/9.2 |
| 6,074,640 A | * | 6/2000 | Curiel et al. | 424/130.1 |
| 6,096,303 A | * | 8/2000 | Fick | 424/93.2 |
| 6,100,243 A | * | 8/2000 | Frisch | 424/93.21 |
| 6,197,293 B1 | * | 3/2001 | Henderson et al. | 424/93.2 |
| 6,207,648 B1 | * | 3/2001 | Waxman et al. | 435/320.1 |
| 6,217,860 B1 | * | 4/2001 | Woo et al. | 424/93.2 |
| 2002/0055482 A1 | * | 5/2002 | Huber et al. | 514/44 |

OTHER PUBLICATIONS

Pederson et al, Cancer Research, vol. 57(19), oo. 4325–4332, 1997.*

* cited by examiner

*Primary Examiner*—James H. Reamer
(74) *Attorney, Agent, or Firm*—Benjamin Aaron Adler

(57) ABSTRACT

The present invention provides a new approach for cancer treatment by utilizing gene therapy combined with radiation therapy to enhance cytotoxicity in malignant cells. Specifically, the present invention demonstrates that molecular chemotherapy with the cytosine deaminase gene and 5-fluorocytosine is an effective radiosensitizing strategy which may lead to substantial improvement in tumor control, with less normal tissue toxicity than conventional systemic administration of 5-fluorouracil, that would translate into improved cure rates and better survival. A noninvasive method is described for continuous in vivo monitoring of 5-fluorouracil production via magnetic resonance spectroscopy. An adenovirus encoding cytosine deaminase gene which selectively replicates in tumor cells with a defective p53 pathway was constructed. Also provided is an adenovirus which encodes a fusion protein of cytosine deaminase and uracil phosphoribosyltransferase.

14 Claims, 25 Drawing Sheets

10 cfu AdCMVLacZ +
Fab-FGF2

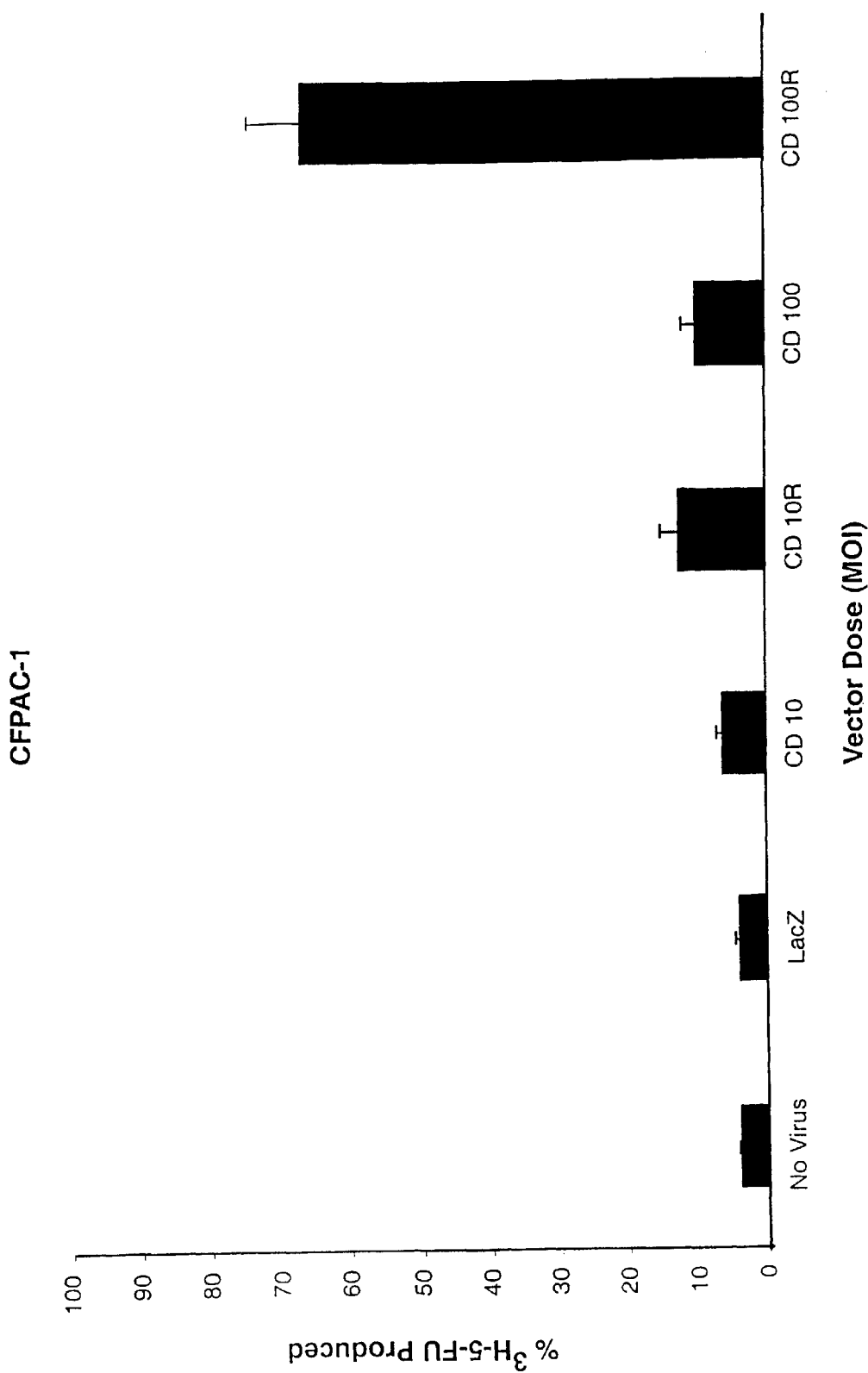

MOLECULAR CHEMOTHERAPY ENHANCEMENT OF RADIOTHERAPY

CROSS-REFERENCE TO RELATED APPLICATION

This application is a continuation-in-part U.S. patent application Ser. No. 09/408,055, filed Sep. 29, 1999 which claims benefit of provisional patent application U.S. Ser. No. 60/102,391, filed Sep. 29, 1998, now abandoned.

FEDERAL FUNDING LEGEND

This invention was created in part using funds from the federal government. The U.S. government, therefore, has certain rights in this invention.

BACKGROUND OF THE INVENTION

1. Field of the Invention

The present invention relates generally to the fields of molecular biology, radiation oncology and cancer therapy. More specifically, the present invention relates to the finding that a combination of molecular chemotherapy and radiation therapy enhances therapeutic effects against cancer.

2. Description of the Related Art

Clinical applications of cancer gene therapy have had limited success due to a variety of factors, including ineffective therapeutic gene delivery in situ. The physiologic milieu of the target tumor may have deleterious effects on the delivery of therapeutic genes. This limitation may be disease specific, and variable depending on the specific tumor type and tumor location. Most clinical gene therapy trials thus far have utilized compartmental models of malignant disease (1, 2). In this regard, thoracic malignancies and intra-abdominal carcinomatosis represent common body compartmentalized diseases that have been explored in a n experimental therapeutic context. Attempts to address the issue of achieving viral vector delivery to cancer cells in the face of a physiologic infection medium of pleural fluid or abdominal ascites have been examined (3, 4). Yang et al. demonstrated retroviral transduction of pancreatic cancer cells in the presence of human ascites, similar to the results obtained in culture medium (3). Batra et al. reported significant inhibition of retroviral transduction of mesothelioma cells in the presence of malignant pleural fluid, specifically the chondroitin sulfate proteoglycan fraction (4).

Radiotherapy combined with the radiosensitizing chemotherapeutic drug 5-fluorouracil (5-FU) has been studied as a therapeutic modality in many human tumor types (5). Systemic toxicity limits the amount of 5-FU that can be administered for many clinical anti-cancer applications (6, 7). Radiation therapy and gene therapy have the potential to be combined to enhance effectiveness of cancer therapy without enhancing dose limiting toxicity. To this end, reports have investigated this interaction (8). These include: TNFα under the control of a radiation inducible promoter (9, 10), conversion of prodrugs to toxic metabolites that are also radiosensitizers (11–15), p53 mediated radiosensitization (16, 17) and the genetic induction of membrane receptors that can be targeted with radiolabeled peptides (18–21).

With respect to enzymatic conversion of nontoxic prodrugs into radiation sensitizing agents, the genes for bacterial and yeast cytosine deaminase (CD) have been cloned and studied (22, 23, 40). Cytosine deaminase converts a nontoxic prodrug 5-fluorocytosine (5-FC) into 5-FU. The cytosine deaminase gene has been used in gene therapy strategies to mediate intracellular conversion of 5-FC to 5-FU, and has been shown to be effective in animal tumor models of human colon carcinoma (24). Human colon cancer cells that have been stably transduced to express the cytosine deaminase gene have been shown to be radiosensitized by the addition of 5-FC in vitro and in vivo (13). Adenoviral vectors have been used to achieve efficient gene delivery in a variety of tissues in vitro and in vivo. Adenoviral vectors encoding the cytosine deaminase gene have been described (25, 26).

Presently available assays for determining intratumoral 5-FU concentration are problematic. They require the removal of a tumor, the homogenization of that tumor and the collection of the cellular lysate in order to directly measure 5-FU concentration, usually by high-pressure liquid chromatography. No noninvasive method of detection existed, which could allow for continuous in vivo monitoring of 5-FU production.

In the context of multiple administrations of adenoviral vectors, the host immunologic response, with generation of neutralizing anti-adenovirus antibodies and cytotoxic T cells, is thought to limit the potential effectiveness of secondary administration of adenoviral vectors. A means to overcome this problem may be to improve the effectiveness of infection of the initial viral challenge, i.e., to enhance the transduction efficiency of the adenoviral vector for the target cells at the initial adenoviral administration. This goal may be achieved by utilizing a ligand to a cellular receptor overexpressed in the target carcinoma cells to redirect adenovirus vector binding.

Primary central nervous system (CNS) tumors, arising in both the brain and spinal cord, are the leading cause of cancer-related deaths in children less than 15 years of age (42–44). They are the most common solid neoplasia in children with an estimated incidence of 3.77 newly diagnosed pediatric patients per 100,000 children at risk each year in the US (45). Despite aggressive treatment with radiation and/or chemotherapy, children with intrinsic brainstem gliomas and high-grade astrocytomas rarely survive more than a few years from diagnosis (46–49). The long-term sequelae of radiation are significant, especially in very young children, militating against its use as standard therapy in children less than 36 months old (50–52). In this context, gene therapy offers a promising approach for pediatric brain tumors.

The main factor currently limiting the clinical potential of gene therapy is the poor level of in situ tumor cell transduction achievable by existing gene transfer vectors (53). Of these, adenovirus (Ad) is particularly attractive due to its well-characterized mechanism of cellular entry, and its propensity to efficiently infect a wide variety of cell types within the CNS (54–56). This is presumably due to their expression of the cellular receptors necessary for efficient Ad entry, the coxsackie-adenovirus receptor (CAR) and av integrins (57, 58). Ad vectors have shown utility in several animal models of glioma (59, 60) and are currently being investigated in at least three separate clinical trials in the US in adult patients with malignant glioblastomas. Yet as all three employ direct intratumoral or intracavitary injection, expression of Ad receptors on these tumors will likely determine the overall success of these and future Ad cancer gene therapy trials. Two of these trials are investigating replication-defective Ad as a vector for enzyme/prodrug therapy using herpes simplex virus thymidine kinase/gancyclovir (HSV-tk/GCV, 61). While HSV-tk/GCV enzyme/prodrug therapy is promising for malignant gliomas, several alternatives have been described (reviewed in 62).

The third trial involves a replication-competent Ad lacking an exogenous transgene (ONYX-015) (76) and is being conducted in adult patients. ONYX-015 harbors an E1B-55K gene deletion that permits the selective replication in and lysis of cells with mutations in the gene encoding $p^{53}$ (77). Replication-competent viruses such as Ad have distinct advantages over non-replicative viruses in cancer gene therapy (reviewed in 78, 79). First, Ad replication in tumor cells results in cell lysis (lytic infection) and hence tumor destruction (viral oncolysis). Second, lateral spread of progeny Ad virions within the productively infected tumor mass dramatically increases exogenous transgene expression compared with replication-defective vectors (80).

The prior art is deficient in the lack of effective means of treating of human cancers by chemotherapy combined with radiation therapy to produce enhanced therapeutic effects against cancer and reduced normal tissue toxicity. In addition, the prior art is deficient in the lack of effective means of redirecting adenovirus vector binding via a cellular receptor to improve the effectiveness of gene therapy. Furthermore, the prior art is deficient in the lack of a noninvasive method for continuously monitoring therapeutic transgene expression in tumors therefore improving the gene therapy. The present invention fulfills this longstanding need and desire in the art.

SUMMARY OF THE INVENTION

The present invention is directed to a method of transfecting established tumors in vivo with an adenovirus encoding the cytosine deaminase gene, administration of systemic 5-FC, and radiation therapy, (e.g., external beam or brachytherapy) of the tumor. This method results in tumor regression and prolonged tumor growth inhibition compared to control treatments with molecular chemotherapy or radiation therapy alone. Also disclosed is an adenoviral-conjugate mechanism to circumvent current limitations of cancer gene therapy to solid gastrointestinal malignancies.

Specifically, the present invention utilizes an adenoviral vector under the control of a cytomegalovirus promoter (AdCMVCD) encoding cytosine deaminase in combination with 5-FC and single fraction radiotherapy to demonstrate enhanced cytotoxicity to WiDr human colon carcinoma cells in vitro. The present invention also demonstrates such gene therapy/prodrug treatment strategy employing a fractionated radiation dosing schema in animal models of WiDr human colon carcinoma and SK-ChA-1 human cholangiocarcinoma. A prolonged WiDr tumor regrowth delay was obtained with AdCMVCD infection in combination with systemic delivery of 5-FC and fractionated external beam radiation therapy compared to control animals treated without radiation, without 5-FC, or without AdCMVCD. The present invention further discloses redirection of adenovirus vector (AdCMVCD) binding via a ligand to a cellular receptor, e.g., the basic fibroblast growth factor (FGF2) receptor, to improve the effectiveness of gene therapy in combination with 5-FC treatment and radiation therapy.

Clinical applications for cancer gene therapy are limited by the inability to genetically modify a majority of tumor cells to achieve a therapeutic effect. In this regard, the enzyme/prodrug strategy consisting of cytosine deaminase/5-fluorocytosine (CD/5-FC) relies on diffusion of the cytotoxic enzymatic product 5-FU to kill non-transduced tumor cells. Methods to increase solid tumor transduction in situ may augment therapeutic gene expression and response to therapy. To this end, gene delivery was improved via vector binding to molecules expressed on the cells of tumors. Fibroblast growth factor (FGF) receptors are overexpressed in a majority of pancreatic carcinomas, but poorly characterized in cholangiocarcinoma. Targeted adenovirus via basic fibroblast growth factor (FGF2) to the fibroblast growth factor receptor was used as a vehicle for the delivery of cytosine deaminase to hepatobiliary tumor cells for combination molecular chemotherapy and radiation therapy studies.

FGF2 redirected adenoviral delivery of firefly luciferase gene (AdCMVLuc) expression was evaluated in vitro. Transduction efficiencies using adenoviral delivered *E. coli* β-galactosidase gene (AdCMVLacZ) expression also were determined. The methodology to redirect adenoviral gene delivery employed the Fab fragment of a neutralizing anti-adenoviral knob monoclonal antibody which ablates native adenoviral tropism, conjugated to FGF2 ligand which provides for FGF receptor binding. An adenoviral vector encoding the cytosine deaminase gene (AdCMVCD), in combination with 5-FC and the Fab-FGF2 conjugate, was used to evaluate differential cytosine deaminase protein expression by Western blotting of transfected cell lines and enzymatic activity by increased conversion of $^3$H-5-FC into $^3$H-5-FU. Proliferation assays were performed to correlate differential production of 5-FU with increased cytotoxicity in selected pancreatic and cholangiocarcinoma cell lines. In vivo studies utilizing AdCMVCD, the Fab'-FGF2 conjugate, 5-FC administration, and a single 5 Gy dose of external beam radiation to the tumor in nude mice were performed to evaluate the anti-tumor efficacy of AdCMVCD+Fab'-FGF2, compared to AdCMVCD alone, in established subcutaneous BXPC-3 pancreatic tumors.

In target cells, FGF2 retargeted AdCMVLuc resulted in enhanced (10–100-fold) levels of firefly luciferase expression relative to AdCMVLuc infection alone. X-gal staining for β-galactosidase expression revealed an enhanced transduction frequency mediated by Fab-FGF2 redirected AdCMVLacZ compared to AdCMVLacZ infection alone. Fab-FGF2 redirection of AdCMVCD resulted in increased cellular expression of cytosine deaminase and production of 5-FU, and enhanced cellular cytotoxicity at low viral multiplicities of infection, compared to the levels obtained with AdCMVCD alone. In BXPC-3 tumor-bearing animals treated with AdCMVCD+Fab'-FGF2, 5-FC, and radiotherapy, the time to tumor size doubling was extended compared to AdCMVCD, 5-FC, and radiotherapy alone.

These results indicate that native adenoviral tropism can be redirected using ligands to cell surface receptors. In addition, transduction efficiencies and expression of genes introduced via this heterologous pathway are significantly enhanced compared to native adenovirus transduction alone. These findings suggest improved gene expression may be achieved via this adenoviral-conjugate mechanism to circumvent current limitations of cancer gene therapy to solid gastrointestinal malignancies.

The present invention is further directed to a noninvasive method for monitoring the continuous conversion of 5-fluorocytosine to 5-fluorouracil via magnetic resonance spectroscopy (MRS). Magnetic resonance spectroscopy allows for monitoring this prodrug activation therapy through the following: the identification of tumor and normal tissue sites of production or accumulation of 5-fluorouracil, the discrimination of both 5-fluorocytosine clearance/5-fluorouracil production, the determination of the residence time of 5-fluorouracil, the production of metabolites of the active drug, along with the determination of the elimination kinetics of 5-fluorouracil from tumor and normal organs. The information that magnetic resonance spectroscopy can provide about the pharmacokinetics of these agents can help develop procedures to maximize the effectiveness of this therapy with the potential to maximize tumor regression.

In one embodiment of the present invention, there is provided a method of treating an individual having a solid tumor, comprising the steps of treating the individual with an adenovirus encoding a cytosine deaminase gene; administering 5-fluorocytosine to the individual; and treating the individual with radiation therapy.

In another embodiment of the present invention, there is provided a method of treating an individual having a cancer, comprising the steps of combining a ligand that binds to a tumor cellular receptor and an adenoviral vector encoding a cytosine deaminase gene to form a complex; treating the individual with the complex; administering 5-fluorocytosine to the individual; and treating the individual with external beam irradiation.

In still another embodiment of the present invention, there is provided a method of monitoring continuous conversion of 5-fluorocytosine to 5-fluorouracil in a tumor, wherein the tumor is treated with multiple doses of 5-fluorocytosine and multiple doses of adenovirus encoding a cytosine deaminase gene, comprising the steps of placing the treated tumor in a magnet; and evaluating the presence of 5-fluorocytosine and 5-fluorouracil by magnetic resonance spectroscopy over a course of time, wherein less amount of 5-fluorocytosine and more amount of 5-fluorouracil indicates increased conversion of 5-fluorocytosine to 5-fluorouracil. Preferably, the tumor is further treated with radiation.

In still yet another embodiment of the present invention, there is provided a method of monitoring continuous conversion of 5-fluorocytosine to 5-fluorouracil in a tumor, wherein the tumor is treated with multiple doses of 5-fluorocytosine and multiple doses of cytosine deaminase gene encoding adenovirus targeted by a ligand to a tumor cellular receptor, comprising the steps of placing the treated tumor in a magnet; and evaluating the presence of 5-fluorocytosine and 5-fluorouracil by magnetic resonance spectroscopy over a course of time, wherein less amount of 5-fluorocytosine and more amount of 5-fluorouracil indicates increased conversion of 5-fluorocytosine to 5-fluorouracil. Preferably, the tumor is further treated with radiation.

The instant invention also provides an adenovirus which selectively replicates in tumor cells and encodes a cytosine deaminase gene. Preferably, the adenovirus has a complete E1A gene but lacks an E1B gene and selectively replicates in cells with a defective p53 pathway. AdE1ACD is a representative example of such an adenovirus.

The instant invention is further directed to a method of treating an individual having a solid tumor with a selectively replicating adenovirus encoding cytosine deaminase comprising the steps of infecting the individual with the adenovirus and administering 5-fluorocytosine followed by radiation therapy.

A further embodiment of the instant invention is directed to an adenovirus which coexpresses cytosine deaminase and uracil phosphoribosyltransferase preferably as a fusion protein as is the case with AdCDUPRT.

The present invention also includes a method of treating an individual having a solid tumor by administering an adenovirus coexpressing cytosine deaminase and uracil phosphoribosyltransferase and administering 5-fluorocytosine followed by radiation therapy.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 8 shows that Fab-FGF2-retargeted AdCMVLacZ resulted in enhanced transduction efficiency of pancreatic and cholangiocarcinoma cells. BXPC-3 pancreatic carcinoma cells and SK-ChA-1 cholangiocarcinoma cells were infected with AdCMVLacZ or AdCMVLacZ+Fab-FGF2 at a MOI of 10. Forty-eight hours later, X-gal staining was performed.

FIG. 9 shows retargeted transfection (R) with AdCMVCD+Fab-FGF2 in five cell lines was evaluated, by Western, with each cell line on a separate gel. On each gel, six lanes were run at the MOI listed. Cells were transduced with either AdCMVCD or AdCMVCD-Fab-FGF2 or mock transfection. Cell extracts were prepared and equal protein loaded per well.

DETAILED DESCRIPTION OF THE INVENTION

Figure 1:
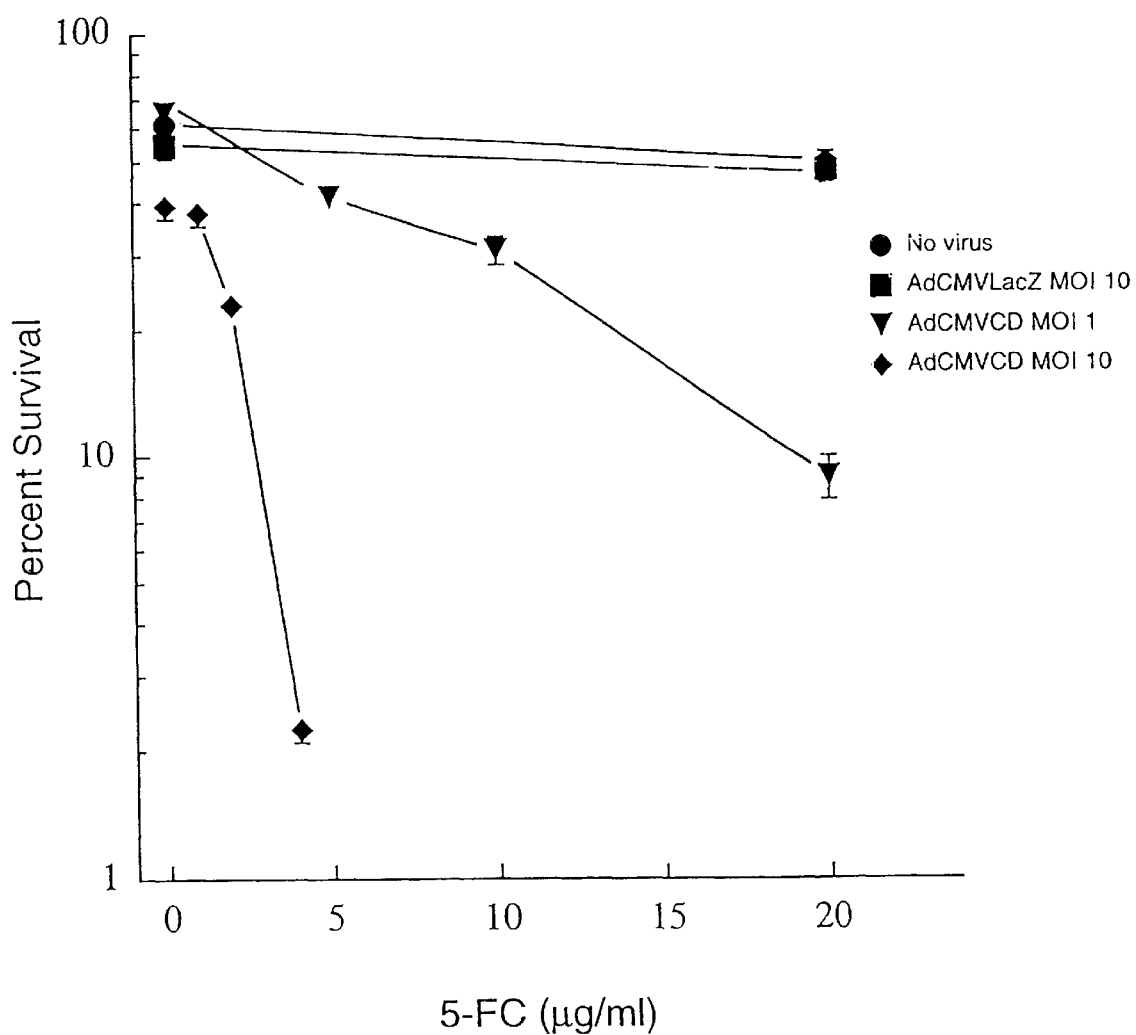
FIG. 1 shows survival of WiDr cells infected with AdCMVCD at MOIs of 1 and 10 and exposed to 5-FC for 3 days prior to plating for colony formation. Uninfected and AdCMVLacZ infected WiDr cells with and without 5-FC served as controls. The values represent the mean of 2–6 experiments done in triplicate determinations for each condition. Error bars represent the standard error of the mean.

The present invention concerns in vivo transfection of cancer cells in solid tumors with an adenovirus encoding the cytosine deaminase gene, administration of systemic 5-FC, and radiation therapy of the tumor which resulted in tumor regression and prolonged tumor growth inhibition compared to control treatments with molecular chemotherapy or radiation therapy alone. This is the first description of how to transfect established tumors in vivo with the cytosine deaminase gene to produce enhanced therapeutic effects with the combination of molecular chemotherapy and radiation therapy. Conventional systemic administration of 5-FU produces dose limiting normal tissue toxicity. The local production of 5-FU within a tumor transfected with the cytosine deaminase gene and systemic administration of 5-FC, results in higher intratumor concentrations of 5-FU than achievable with systemic administration of 5-FU, thus improving the therapeutic ratio in combination with radiotherapy. The combination of molecular chemotherapy and radiation therapy improves treatment of a variety of cancers in humans including colon cancer, pancreatic cancer, prostate cancer, lung cancer, brain cancer, head and neck cancer and cholangiocarcinoma.

The present invention can be utilized in local and regional situations where the cancer is accessible for intratumor or regional injection of the cytosine deaminase vector. Tropism-modified adenovirus or an adenovirus encoding the cytosine deaminase gene under control of a tumor specific promoter may be required for selective gene delivery to disseminated metastatic cancer. Native adenoviral tropism can be redirected through other cell surface receptors, such as fibroblast growth factor (FGF) receptor. The present invention used targeted adenovirus to the FGF receptor as a vehicle for the delivery of cytosine deaminase to hepatobiliary tumor cells for combination of molecular chemotherapy and radiation therapy studies. The results suggest that improved gene expression may be achieved via this adenoviral-conjugate mechanism to circumvent current limitations of cancer gene therapy to solid gastrointestinal malignancies.

Thus, the present invention provides a method of treating an individual having a solid tumor, comprising the steps of treating the individual with an adenovirus encoding a cytosine deaminase gene; administering 5-FC to the individual; and treating the individual with external beam irradiation. Representative cancers treated using this method include colon cancer, pancreatic cancer, prostate cancer, lung cancer, brain cancer, head and neck cancer or cholangiocarcinoma. Preferably, the adenovirus is under control of a promoter or tumor specific promoter such as a carcinoembryonic antigen promoter, DF3/MUC1 promoter, a prostate specific antigen promoter, surfactant protein A promoter, leukoprotease inhibitor promoter, erbB-2 promoter, midkine promoter, cyclooxygenase-2 promoter, alpha fetoprotein promoter and E2F promoter.

Generally, any adenovirus encoding a cytosine deaminase gene may be used in the methods taught herein; one example is the *E. coli* cytosine deaminase gene. In this method, 5-FC is typically administered in a dosage of about 400–500 mg/kg twice daily and the external beam radiation is generally applied daily at a single dose of from about 2 Gy to about 3 Gy over a 4 to 6 week period. Alternatively, brachytherapy can be used as the radiation therapy. This produces greater cytotoxicity of neoplastic cells compared to treatment with adenovirus alone or external beam radiation alone.

The present invention is also directed to a method of treating an individual having a cancer, comprising the steps of combining a ligand that binds to a tumor cellular receptor and an adenoviral vector encoding a cytosine deaminase gene to form a complex; treating the individual with the complex; administering 5-FC to the individual; and treating the individual with radiation therapy. Preferably, the tumor receptor binds to the adenoviral vector. Representative cancers treated using this method include colon cancer, pancreatic cancer, prostate cancer, lung cancer, brain cancer and cholangiocarcinoma. Generally, the ligand to cellular receptor is selected from the group consisting of basic fibroblast growth factor (FGF2), epidermal growth factor and antibodies to growth factor receptors.

Preferably, the adenovirus is under control of a promoter. Generally, any adenovirus encoding a cytosine deaminase gene may be used in the methods taught herein; one example is the *E. coli* cytosine deaminase gene. In this method, 5-FC is typically administered in a dosage of from about 400–500 mg/kg twice daily and the external beam radiation is generally applied daily at a single dose of from about 2 Gy to about 3 Gy over a 4 to 6 week period. Alternatively, brachytherapy can be used as the radiation therapy. This produces greater cytotoxicity of neoplastic cells compared to treatment with adenovirus alone or external beam radiation alone.

The present invention further discloses a noninvasive method for continuous in vivo monitoring of 5-FU production via magnetic resonance spectroscopy (MRS). Magnetic resonance spectroscopy is capable of monitoring the biodistribution of 5-FU secondary to its ability to detect fluorine-19. Magnetic resonance spectroscopy has been able to discriminate between both the prodrug (5-FC), the active drug (5-FU) and some of the active fluorinated metabolites. The benefits of using magnetic resonance spectroscopy for detecting fluorinated compounds include the following: high detection sensitivity, low background signal, 100% natural abundance and a spin of 1/2 (41).

The present invention uses magnetic resonance spectroscopy to monitor 5-FU concentrations in vivo following intratumoral injection of an adenovirus encoding the gene for cytosine deaminase and intravenous injection of 5-FC b.i.d for 5 days. Subcutaneous and metastatic pancreatic and colon cancer models are used to monitor the pharmacokinetics of 5-FU production and elimination from tumor and normal organs after transfecting these tumors with cytosine deaminase containing adenovirus.

There is a need for continuous production of 5-FU at the site of a tumor mass to maximize therapeutic efficacy and a means to detect and quantitate its concentration in tumor and in normal tissues over time in order to develop procedures that maximize 5-FU production. Magnetic resonance spectroscopy allows for monitoring this prodrug activation therapy through the following: the identification of tumor and normal tissue sites of production or accumulation of 5-FU, the discrimination of both 5-FC clearance/5-FU production, the determination of the residence time of 5-FU, the production of metabolites of the active drug, along with the determination of the elimination kinetics of 5-FU from tumor and normal organs. The information that magnetic resonance spectroscopy can provide about the pharmacokinetics of these agents can help develop procedures to maximize the effectiveness of this therapy with the potential to maximize tumor regression.

Previous studies using magnetic resonance spectroscopy did not take into account the effects of multiple dosing of the prodrug 5-FC in order to help maintain a continuous production of 5-FU or the use of multiple injections of an adenoviral vector to maximize cytosine deaminase gene transfer (41). Given the desire to maintain a continuous production of 5-FU, magnetic resonance spectroscopy can aid in guiding the dosing of the prodrug and the adenovirus along with monitoring the formation/elimination of 5-FU. Thus, the information that magnetic resonance spectroscopy can provide concerning the pharmacokinetics of 5-FU is valuable for development of prodrug activation gene therapy approach and provides the utility for further application to human clinical trials.

In still another embodiment of the present invention, there is provided a method of monitoring continuous conversion of 5-fluorocytosine to 5-fluorouracil in a tumor, wherein the tumor is treated with multiple doses of 5-fluorocytosine and multiple doses of adenovirus encoding a cytosine deaminase gene, comprising the steps of placing the treated tumor in a magnet; and evaluating the presence of 5-fluorocytosine and 5-fluorouracil by magnetic resonance spectroscopy over a course of time, wherein a lesser amount of 5-fluorocytosine and greater amount of 5-fluorouracil indicates increased conversion of 5-fluorocytosine to 5-fluorouracil. Preferably, the tumor is further treated with radiation.

In still yet another embodiment of the present invention, there is provided a method of monitoring continuous conversion of 5-fluorocytosine to 5-fluorouracil in a tumor, wherein the tumor is treated with multiple doses of 5-fluorocytosine and multiple doses of cytosine deaminase gene encoding adenovirus targeted by a ligand to a tumor cellular receptor, comprising the steps of placing the treated tumor in a magnet; and evaluating the presence of 5-fluorocytosine and 5-fluorouracil by magnetic resonance spectroscopy over a course of time, wherein a lesser amount of 5-fluorocytosine and a greater amount of 5-fluorouracil indicates increased conversion of 5-fluorocytosine to 5-fluorouracil. Preferably, the tumor is further treated with radiation.

In a further embodiment of the instant invention, there is provided an adenovirus encoding a cytosine deaminase gene, which selectively replicates in tumor cells. One manner in which this may be accomplished is by designing an adenovirus which has a complete E1A gene but lacks an E1B gene. The resulting adenovirus will selectively replicate in cells with a defective p53 pathway. AdE1ACD is an example of such an adenovirus.

Another embodiment of the instant invention is directed to a method of treating an individual having a solid tumor with the selectively replicating adenovirus encoding cytosine deaminase by infecting the individual with such an adenovirus, subsequently administering 5-fluorocytosine followed by radiation therapy.

In yet another embodiment of the present invention, an adenovirus is provided which coexpresses cytosine deaminase and uracil phosphoribosyltransferase. Preferably the cytosine deaminase and uracil phosphoribosyltransferase are expressed as a fusion protein, such as in AdCDUPRT. Another embodiment of the instant invention is directed to a method of treating an individual having a solid tumor by administering an adenovirus coexpressing cytosine deaminase and uracil phosphoribosyltransferase followed by 5-fluorocytosine and radiation therapy.

The following examples are given for the purpose of illustrating various embodiments of the invention and are not meant to limit the present invention in any fashion.

EXAMPLE 1

Cell Culture

The human colon carcinoma cell line WiDr (ATCC CCL-218 Rockville, Md.) was grown in Earle's modified Eagle's medium (EMEM) (Gibco-BRL, Grand Island, N.Y.) supplemented with 10% fetal bovine serum (FBS) (Summit, Fort Collins, Colo.), 2 mM glutamine, and 1% non-essential amino acids in a humidified atmosphere with 5% $CO_2$. The human cholangiocarcinoma cell line SK-ChA-1 was the gift of A. Knuth, Ludwig Institute for Cancer Research, London, UK. SK-ChA-1 cells were maintained in RPMI-1640 medium supplemented with 2 mM L-glutamine and 10% FBS at 37° C. in a humidified 5% $CO_2$ atmosphere. The transformed human embryonic kidney cell line, 293, is an E1A trans-complementing cell line (Microbix, Toronto, Canada) utilized for viral propagation and titering and was maintained in Dulbecco's Modified Eagle's medium-F12 supplemented with 2 mM L-glutamine and 10% FBS at 37° C. in a 5 humidified 5% $CO_2$ atmosphere. The cells were passaged using 0.05% trypsin and 5 MM EDTA once weekly.

EXAMPLE 2

Chemotherapeutic Drugs

5-FC (Sigma, St. Louis, Mo.) was dissolved in PBS at a stock concentration of 10 mg/ml. 5-FU (50 mg/ml, Hoffman-LaRoche, Inc., Nutley, N.J.) was used as a control for clinical therapy of both colon and cholangiocarcinoma in current medical practice.

EXAMPLE 3

Adenovirus Production and Characterization

The production, characterization, and functional validation of the AdCMVCD vector was described (14, 15). Briefly, the cytosine deaminase gene was cloned into the adenoviral shuttle vector pACCMVpLpARS (+) (provided by R. Gerard, Katholieke Universiteit Leuven, Ontario, Canada) and then co-transfected with the pJM17 rescue plasmid (provided by Dr. F. Graham, McMaster University) into 293 cells to allow for homologous recombination (28). Individual plaques were isolated and subjected to 2 further rounds of plaque purification. The final adenovirus was validated by PCR and restriction analysis. The ability of ADCMVCD to induce a functional cytosine deaminase enzyme was determined by measuring conversion of $^3$H-5-FC to $^3$H-5-FU by infected cell lysate (26).

EXAMPLE 4

In Vitro Radiation Dose Response Analysis

WiDr human colon cancer cells were plated at a density of $5 \times 10^5$ cells/well in 6-well tissue culture plates 24 hours prior to0 adenoviral infection. WiDr cells were then infected with AdCMVCD at a multiplicity of infection (MOI) of 1 or 10 plaque forming units (pfu) per cell in 0.5 ml Opti-Mem (Gibco-BRL) for 1.5 hours. A control virus that encodes the reporter gene *E. coli* LacZ which produces β-galactosidase (AdCMVLacZ) was provided by Dr. De-Chu Tang, University of Alabama at Birmingham. Viral infection was stopped by the addition of 3 ml of complete growth media and the cells were returned to the incubator overnight. The following day, media was replaced with media supplemented with the appropriate concentration of 5-FC or no drug. The cells were then incubated in 5-FC for 3 days. The cells were then mock irradiated or irradiated on ice using a Picker $^{60}$Co therapy unit (Cleveland, Ohio) at a dose rate of 80 cGy/min. The cells were then plated for colony formation. Colonies formed in 14 days and were fixed in ethanol and stained with 1% crystal violet.

SK-ChA-1 cells were infected with 10 MOI of AdCMVCD, or AdCMVLacZ, treated with 0, 10 or 20 μg/ml 5-FC for 72 hours, then irradiated with 0 or 8 Gy (80 cGy/min). The cells were irradiated on ice, then trypsinized, counted and plated in triplicate in 25 cm tissue culture dishes (Costar) in media free of 5-FC. The plates were fixed and stained 14 days later. For both WiDr and SK-ChA-1 cells, colonies containing greater than 50 cells were counted. Percent survival was calculated as the average number of colonies counted divided by the number of cells plated times plating efficiency (PE); where PE was the fraction of colonies counted divided by cells plated without radiation. The dose response curve was fitted using the Fit v 2.4 software (provided by Dr. N. Albright, University of California at San Francisco, San Francisco, Calif.).

EXAMPLE 5

Animal Studies

Athymic nude mice (Frederick Cancer Research Laboratory, Bethesda, Md.) were injected s.c. in the flank with $2\times10^7$ WiDr or SK-ChA-1 cells. Tumors were allowed to grow for 7 days at which time they were divided into various treatment groups. The WiDr tumor treatment groups included: 1) AdCMVCD, 5-FC and a single 10 Gy dose of $^{60}$Co radiation; 2) AdCMVCD, 5-FC and 3×5 Gy fractions of $^{60}$Co radiation; 3) No virus, 5-FC and 3×5 Gy fractions of $^{60}$Co radiation; 4) AdCMVCD, 5-FC and no radiation. The AdCMVCD vector was injected intratumorally (i.t.) once every other day for a total of 3 injections beginning at Day −2 relative to radiation. The 5-FC was administered for 7 days as 500 mg/kg twice daily by i.p. injection beginning at Day −2 relative to radiation. Two days following the initial adenoviral and 5-FC injection, mice were anesthetized with ketamine-HCl (Phoenix Scientific, Inc., St. Joseph, Mo.) and irradiated. The first 5 Gy fraction was given followed by 2 subsequent 5 Gy fractions given daily. The 10 Gy single dose was given on the same day as the second 5 Gy fraction.

The SK-ChA-1 tumor treatment groups included: 1) AdCMVCD, 5-FC, and 5×2 Gy, 2) AdCMVCD, 5-FC, without radiation, 3) 5-FU (30 mg/kg/day as 15 mg/kg twice daily) without radiation, 4) 5×2 Gy radiation and 5-FU (30 mg/kg/day as 15 mg/kg twice 5 daily), and 5) no treatment. The mice with SK-ChA-1 tumors received 5-FC (400 mg/kg twice daily by i.p. injection) beginning at Day −2 relative to radiation therapy, and continued for 7 days. The mice were anesthetized with ketamine-HCl, and their tumors irradiated using the Picker $^{60}$Co therapy unit. All mice were shielded with a specially designed lead apparatus that allowed irradiation of a single flank (6 mice at a time). Tumor growth was measured 3 times weekly in 2 dimensions using a Vernier caliper and the tumor size (length×width) was calculated. The animals were maintained in a laminar flow room and fed sterilized chow and tap water in accordance with University of Alabama Animal Resource Department protocols.

EXAMPLE 6

Statistical Methods

The logrank test was used to assess if there were differences among the four groups of animals bearing WiDr xenografts in overall survival, time to tumor doubling, and time to regrowth. Specific pairwise comparisons between treatment groups for time to tumor regrowth and time to tumor doubling were also made using the logrank test. Fisher's Exact test was used to assess if there were any differences in tumor regression rate between groups.

The logrank test was used to assess if there were differences among the five groups of animals bearing SK-ChA-1 xenografts in time to tumor doubling and time to regrowth. Specific pairwise comparisons were made between treatment groups for time to tumor regrowth due to lack of an overall difference in time to tumor doubling. The level of significance used for all comparisons was P<0.05.

EXAMPLE 7

Results

The ability of AdCMVCD infection combined with 5-FC to kill WiDr cells was tested. Survival was determined following AdCMVCD infection at MOI's of 1 and 10 with varying concentrations of 5-FC (FIG. 1). Increased cytotoxicity at each MOI of AdCMVCD infection with increasing 5-FC concentration was observed in the WiDr cells. Maximal cell killing was observed at 1 and 10 MOI with administration of 20 and 4 μg/ml 5-FC, respectively. No changes in cytotoxicity were observed for the AdCMVLacZ or no virus control at the maximum tested 5-FC concentration (20 μg/ml). The survival level obtained with virus and prodrug was used to normalize for the combination radiation survival values.

Figure 2:
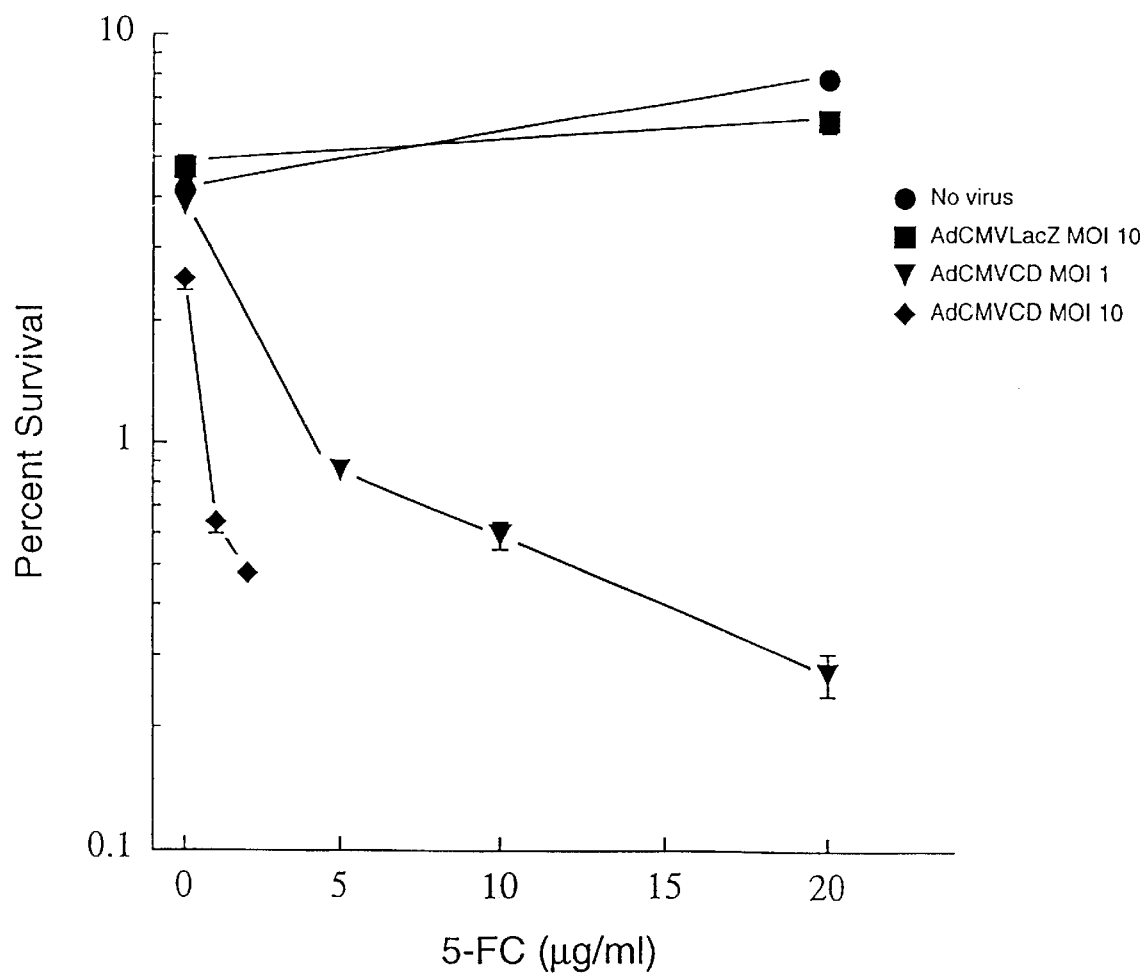
FIG. 2 shows survival of WiDr cells at 8 Gy following infection with AdCMVCD at MOIs of 1 and 10. Uninfected and AdCMVLacZ infected WiDr cells with and without 5-FC served as controls. Cells were exposed to 5-FC for 3 days prior to irradiation and plating for colony formation. The values represent the mean of 2–6 experiments done in triplicate determinations for each condition. Error bars represent the standard error of the mean.

Whether expression of cytosine deaminase with 5-FC treatment would enhance radiation cell killing at a single dose of radiation in WiDr cells was then determined. AdCMVCD and 5-FC concentrations giving at least 90% killing alone were used in the radiation survival experiments. Percent survival following a single 8 Gy radiation dose following AdCMVCD infection at 1 and 10 MOI with increasing 5-FC concentrations was determined for WiDr cells (FIG. 2). An enhanced radiation cytotoxicity was observed with increasing 5-FC concentrations at each MOI tested. The maximal radiation enhanced cytotoxicity was observed at 1 and 10 MOI with 20 and 2 μg/ml 5-FC, respectively.

Figure 3:
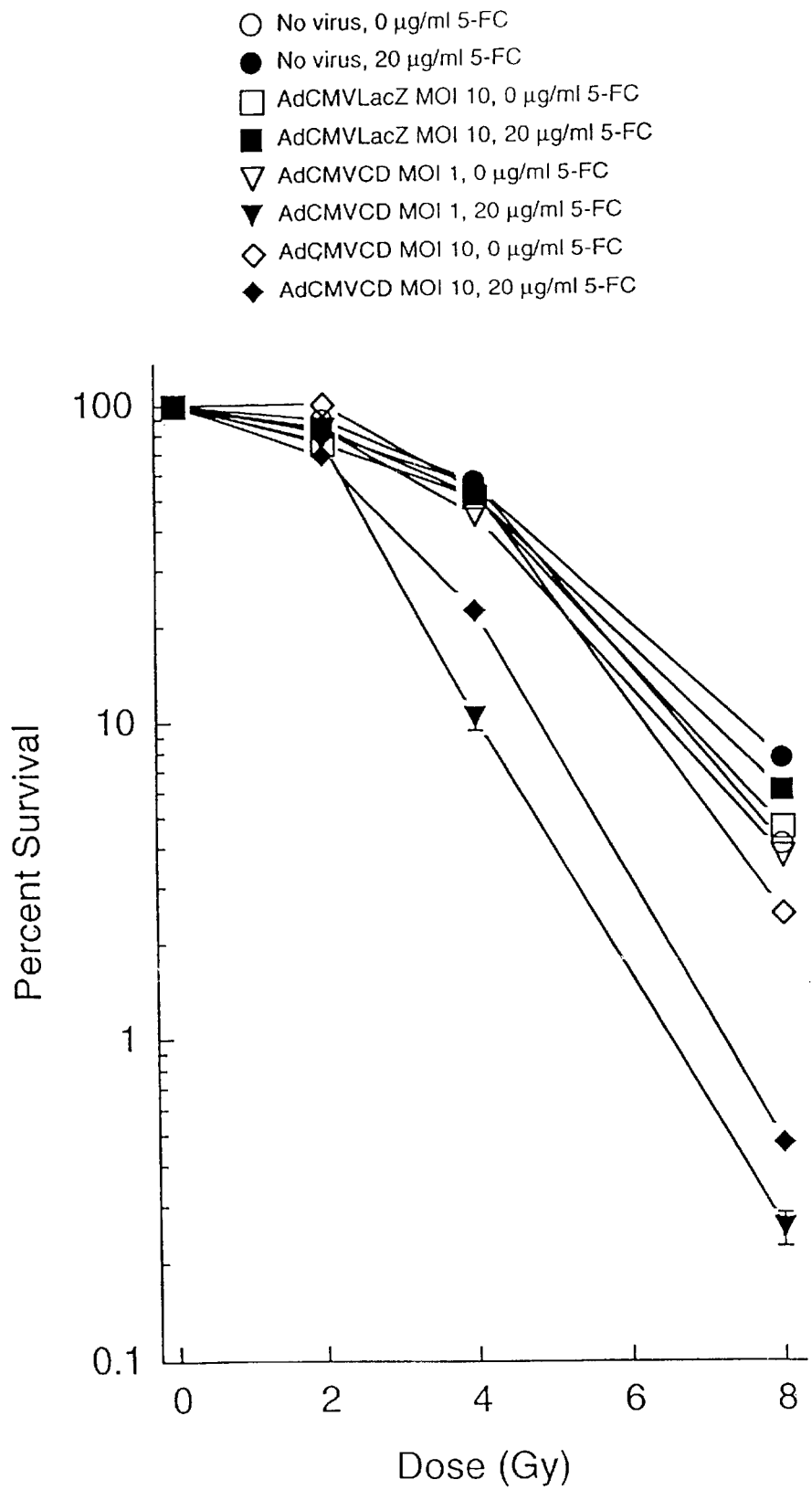
FIG. 3 shows radiation dose response for WiDr cells infected with AdCMVCD at MOIs of 1 and 10 and exposed to 5-FC for 3 days prior to irradiation. Uninfected and AdCMVLacZ infected WiDr cells with and without 5-FC served as controls. The values represent the mean of 2–6 experiments done in triplicate determinations for each condition. Error bars represent the standard error of the mean.

The conditions that gave the greatest radiosensitization at 8 Gy were identified for WiDr and used to establish a dose response relationship (FIG. 3). The greatest increase in cell killing was observed with 1 MOI and 20 μg/ml of 5-FC. The radiation survival curve parameters calculated using the linear quadratic and single hit multiple target (SHMT) models are listed in Table 1. Only the two AdCMVCD groups with 20 or 2 μg/ml 5-FC had non zero α values (0.221 and 0.065 for 1 and 10 MOI, respectively). The β values were similar for all groups. For the SHMT model, the lowest $D_0$ values were for the AdCMVCD groups with 5-FC (0.990 and 1.034 for 1 and 10 MOI, respectively). However AdCMVCD, 10 MOI without 5-FC had a low $D_0$ of 1.177 compared to the range of the other groups of 1.338–1.760. Additionally, the lowest $D_q$ values were obtained for the AdCMVCD groups with 5-FC (1.952 and 2.569 for 1 and 10 MOI, respectively) while the values for the other groups ranged from 3.207–3.825.

TABLE 1

Radiobiologic parameters of in vitro survival curves for human colon cancer cell line WiDr infected with Ad CMVCD, AdCMVLacZ or no viral infection, treated with 5-FC and exposed to $^{60}$Co radiation.

| Treatment Group | Linear Quadratic Parameters | | | | Single Hit Multiple Target Parameters | | |
|---|---|---|---|---|---|---|---|
| | α | β | α/β | $r^2$ | $D_o$ | $D_q$ | $r^2$ |
| No Viral Infection, 0 μg/ml 5-FC | 0 | 0.050 | 0 | 0.993 | 1.338 | 3.825 | 0.999 |
| No Viral Infection, 20 μg/ml 5-FC | 0 | 0.040 | 0 | 0.999 | 1.760 | 3.679 | 0.998 |
| AdCMVLacZ, 10 MOI, 0 μg/ml 5-FC | 0 | 0.047 | 0 | 0.996 | 1.502 | 3.614 | 0.993 |
| AdCMVLacZ, 10 MOI, 20 μg/ml 5-FC | 0 | 0.044 | 0 | 1.00 | 1.673 | 3.459 | 0.999 |
| AdCMVCD, 1 MOI, 0 μg/ml 5-FC | 0 | 0.051 | 0 | 1.00 | 1.496 | 3.207 | 0.999 |
| AdCMVCD, 1 MOI, 20 μg/ml 5-FC | 0.221 | 0.069 | 3.211 | 0.979 | 0.990 | 1.952 | 0.996 |
| AdCMVCD, 10 MOI, 0 μg/ml 5-FC | 0 | 0.059 | 0 | 0.988 | 1.177 | 3.674 | 1.00 |
| AdCMVCD, 10 MOI, 2 μg/ml 5-FC | 0.065 | 0.076 | 0.851 | 1.00 | 1.034 | 2.569 | 0.998 |

Figure 4:
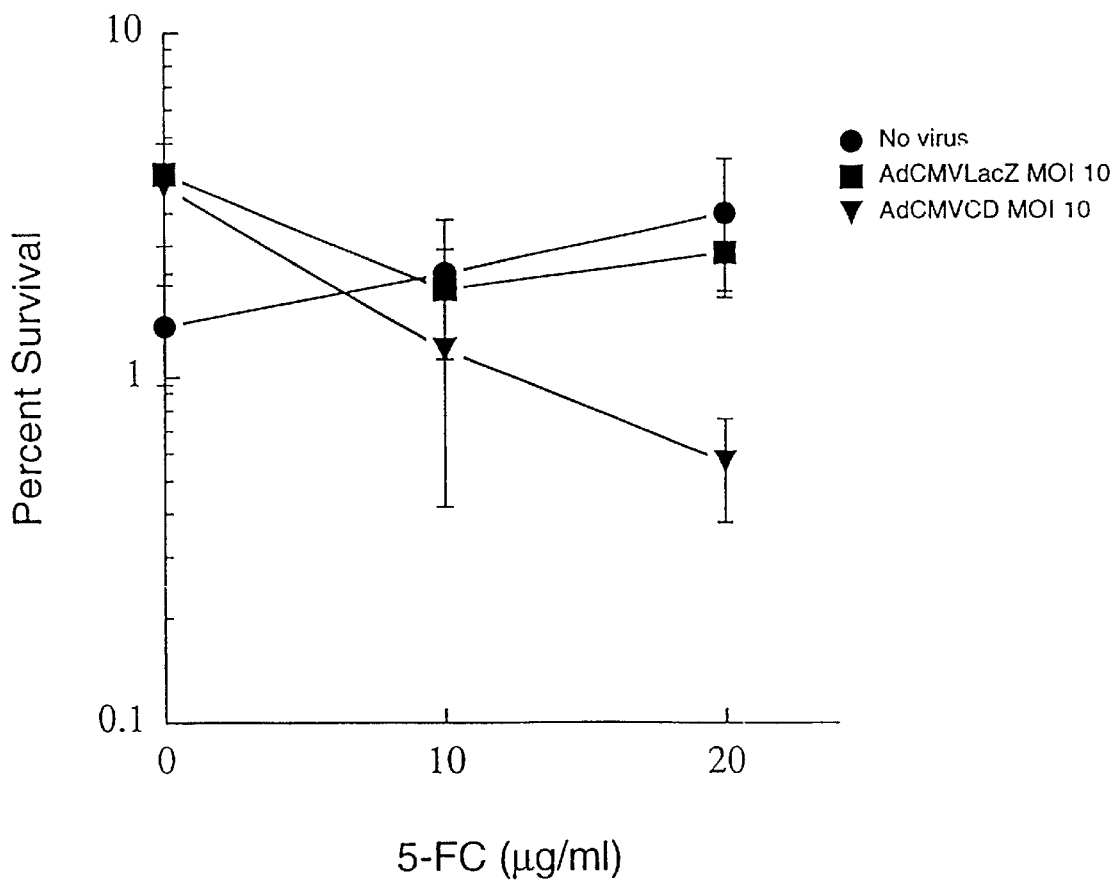
FIG. 4 shows survival of SK-ChA-1 cells following infection with AdCMVCD at an MOI of 10, treated with 5-FC and 8 Gy radiation. Uninfected cells and AdCMVLacZ infected SK-ChA-1 cells with and without 5-FC served as controls. Cells were exposed to 5-FC (0, 10 or 20 $\mu$g/ml) for 3 days prior to irradiation and plating for colony formation. The values represent the mean of 6 replicates in 2 separate experiments. Error bars are the standard error of the mean.

The radiation induced killing of SK-ChA-1 cells treated with AdCMVCD infection, 5-FC, and 8 Gy radiation is illustrated in FIG. 4. The enhanced effects of combined treatment were most evident at the 20 μg/ml dose of 5-FC. A detailed radiation dose response analysis was published in Table 1 of Pederson et al. (14). These prior studies demonstrated a $D_0=0.968$ and $α=0.444$ for the combined modality treatment of the SK-ChA-1 cholangiocarcinoma large value of α and small $D_0$ indicate significant reduction in cell survival as a result of the combined treatments with low (2 Gy) and high (8 Gy) single fraction radiation exposures. A similar trend was observed in the radiation survival parameters obtained using the WiDr colon cancer cells (Table 1). The largest a values and smallest $D_0$ values were observed for the AdCMVCD infected cells treated with 5-FC.

Figure 5A:
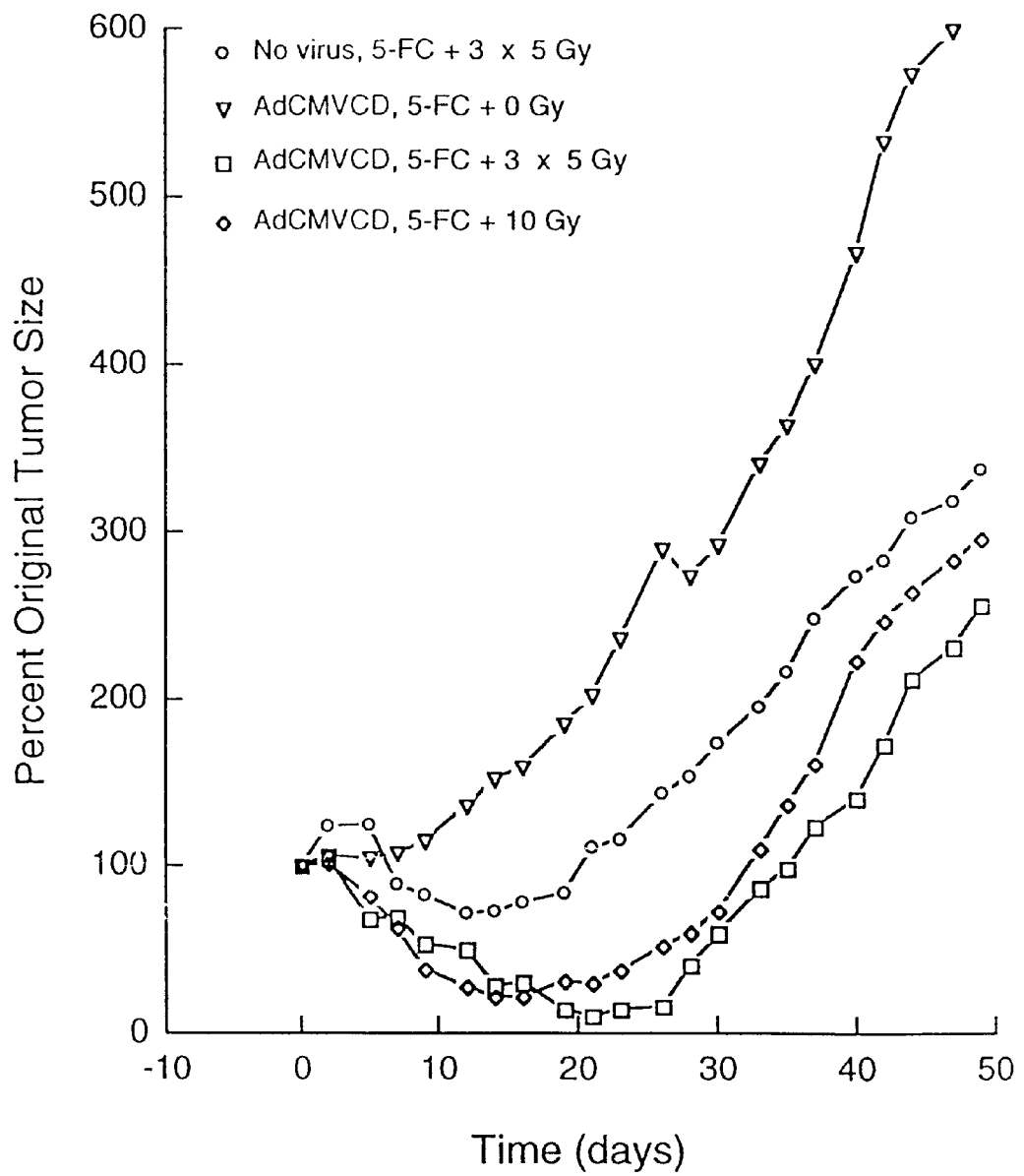
FIG. 5A shows growth of WiDr colon carcinoma tumor nodules treated with AdCMVCD, 5-FC and $^{60}$Co radiation. Mice received $2\times10^7$ WiDr cells by s.c. injection, and tumors with diameters of 5–10 mm formed in 7 days. At this time, three injections of AdCMVCD ($1\times10^9$ pfu) were administered intratumorally on days −2, 0, and 2 relative to radiation treatment on day 0. All animals received 5-FC (500 mg/kg twice daily by i.p. injection) beginning on day −2 for 7 days. The radiation treatment groups received 10 Gy $^{60}$Co (day 1) or 5 Gy (days 0, 1, and 2) to their tumor. Data points represent the mean change in tumor surface area relative to day 0 for groups of animals (n=6).
Figure 5B:
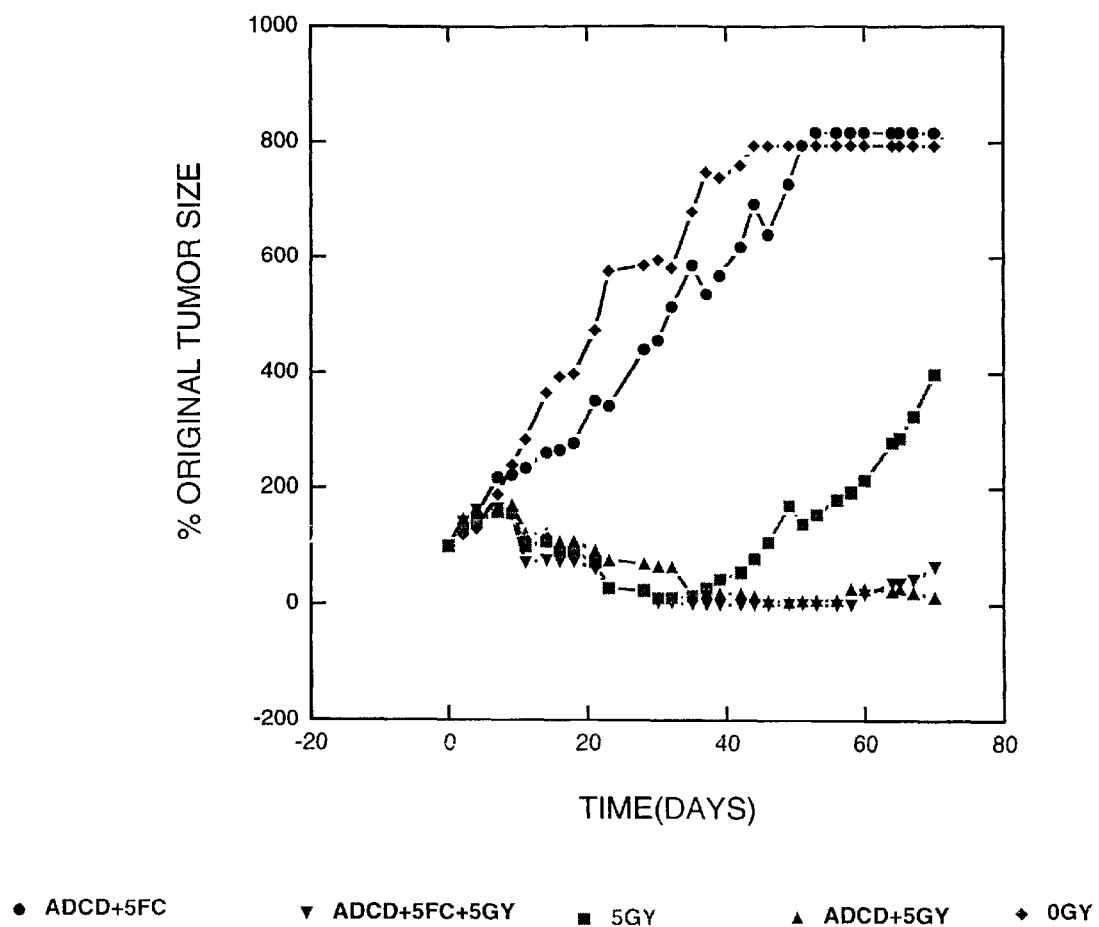
FIG. 5B shows growth of WiDr colon carcinoma tumor nodules treated with AdCMVCD, 5-FC and $^{60}$Co radiation. Mice received $2\times10^7$ WiDr cells by s.c. injection, and tumors with diameters of 5–10 mm formed in 7 days. At this time, three injections of AdCMVCD ($1\times10^9$ pfu) were administered intratumorally on days −2, 0, and 2 relative to radiation treatment on day 0. One week later, the AdCMVCD injections were repeated. All animals received 5-FC (500 mg/kg twice daily by i.p. injection) beginning on Day −2 for 14 days. The radiation treatment groups received 5 Gy (days 0, 1, 2, 7 and 8) to their tumor. Data points represent the median change in tumor surface area relative to day 0 for groups of animals (n=10).

To establish the efficacy of cytosine deaminase and 5-FC with radiation therapy for WiDr cells in vivo, subcutaneous WiDr tumors were established in the flanks of athymic nude mice. The irradiation conditions included a single 10 Gy dose or 3×5 Gy fractions on 3 consecutive days. Two mice from each combination therapy group died from the treatment. Tumor growth was measured and the change in tumor size determined over time. Two of 6 tumors in the combined AdCMVCD+5-FC+3×5 Gy modality group regressed but subsequently recurred, while 3 of 6 tumors regressed then recurred in the 10 Gy combined modality group. The AdCMVCD+5-FC+10 Gy and the AdCMVCD+5-FC+3×5 Gy groups produced the longest times to tumor regrowth and tumor doubling, but were not significantly different from each other. The AdCMVCD+5-FC+10 Gy, AdCMVCD+5-FC+3×5 Gy and the 5-FC+3×5 Gy groups all had significantly longer times to tumor doubling (FIG. 5) than the AdCMVCD+5-FC+0 Gy group (P=0.0037, 0.01, and 0.0006, respectively) as well as significantly longer times to tumor regrowth (P=0.001, 0.0026, and 0.001, respectively). Both the AdCMVCD+5-FC+10 Gy and the AdCMVCD+5-FC+3×5 Gy groups had significantly longer times to tumor regrowth than the 5-FC+3×5 Gy group (P=0.0103 and 0.0153, respectively) (FIG. 5A). The 5-FC+3×5 Gy and the AdCMVCD+5-FC treated groups were not significantly different. No other significant pairwise differences existed in time to tumor regrowth or doubling. Tumor growth was inhibited for a longer period with AdCMVCD+5-FC+5×5 Gy (FIG. 5B).

Figure 6:
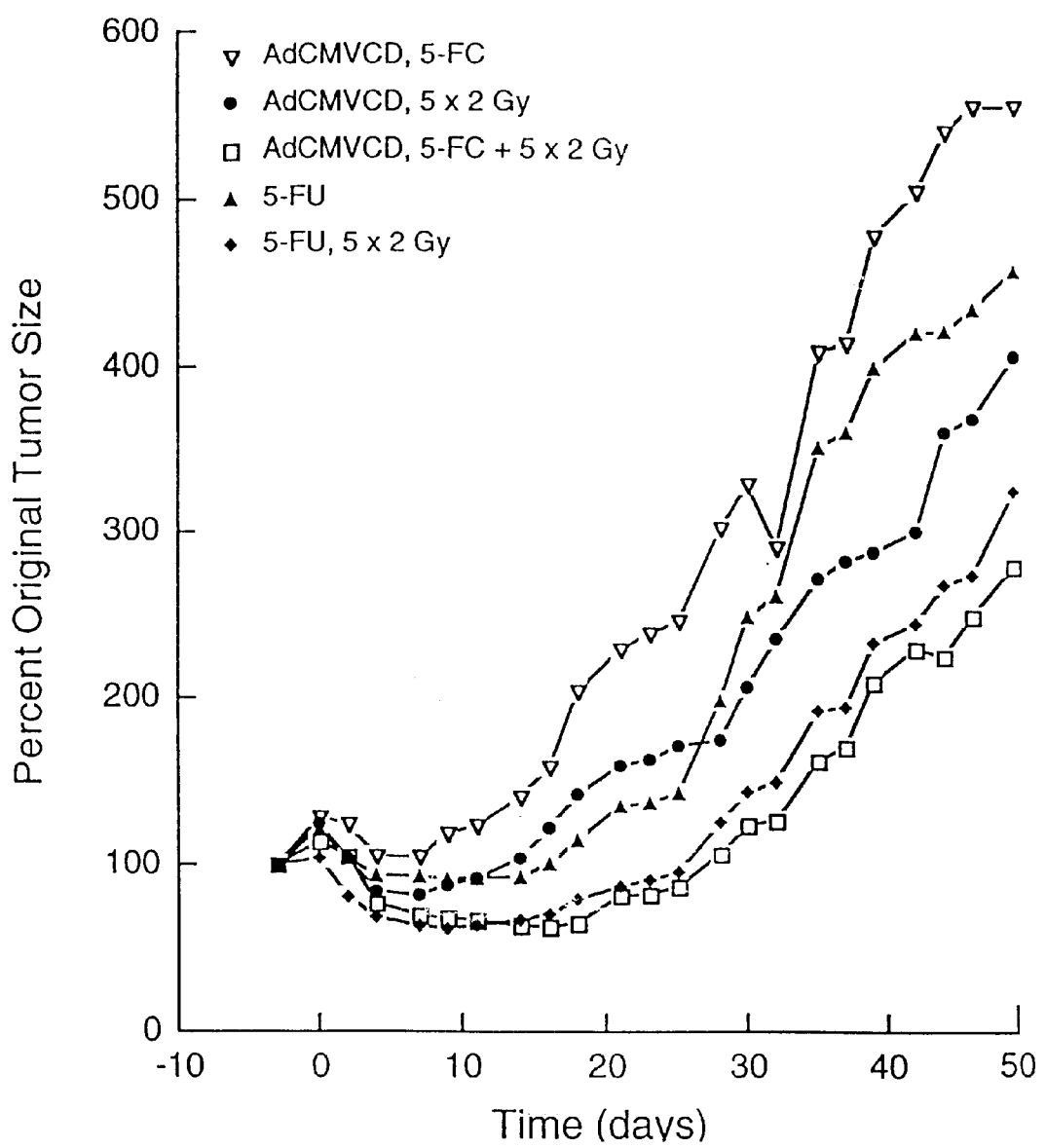
FIG. 6 shows growth of SK-ChA-1 cholangiocarcinoma tumors treated with AdCMVCD, 5-FC, and 5×2 Gy $^{60}$Co radiation. Controls included 5-FU with and without radiation, AdCMVCD+5-FC, and no treatment. Mice received 2×10$^7$ SK-ChA-1 cells by s.c. injection, and tumors with diameters of 5–10 mm formed in 7 days. At this time, three injections of AdCMVCD (1×10$^9$ pfu) were administered intratumorally on days −2, 0, and 2 relative to initiation of radiation treatment on day 0. Animals received 5-FC (400 mg/kg twice daily by i.p. injection) or 5-FU (15 mg/kg twice daily by i.p. injection) beginning on day −2 for 7 days. The radiation treatment group received 2 Gy $^{60}$Co (days 0–4) to their tumor. Data points represent the mean change in tumor surface area relative to day 0 for groups of animals (n=10).

The AdCMVCD+5-FC+5×2 Gy and the 5-FU+5×2 Gy groups had the longest times to SK-ChA-1 tumor regrowth, however they were not significantly different from each other (FIG. 6). No differences existed in time to tumor doubling among the treatment groups. The time to tumor regrowth did not differ between the AdCMVCD+5-FC and 5-FU alone treatment groups. The AdCMVCD+5-FC+5×2 Gy group had a significantly longer time to tumor regrowth compared to the 5-FU alone and the AdCMVCD+5×2 Gy groups (P=0.0126 and 0.0121, respectively) (FIG. 6). The 5-FU+5×2 Gy group also had a significantly longer time to tumor regrowth compared to the 5-FU alone and AdCMVCD+5×2 Gy groups (P=0.0204 and 0.0180, respectively).

The use of gene transfer methods employing adenoviral vectors to sensitize cells to the effects of ionizing radiation can be used for solid tumor therapy. An adenovirus encoding the cytosine deaminase gene used with the prodrug 5-FC can lead to enhanced cell killing when used in combination with ionizing radiation in vitro and in vivo for 2 human gastrointestinal malignancies, colon carcinoma and cholangiocarcinoma. Previous studies in human cholangiocarcinoma (14, 15) demonstrated the in vitro radiosensitizing effects of combining cytosine deaminase transgene expression with 5-FC prodrug treatment and single fraction radiation therapy. The small $D_0$ and large α values obtained for the combination treatment groups indicate cytotoxic effects both at high and low radiation doses for the WiDr cells which is similar to what occurred with the cholangiocarcinoma cells.

From the encouraging results of the in vitro evaluation of induction of radiosensitivity for both colon cancer and cholangiocarcinoma cells, in vivo models were evaluated. For SK-ChA-1 cholangiocarcinoma tumors, an enhanced anti-tumor effect was seen from combined AdCMVCD infection, 5-FC administration, and a single 10 Gy radiation dose compared to AdCMVCD infection and 5-FC alone. Radiation therapy in the clinical setting is traditionally delivered in daily 2 Gy doses over 4–6 weeks. Analysis of this format of radiation therapy and CD/5-FC gene therapy with human colon cancer and cholangiocarcinoma indicated the fractionated delivery of 3×5 Gy doses or 5×2 Gy doses was at least as effective as a single 10 Gy fraction or with systemically administered 5-FU and 5×2 Gy doses. Thus, a measurable anti-tumor effect was observed with CD/5-FC gene therapy in combination with low dose fractionated radiation therapy.

Khil et al. showed that the cytosine deaminase gene stably transfected into WiDr cells was able to enhance radiation cell killing in vitro (13). Adenoviral vectors have been used in many gene transfer and therapy studies. The use of adenoviral vectors to encode cytosine deaminase and convert 5-FC to 5-FU to achieve cell killing has been reported (25, 26). Ohwada et al. delivered a n adenoviral vector encoding cytosine deaminase into normal tissue 0.8–1 cm from the site of colon tumor xenografts in the liver of mice and systemically delivered 5-FC to suppress metastatic tumor growth (29). Therefore, there is potential that treatment of primary tumor nodules with the combination of 5-FC conversion to 5-FU by the cytosine deaminase gene and radiation could lead to increased local control while the production of 5-FU would serve to suppress metastatic growth.

Both metastatic colon carcinoma and locally advanced cholangiocarcinoma are difficult clinical problems, and have been resistant to single modality therapy (6, 30, 31). The gene therapy approach of molecular chemotherapy combined with radiation therapy provides a new approach to the treatment of solid tumors. The ability of 5-FC and 5-FU to freely diffuse across cell membranes is one advantage of the CD/5-FC toxin gene/prodrug strategy. This is in contrast to the HSVtk/GCV system where cellular gap junctions are a vital component of the bystander effect (32, 33). Another advantage of CD/5-FC demonstrated here with respect to the WiDr colon cancer model was efficacy at a very low viral concentration of 1 MOI. A MOI of 1 with a high 5-FC concentration (20 $\mu$g/ml) was more effective than a MOI of 10 and a low 5-FC concentration (2 $\mu$g/ml). This is an important observation since it may be difficult to achieve 100% infection of cells in solid tumors in situ. In vivo studies lend support to the possibility that less than 100% tumor infection can be effective. Although it is likely that only a fraction of tumor cells in the xenografts were infected, a significant regrowth delay was observed in the irradiated, AdCMVCD infected tumors treated with 5-FC compared to irradiation alone or the AdCMVCD infected and 5-FC treated tumors without irradiation. An important observation was that low dose multifraction radiation treatment in combination with CD/5-FC gene therapy was effective in inhibiting tumor growth. The ability to achieve greater regrowth delay with combined modality therapy with an adenoviral vector in vivo demonstrates the potential of this cancer gene therapy strategy as a treatment modality that can be tested in human clinical trials.

Such enzyme/prodrug strategy consisting of CD/5-FC relies on diffusion of the cytotoxic enzymatic product 5-FU to kill non-transduced tumor cells. It can be utilized in local and regional situations where the cancer is accessible for intratumor or regional injection of the cytosine deaminase vector. Tropism-modified adenovirus or an adenovirus encoding the cytosine deaminase gene under control of a tumor specific promoter may be required for selective gene delivery to disseminated metastatic cancer. However, native adenoviral tropism can be redirected through other cell surface receptors, such as fibroblast growth factor (FGF) receptor. The following examples demonstrate methods to increase gene delivery via vector binding to tumor markers. Adenovirus vector was redirected via FGF receptor for the delivery of cytosine deaminase gene to hepatobiliary tumor cells for combination of molecular chemotherapy and radiation therapy studies.

EXAMPLE 8
Cell Lines

The human cholangiocarcinoma cell lines SK-ChA-1 and Oz were from Dr. A. Knuth (Ludwig Institute for Cancer Research, If London, UK) and Dr. N. F. LaRusso (Mayo Clinic, Rochester Minn.) respectively. BXPC-3, ASPC-1 and CFPAC-1 human pancreatic carcinoma cell lines were obtained from the American Type Culture Collection (ATCC CRL-1687, ATCC CRL-1682 and ATCC CRL-1918; Rockville Md.). SK-ChA-1, Oz and BXPC-3 cells were maintained in RPMI-1640 medium supplemented with L-glutamine (2 mM), and 10% heat inactivated fetal bovine serum (FBS) (Summit Biotechnology, Ft. Collins, Colo.) at 37° C. in a humidified 5% $CO_2$ atmosphere. ASPC-1 cells were maintained in RPMI-1640 medium supplemented with L-glutamine (2 MM), and 20% FBS at 37° C. in 5% $CO_2$ atmosphere.

EXAMPLE 9
Fab-FGF2 and Fab'-FGF2 Conjugates

The recombinant adenoviral vectors (AdCMVLacZ, AdCMVLuc, and AdCMVCD) were redirected with FGF2 to the FGF receptor by utilization of a bi-specific conjugate constructed and validated as described (34). Fab-FGF2 was constructed by utilizing the 1D6.14 anti-adenoviral knob monoclonal antibody, and production of the Fab fragment. This moiety was conjugated to human FGF2 by disulfide linkage.

To decrease the heterogeneity of the Fab-FGF2 conjugates, a Fab'-FGF2 conjugate was generated. The ascites containing the anti-knob 1D6.14 antibody was loaded onto a protein A column in phosphate buffer, pH 7.4 and eluted with 0.1 M glycine pH 3.5. The purified IgG was digested with immobilized pepsin to obtain F(ab)'$_2$ fragments. The digestion mixture was purified by protein A chromatography and the flow-through containing the F(ab)'$_2$ was buffer exchanged by gel filtration chromatography (Sephacryl S-200, Pharmacia, Uppsala, Sweden). The purified F(ab)'$_2$ fragments were mildly reduced with 2-mercaptoethylamine-HCl. The sulfhydryl group on the Fab' fragment was activated with Ellman's reagent (DTNB) at a 1:3 molar ratio for 30 min which results in Fab'-TNB. Excess DTNB was removed by diafiltration using an Amicon stirred cell apparatus (Beverly, Mass.) equipped with a YM30 and then put through a 0.2 $\mu$m filter to obtain pure TNB-Fab'. TNB-Fab' and FGF2 were mixed at a 1:1 molar ratio and incubated for 12–16 hours at 4° C. to generate the Fab'-FGF2 conjugate. The reaction mixture was purified by heparin affinity chromatography (Heparin Sepharose, FF, Uppsala, Sweden). Fractions containing Fab'-FGF2 were further purified by gel filtration (Sephacryl S-100 HR, Pharmacia, Uppsala, Sweden). The Fab'-FGF2 was filtered through a 0.2 $\mu$m membrane and stored at −80° C. The material was determined to be greater than 95% pure by SE-HPLC. The Fab'-FGF2 conjugate was analyzed using the anti-knob ELISA and shown to have very similar binding characteristics as the anti-knob Fab and Fab-FGF2. In addition, the materials, final product and intermediates were also characterized by SDS-PAGE under reducing and non-reducing conditions. All the materials migrated as expected and the final product was pure.

Functional validation of the conjugate moieties was defined prior to use. The Fab and Fab' moiety binding to adenoviral type 5 knob protein was confirmed by ELISA. Functional ability of the FGF2 moiety of the conjugate was evaluated using a bovine aortic endothelial cell proliferation assay. The Fab-FGF2 and Fab'-FGF2, when complexed with Ad5, showed comparable levels of gene expression when assayed on SKOV3.ip1 cells. Fab-FGF2 was used in the majority of the in vitro studies and the in vivo study utilized the Fab'-FGF2 as the retargeting moiety.

EXAMPLE 10
Recombinant Adenoviruses

E1A deficient replication-incompetent serotype 5 adenoviral vectors were used to analyze Fab-FGF2 and Fab'-FGF2 redirected adenoviral gene transfer. AdCMVLuc encodes the firefly luciferase gene under the control of the human cytomegalovirus (CMV) promoter/enhancer, and has been described (35). AdCMVLacZ contains the LacZ reporter gene and induces expression of the *E. coli*

β-galactosidase enzyme under control of the CMV promoter (35). AdCMVCD encodes the *E. coli* cytosine deaminase gene under control of the CMV promoter, and was constructed, functionally validated, and propagated as described (14).

EXAMPLE 11
Redirected Marker Gene Adenoviral Infections

Either AdCMVLuc or AdCMVLacZ was incubated with Fab-FGF2 conjugate in a volume of 130 μl at room temperature for 30 minutes. Dilutions of this stock to varying plaque forming units (pfu) of virus were made and then added to 30,000 cells/well in a 12 well dish (Costar, Cambridge, Mass.) and incubated at 37° C. for 2 hours. Infections were terminated by addition of 5 ml of complete media.

EXAMPLE 12
Analysis of AdCMVLuc and AdCMVLacZ Gene Expression

Luciferase assays were performed according to the manufacturer's instructions 24 hours after infection (Luciferase Assay Kit, Promega, Madison, Wis.). Briefly, cell lysates from infected cells were obtained by aspirating culture media, washing cells with PBS, and adding 150 μl of cell lysis buffer to each well. Cells were lysed at room temperature for 10 minutes and cellular debris removed by refrigerated centrifugation at 13,000×g for 5 minutes. Assay reagent was added to the cell lysates and analyzed for emitted light on a luminometer (Lumat, Berthold, Nashua, N.H.).

To analyze AdCMVLacZ gene expression, in brief, 48 hours following infection cells were fixed in 12-well dishes (Costar) with 0.5% glutaraldehyde (Sigma). The cells were washed with PBS, and stained with X-gal 5-bromo-4-chloro-3-indolyl-β-D-galactoside substrate with 2 mM $MgCl_2$, 5 mM $K_3Fe(CN)_6$, and 0.3% Nonidet P-40 (Sigma).

EXAMPLE 13
In Vitro Adenoviral Infection for Fab-FGF2 Redirection of Reporter Gene Expression and Measurement of Reporter Gene Expression Cells were plated at a density of $4 \times 10^4$ per well in 12-well culture dishes and infected with recombinant adenovirus (AdCMVLacZ or AdCMVLuc) or adenovirus+Fab-FGF2 conjugate 24 hours later. The adenovirus and Fab-FGF2 conjugate were mixed in a volume of 130 μl at room temperature, and allowed to incubate for 30 minutes prior to infection of the cell monolayers. Cellular infections were carried out in a minimal volume (0.5 ml) of Optimem (Gibco BRL, Grand Island, N.Y.) for 2 hours at 37° C., then 5 ml of complete medium added.

The luciferase kit from Promega was used according to manufacturer's recommendations. Cells were lysed, and the cell lysates assayed for luciferase activity using a Berthold luminometer (Nashua, N.H.). Bradford protein assay was used to quantitate the protein in the samples. The data is reported as relative light units (RLU)/μg protein and is the average of 3 independent experiments.

EXAMPLE 14
Detection of Cytosine Deaminase Protein in AdCMVCD and AdCMVCD+Fab-FGF2 Infected Cells Five cell lines, SK-ChA-1, BXPC-3, Oz, CFPAC-1 and ASPC-1 were transfected as described with various MOI AdCMVCD and AdCMVCD+Fab-FGF2. Proteins were isolated from cells using Triton X-100 solubilization buffer (1% Triton X-100, 50 MM Hepes pH 7.5, 150 mM NaCl, 1.5 mM $MgCl_2$, 1 mM EDTA, 200 μM sodium orthovanadate, 10 mM sodium pyrophosphate, 100 mM sodium fluoride, 1 mM PMSF, 10% glycerol). Proteolytic inhibitors were added (aprotinin and leupeptin at a concentration of 10 μg/ml). The sample preparations with isolation buffer were incubated 10 minutes on ice, microfuged at 12,000×g for 15 minutes at 4° C., and the supernatant was collected.

Cytosine deaminase was separated by sodium dodecylsulphate-polyacrylamide gel electrophoresis (SDS-PAGE) as described by Laemmli and the samples were run under reducing conditions. Protein concentrations of the solubilized preparation were determined using the Pierce BCA protein assay kit and equal concentrations of total protein were loaded onto each lane of the gel. Rainbow colored protein weight markers (Amersham, Arlington Heights, Ill.) also were loaded onto one lane of each gel.

Proteins were electro-transferred to nitrocellulose membranes as described by Towbin et al. (36) for 12–15 hours at 0.1 amp and 1 hour at 1 amp. Membranes were placed in milk block buffer pH 7.5 (10% powdered mild, 0.02% Nonidet P-40, 0.15 M NaCl, 0.02 M Tris) overnight at 4° C. Membranes were then incubated overnight at 4° C. with a monoclonal antibody specific for CD (37) at 5 μg/ml. The blots were rinsed, and a goat anti-mouse IgG conjugated to alkaline phosphatase was added at a concentration of 0.5 μg/ml for 1 hour to bind the primary antibody. After rinsing, an alkaline phosphatase color development kit (BioRad, Hercules, Calif.) was used to visualize the antigen-antibody reaction.

EXAMPLE 15
In Vitro Evaluation of AdCMVCTD vs. AdCMVCD+Fab-FGF2 Mediated Cellular Cytotoxicity SK-ChA-1 and BXPC-3 cells were plated at $1.5 \times 10^6$ cells per well in 6-well plates and infected 24 hours later at a confluency of 80% with AdCMVLacZ, AdCMVCD or AdCMVCD+Fab-FGF2. Twenty-four hours later, cells were trypsinized, counted, and plated (5,000 cells/well) in 96-well microtiter plates (Costar) in 6 replicates. Media was supplemented with 5 μg/ml 5-FC (Sigma). Cell proliferation was determined by calorimetric assay (CellTiter 96 AQueous non-radioactive cell proliferation assay kit, Promega) after various periods of incubation. This assay measures the conversion of a tetrazolium salt (MTS) to formazan by viable cells. The absorbance at 490 nm was then measured in a 96-well plate reader (Molecular Devices, Menlo Park, Calif.). Data collected by the plate reader was analyzed by the SOFTmax software package (Emax Molecular Devices, Menlo Park, Calif.).

EXAMPLE 16
In Vitro Evaluation of Effectiveness of AdCMVCD vs. AdCMVCD+Fab-FGF2 Induction of CD Expression The relative expression of functional cytosine deaminase enzyme and its conversion of [6-$^3$H]-5-FC to [6-$^3$H]-5-FU was evaluated for cells infected with AdCMVCD or AdCMVCD+Fab-FGF2 using a modification of the procedure described by Haberkorn et al. (38). SK-ChA-1 or BXPC-3 cells were plated at $1.5 \times 10^6$ cells per well in 6-well plates (Costar) and infected 24 hours later at a confluency of 80% with AdCMVLacZ, AdCMVCD, and AdCMVCD+ Fab-FGF2 at various viral plaque forming units (pfu). Twenty-four hours later, cells were harvested and lysed by 4 freeze-thaw cycles in 100 mM Tris-HCl, 1 mM EDTA/ dithiothreitol (Sigma), pH 7.8. Cellular debris was pelleted by centrifugation at 14,000 rpm for 5 minutes. The cytosolic fraction was separated, and 6–10 μg of cytosolic protein was incubated with (0.5 μCi) [6-$^3$H]-5-FC (Sigma) at 37° C. for 6 hours. Each reaction mixture plus 5-FU and 5-FC standards were then spotted on a cellulose thin layer chromatography plate (Eastman Kodak, Rochester, N.Y.) and developed in a butanol-water chamber. Each region (5-FU and 5-FC) was visualized under UV light, and respective areas cut from the plate and placed in 5 ml EcoLume scintillation fluid (ICN, Costa Mesa, Calif.). Each region was counted for radioactivity in a Packard Tri-Carb 1900 TR liquid scintillation counter. The [$^3$H] gate (0–18.6 keV) was utilized, with a counting efficiency of 60%. Percent conversion of 5-FC to 5-FU was calculated as activity in the 5-FU fraction compared to the total counts in the 5-FC and 5-FU fractions for each treatment condition.

EXAMPLE 17
Evaluation of AdCMVCD vs. AdCMVCD+Fab'-FGF2 in Combination with 5-FC Prodrug Administration and External Beam Radiotherapy for Induction of Anti-Tumor Response in a Nude Mouse Model of BXPC-3 Pancreatic Carcinoma The utility of FGF2 retargeting of AdCMVCD for augmentation in efficacy of this approach was evaluated. Female athymic nude mice (National Cancer Institute Frederick Research Laboratory, Frederick, Md.) were injected s.c. with $2 \times 10^7$ BXPC-3 cells in 50 µl PBS in both flanks. Tumors with diameters of 7 to 10 mm developed in 7 days. On Day −2 relative to radiation treatment, right sided tumors were injected with AdCMVCD+Fab'-FGF2 at $2 \times 10^7$ pfu in a 50 µl volume, using a 27-gauge needle, and left sided tumors were injected with $2 \times 10^7$ pfu of AdCMVCD. Animals were administered 5-FC at 400 mg/kg twice daily by i.p. injection beginning on Day −2 relative to radiation and continuing for 7 days. On Day 0, animals were anesthetized with 2 mg ketamine (Phoenix Scientific Inc., St. Joseph, Mo.) by i.p. injection and treated with 5 Gy$^{60}$Co radiation (80 cGy/min) with a Picker C-9 80 cm isocenter clinical irradiator (Cleveland, Ohio). Tumor diameters were measured blinded with a Vernier caliper 3 times weekly and the surface area (product of length×width) calculated. Animals were maintained in a laminar flow room under sterile conditions and fed sterilized mouse chow and tap water in accordance with University of Alabama Animal Research guidelines.

EXAMPLE 18
Statistical Analysis

A two factor analysis of variance with interaction was used to assess the effects of AdCMVLuc and AdCMVLuc+Fab-FGF2 MOI on RLU for each of the cell types individually. Due to the nonconstant variability, the logarithm of RLU was analyzed. This transformation stabilized the variability and normalized the errors. A three-factor with interaction analysis of variance was used to assess the effects of MOI, virus type and day on the number of cells per well. Due to the nonconstant variability, the logarithm of cells per well was analyzed. This transformation stabilized the variability and normalized the errors. Global comparisons were done at the 5% significance level and all pairwise comparisons were done at the 1% significance level. A nonlinear model was used to calculate the 5-FU IC$_{50}$ for each cell type individually. The nonlinear model is given by: number of cells=trough+(peak−trough)/(1+dose/IC$_{50}$). To assess the correlation of the number of cells per well with 5-FU production, a simple linear regression was done modeling the logarithm of cells per well as a function of percent 5-FU production for each cell and virus type combination individually. Kaplan-Meier estimates on the difference in time to tumor size doubling was used to assess the difference in tumor growth in animals treated with AdCMVCD or AdCMVCD+Fab'-FGF2 plus 5-FC and radiation.

Figure 7A:
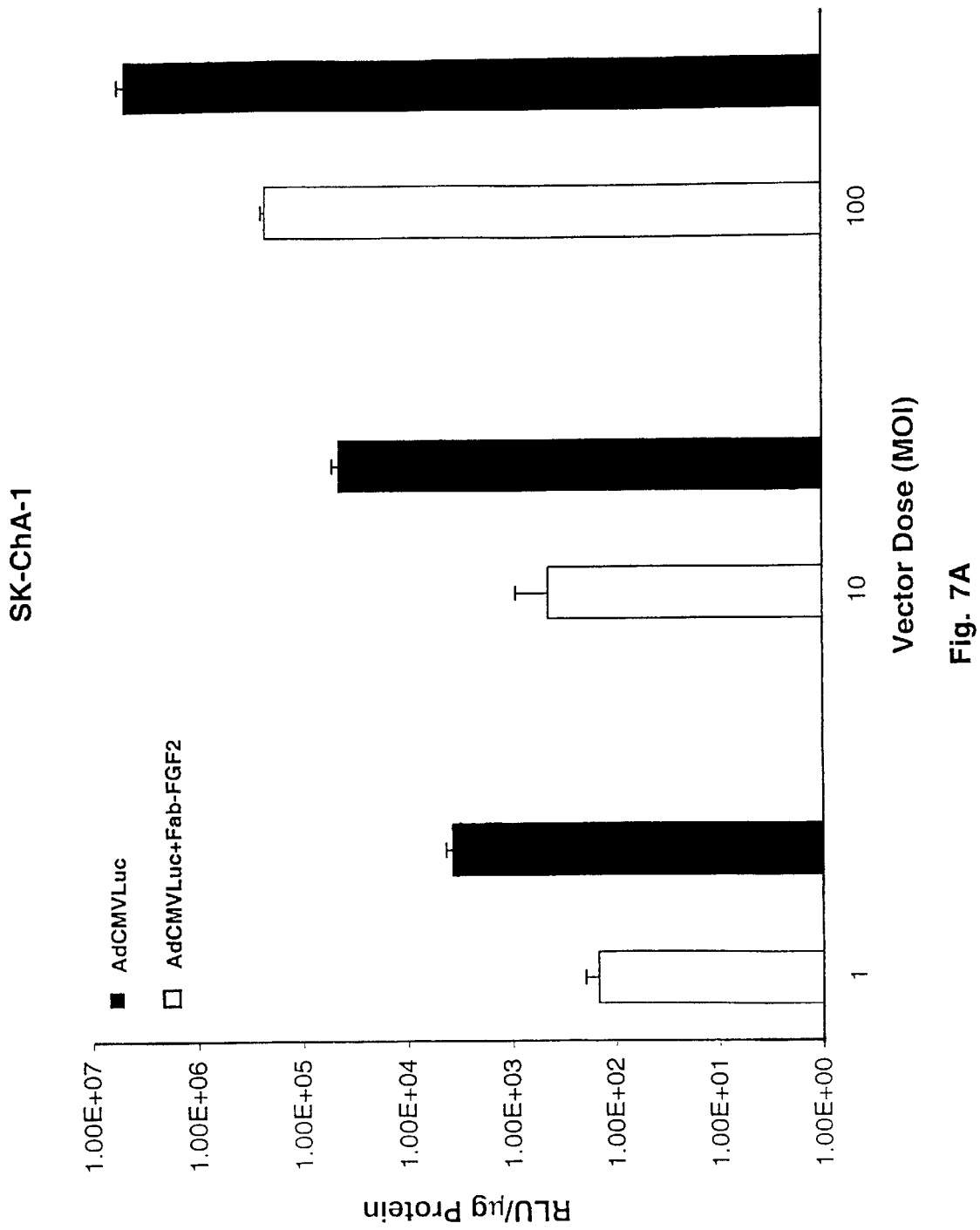
FIG. 7 shows differential luciferase expression in pancreatic and cholangiocarcinoma cells infected with AdCMV-Luc or FGF2-redirected AdCMVLuc adenoviral vector. SK-ChA-1 cholangiocarcinoma cells (FIG. 7A) and BXPC-3 cells (FIG. 7B) were infected with AdCMVLuc or AdCMVLuc+Fab-FGF2 to determine whether differential luciferase expression results from redirection with the Fab-FGF2 conjugate. Cells were infected with 1, 10 or 100 MOI at 37° C. for 2 hours, then complete media added to the plate. Twenty-four hours later, cell lysates were evaluated for luciferase activity. Fab-FGF2-retargeted AdCMVLuc resulted in increased levels of luciferase expression relative to AdCMVLuc alone.
Figure 7B:
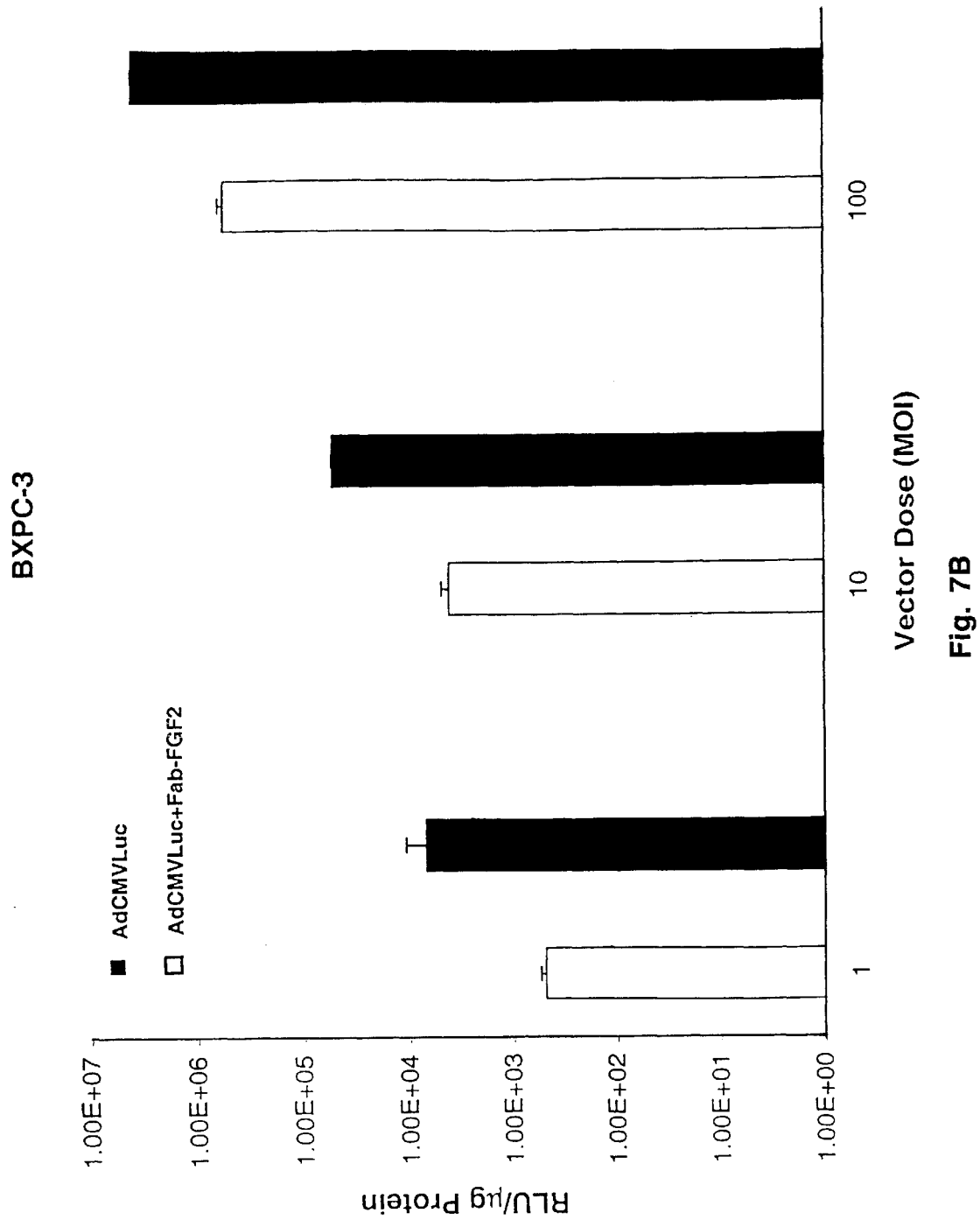

EXAMPLE 19
Determination of Firefly Luciferase Expression in Pancreatic and Cholangiocarcinoma Cells with a Redirected Adenoviral Vector Analysis of infectivity of SK-ChA-1 cholangiocarcinoma cells and BXPC-3 pancreatic carcinoma cells mediated by Fab-FGF2 redirection of AdCMVLuc was performed, and the results are shown (FIG. 7). SK-ChA-1 and BXPC-3 cells were transduced with 1, 10 and 100 MOI AdCMVLuc. An order of magnitude improvement in luciferase gene expression was observed with redirection of AdCMVLuc infection with Fab-FGF2 in SK-ChA-1 cholangiocarcinoma cells and BXPC-3 pancreatic carcinoma cells. This augmented gene delivery was blocked by pre-incubation of the conjugated virus with excess anti-FGF2 antibody. Thus, the results demonstrate increased adenovirus mediated gene delivery via the FGF2 ligand to these cells.

Figure 8A:
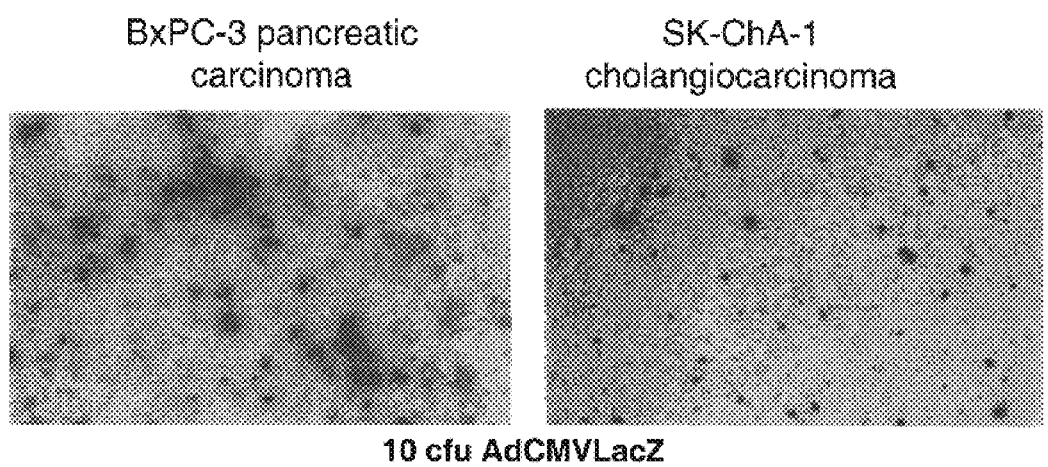
FIG. 8A shows BXPC-3 and SK-ChA-1 cells infected with AdCMVLacZ alone.
Figure 8B:
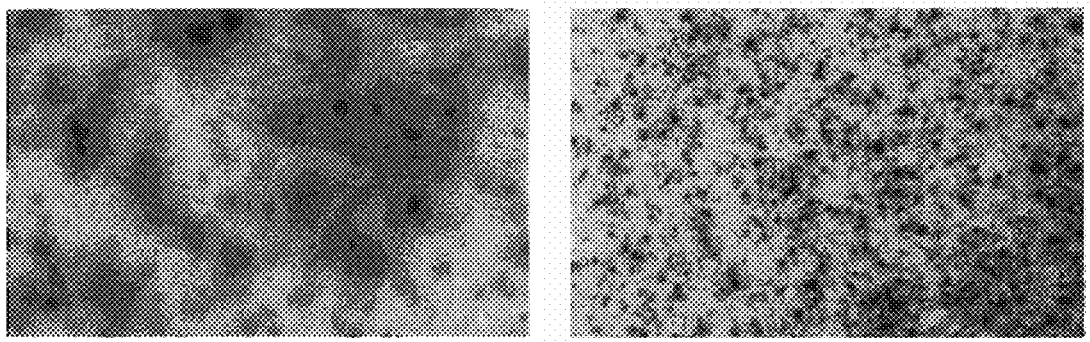
FIG. 8B shows BXPC-3 and SK-ChA-1 cells infected with AdCMVLacZ+Fab-FGF2. Redirection of AdCMVLacZ via the Fab-FGF2 moiety augmented the number of cells expressing β-galactosidase for both BXPC-3 and SK-ChA-1 cells.
Figure 9A:
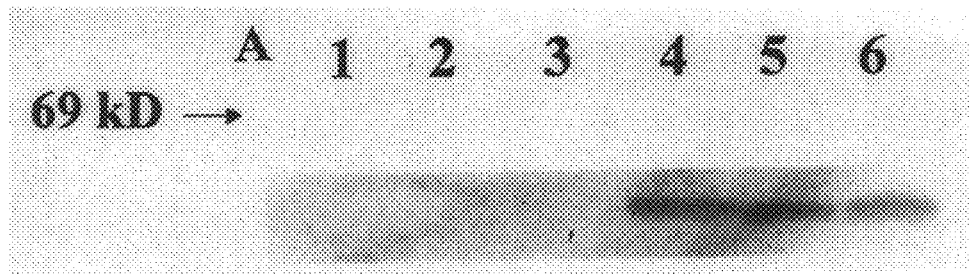
(FIG. 9A) Cell line SK-ChA-1: 1. 0 MOI (i.e., no transfection); 2. AdCMVLacZ-100 MOI; 3. 10 MOI; 4. 10R MOI; 5. 100 MOI; 6. 100R MOI.
Figure 9B:
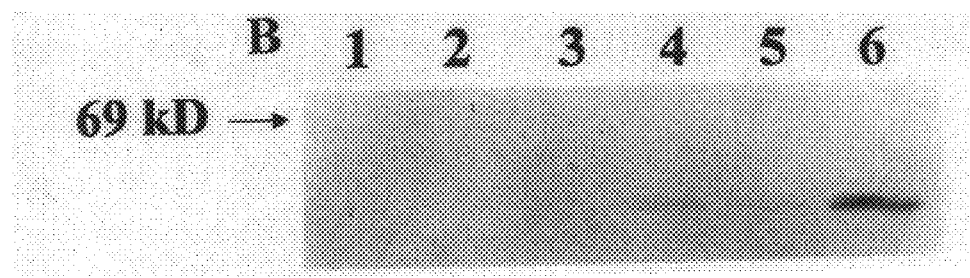
(FIG. 9B) Cell line BXPC-3: 1. 0 MOI; 2. AdCMVLacZ-10 MOI; 3. 1 MOI, 4. 1R MOI; 5. 10 MOI; 6. 10R MOI.
Figure 9C:
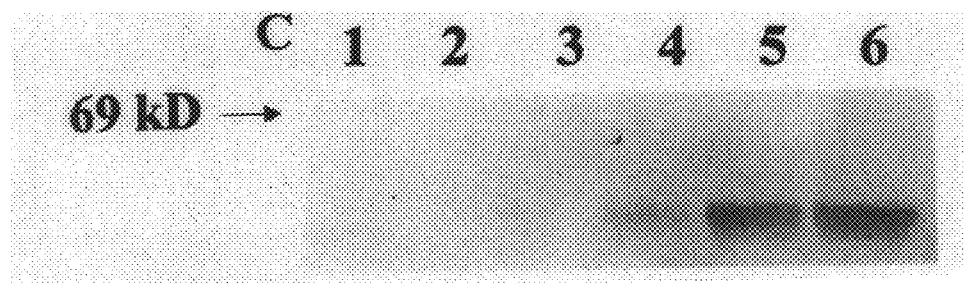
(FIG. 9C) Cell line Oz: 1. 0 MOI; 2. AdCMVLacZ-100 MOI; 3. 10 MOI; 4. 10R MOI; 5. 100 MOI; 6. 100R MOI.
Figure 9D:
(FIG. 9D) Cell line CFPAC-1; 1. 0 MOI; 2. AdCMVLacZ-500 MOI; 3. 100 MOI; 4. 100R MOI; 5. 500 MOI, 6. 500R MOI.
Figure 9E:
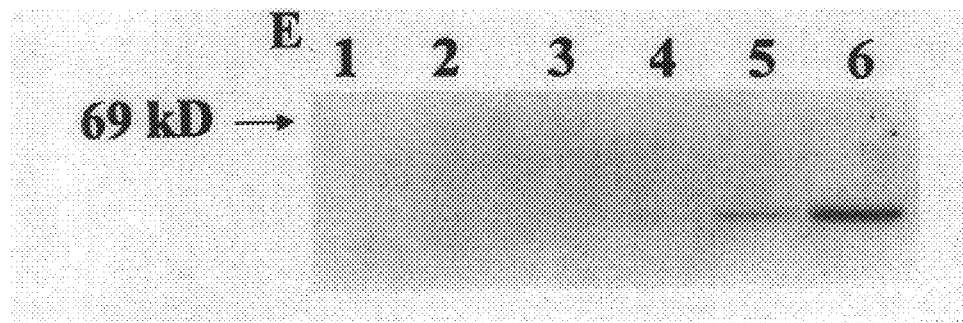
(FIG. 9E) Cell line ASPC-1; 1. 0 MOI; 2. AdCMVLacZ-100 MOI; 3. 10 MOI; 4. 10R MOI; 5. 100 MOI; 6. 100R MOI. In all cell lines, the retargeted transfection (R) with AdCMVCD+Fab-FGF2 resulted in a greater cellular concentration of CD than AdCMVCD at equivalent MOIs tested. In addition, except for the cell line SK-ChA-1 (gel A), retargeting via Fab-FGF2 induced greater CD protein with higher MOIs.

EXAMPLE 20
Determination of *E. coli* β-galactosidase Expression in Pancreatic and Cholangiocarcinoma Cells with a Redirected Adenoviral Vector An analysis was undertaken to visually demonstrate differential β-galactosidase expression in BXPC-3 and SK-ChA-1 cells following infection with AdCMVLacZ and AdCMVLacZ+Fab-FGF2 (FIG. 8). X-gal staining of both cell types indicated improved transduction efficiency of cells when AdCMVLacZ infection was redirected via Fab-FGF2. LacZ gene expression was inhibited by pre-incubation of BXPC-3 and SK-ChA-1 cells with 25 µg heparin. This improved redirected transduction efficiency of cells correlated with greater luciferase gene expression (FIG. 7).

EXAMPLE 21
5-FU Cytotoxicity to Pancreatic and Cholangiocarcinoma Cell Lines To determine the relative sensitivity of several hepatobiliary cell lines to 5-FU, the concentration of 5-FU which inhibited cellular growth by 50% (IC$_{50}$) was determined. Characterization of this information is particularly relevant to the CD/5-FC toxin gene prodrug system, as 5-FU is the toxic metabolic product of cytosine deaminase enzymatic conversion of 5-FC. The most 5-FU sensitive cell lines were CFPAC-1 and SK-ChA-1 with IC$_{50}$ values of 0.089 µg/ml and 0.115 µg/ml, respectively. BXPC-3 and ASPC-1 were less sensitive with IC$_{50}$ values of 0.134 µg/ml and 0.635 µg/ml, respectively. Thus, these results indicate that for equivalent levels of cytosine deaminase gene transfer, the various cell lines should show a differential level of 5-FU mediated cytotoxicity.

EXAMPLE 22
Determination of Differential Expression of Cytosine Deaminase in AdCMVCD and AdCMVCD+Fab-FGF2 Infected Pancreatic and Cholangiocarcinoma Cells Western blotting of cell lines transfected at various MOIs demonstrated that in all cell lines, the retargeted transfection with AdCMVCD+Fab-FGF2 resulted in a greater cellular concentration of cytosine deaminase protein than transfection with AdCMVCD alone (FIG. 9). At a higher MOI in SK-ChA-1 (FIG. 9, gel A), retargeting also generated a greater concentration of cytosine deaminase protein.

Figure 10A:
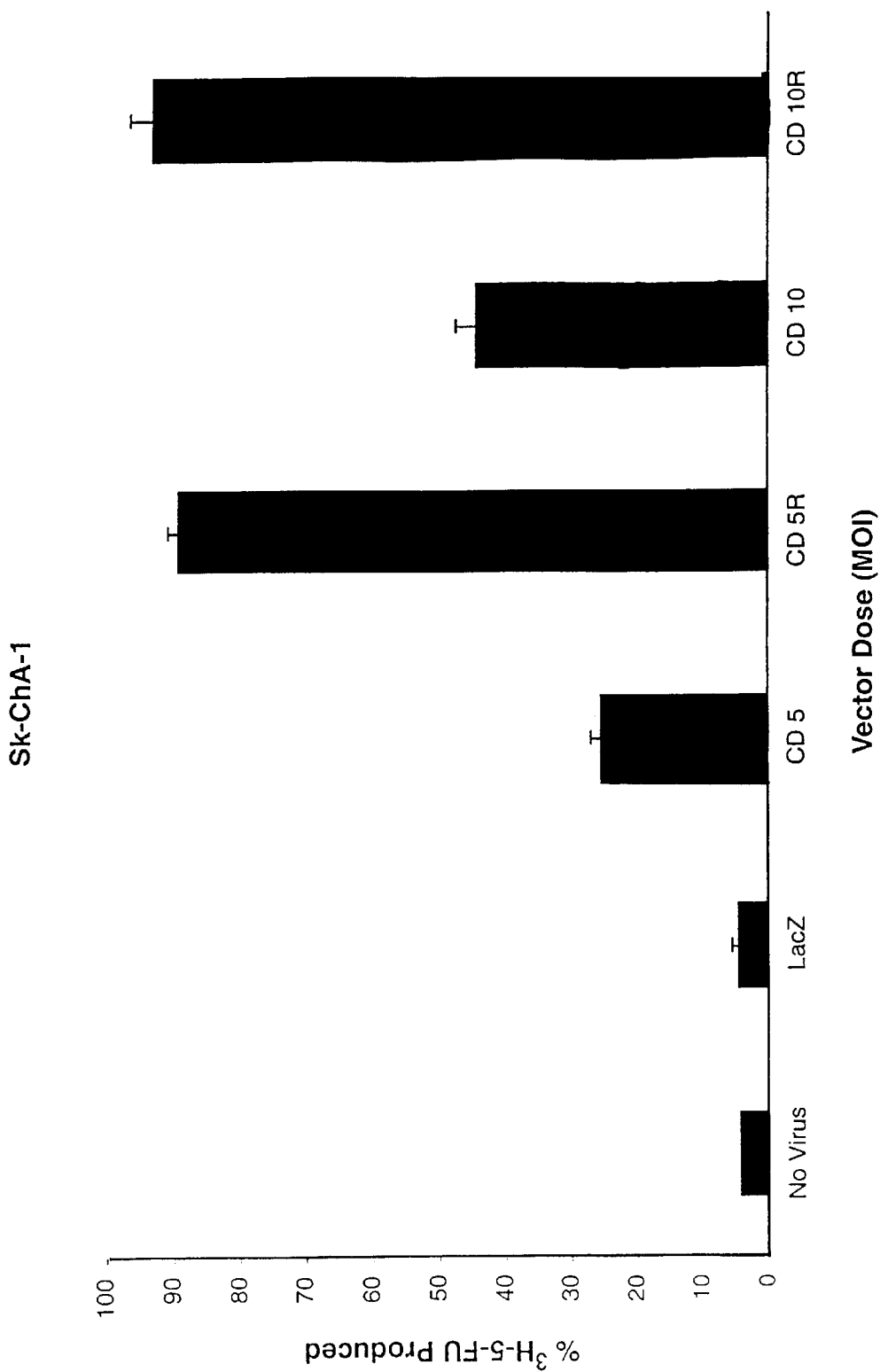
FIG. 10 shows CD mediated conversion of 5-FC to 5-FU in pancreatic and cholangiocarcinoma cells. SK-ChA-1 (FIG. 10A), BXPC-3 (FIG. 10B) or CFPAC-1 (FIG. 10C) cells were infected with AdCMVCD or AdCMVCD+Fab-FGF2 at various MOI. Cells were harvested and lysed and 6–10 μg protein was incubated with [6-$^3$H]-5-FC at 37° C. for 6 hours. Each reaction mixture plus 5-FU and 5-FC standards were then spotted on a cellulose thin layer chromatography plate. Each region (5-FU and 5-FC) was counted for radioactivity. Percent conversion of 5-FC to 5-FU was calculated as activity in the 5-FU fraction compared to the total counts in the 5-FC and 5-FU fractions. Controls included uninfected cells and AdCMVLacZ infected cells.
Figure 10B:
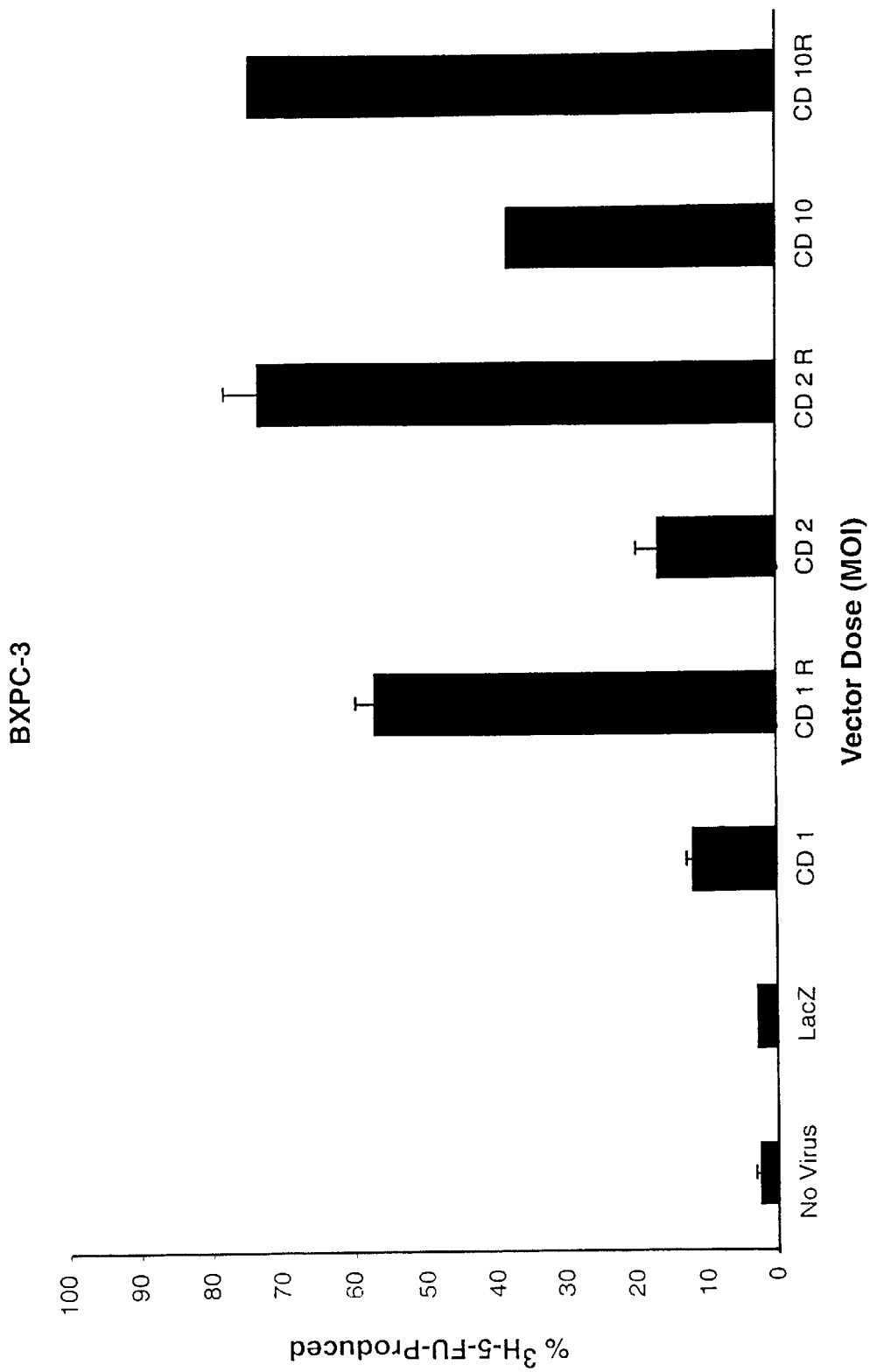

EXAMPLE 23
Differential Cytosine Deaminase Function in Pancreatic and Cholangiocarcinoma Cells Based upon FGF2 Redirection The relative conversion of 5-FC into 5-FU for selected hepatobiliary cell lines infected with AdCMVCD or AdCMVCD+Fab-FGF2 is shown (FIG. 10). The highest $^3$H-5-FC conversion to $^3$H-5-FU after cellular infection with 10 MOI of AdCMVCD was seen in SK-ChA-1 (44.4%), and BXPC-3 (38.4%) cells. A lower level of conversion was seen in CFPAC-1 (6.4%) pancreatic carcinoma cells. When AdCMVCD infection was redirected by pre-incubation with Fab-FGF2, higher levels of CD enzymatic activity were observed at 10 MOI for SK-ChA-1 cells (93.5%) and BXPC-3 cells (74.8%). Similar trends were noted at 5 MOI in SK-ChA-1 cells and 1 or 2 MOI in BXPC-3 cells. For CFPAC-1 cells, increased 5-FU production via Fab-FGF2 redirection of AdCMVCD was seen in the 100 MOI group (66.9%). Cytosine deaminase mediated conversion of $^3$H-5-FC into $^3$H-5-FU was inhibited to less than 10% when AdCMVCD+Fab-FGF2 was preincubated with 25 μg heparin. Control conditions of no viral infection or control AdCMVLacZ viral infection did not result in 5-FU production, and had background levels of radioactivity (<10%). Thus, the level of 5-FC to 5-FU conversion following adenoviral retargeting compared to native adenovirus was highest at low MOI in SK-ChA-1 and BXPC-3 cell lines, while the 5-FC to 5-FU conversion rate in CFPAC-1 cells following adenoviral retargeting was high only at high MOI.

Figure 11A:
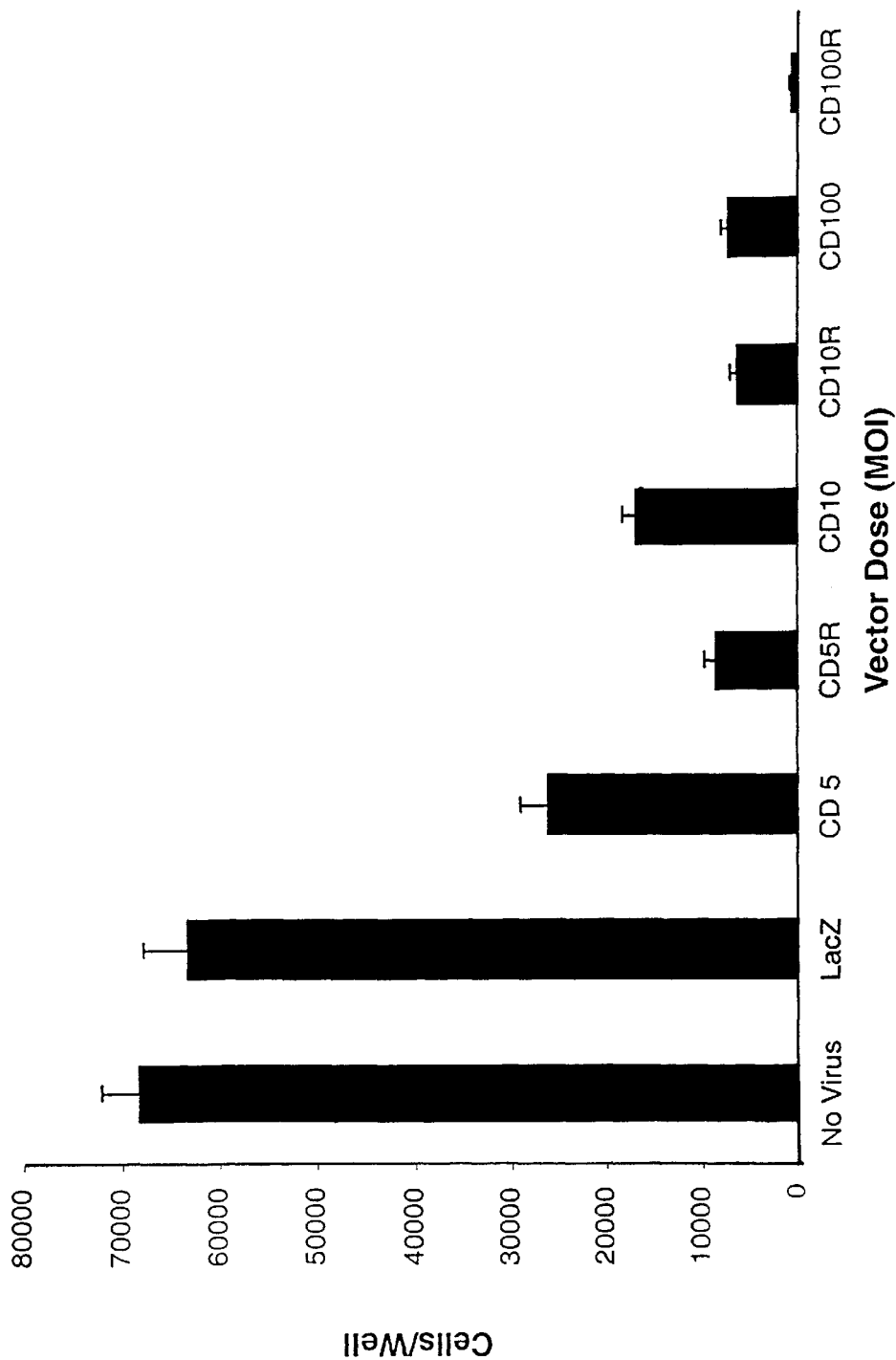
FIG. 11 shows CD mediated cytotoxicity to pancreatic and cholangiocarcinoma cells following infection with AdCMVCD or AdCMVCD+Fab-FGF2. SK-ChA-1 (FIG. 11A), BXPC-3 (FIG. 11B) or CFPAC-1 (FIG. 11C) cells were infected at a confluency of 80% with AdCMVCD or AdCMVCD+Fab-FGF2. Controls included AdCMVLacZ or no virus. Twenty-four hours later, cells were trypsinized, counted and plated in 96-well plates with media containing 5 μg/ml 5-FC. Cell proliferation was determined by tetrazolium salt (MTS) colorimetric assay after 6–8 days of incubation.
Figure 11B:
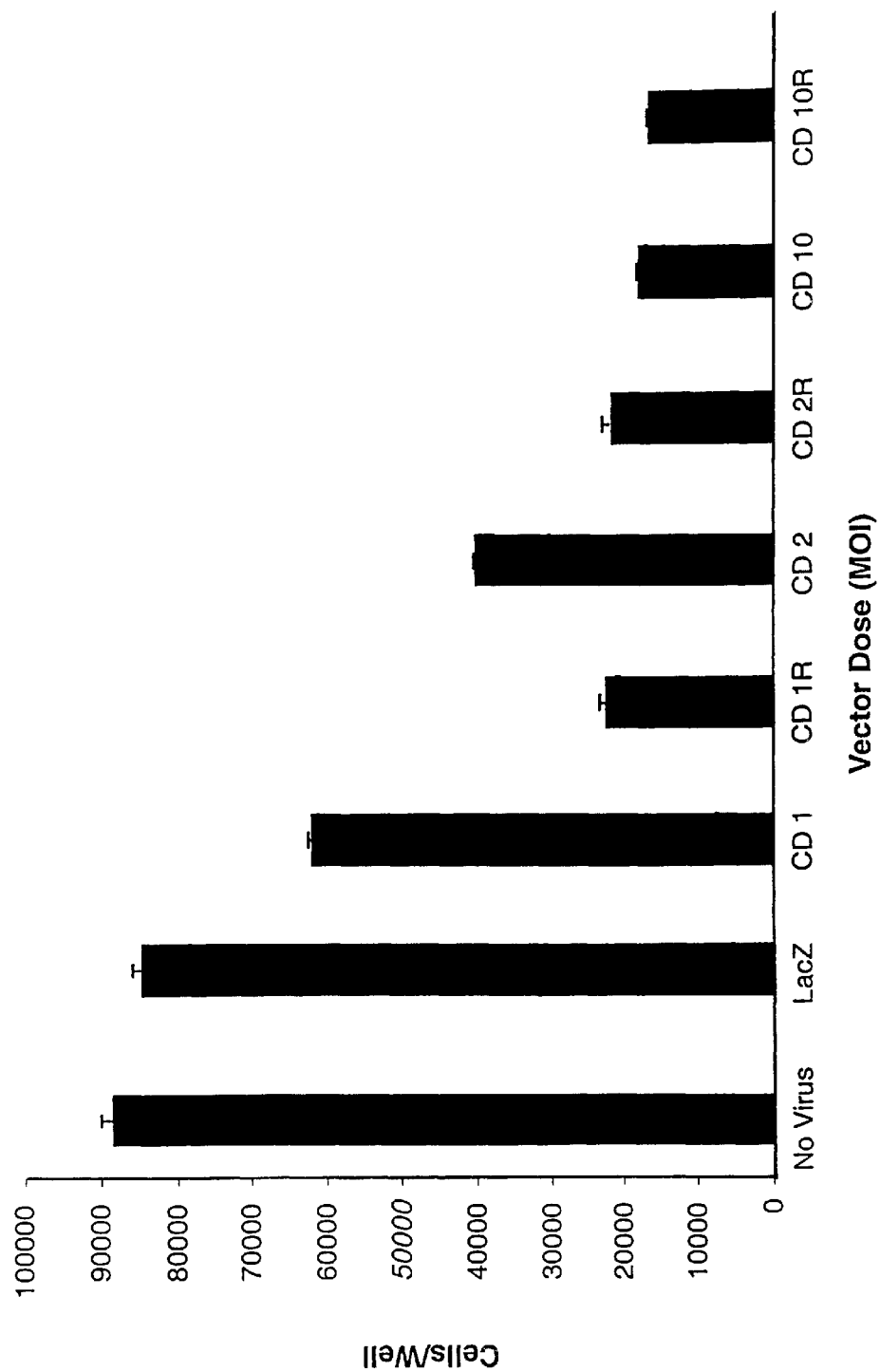
Figure 11C:
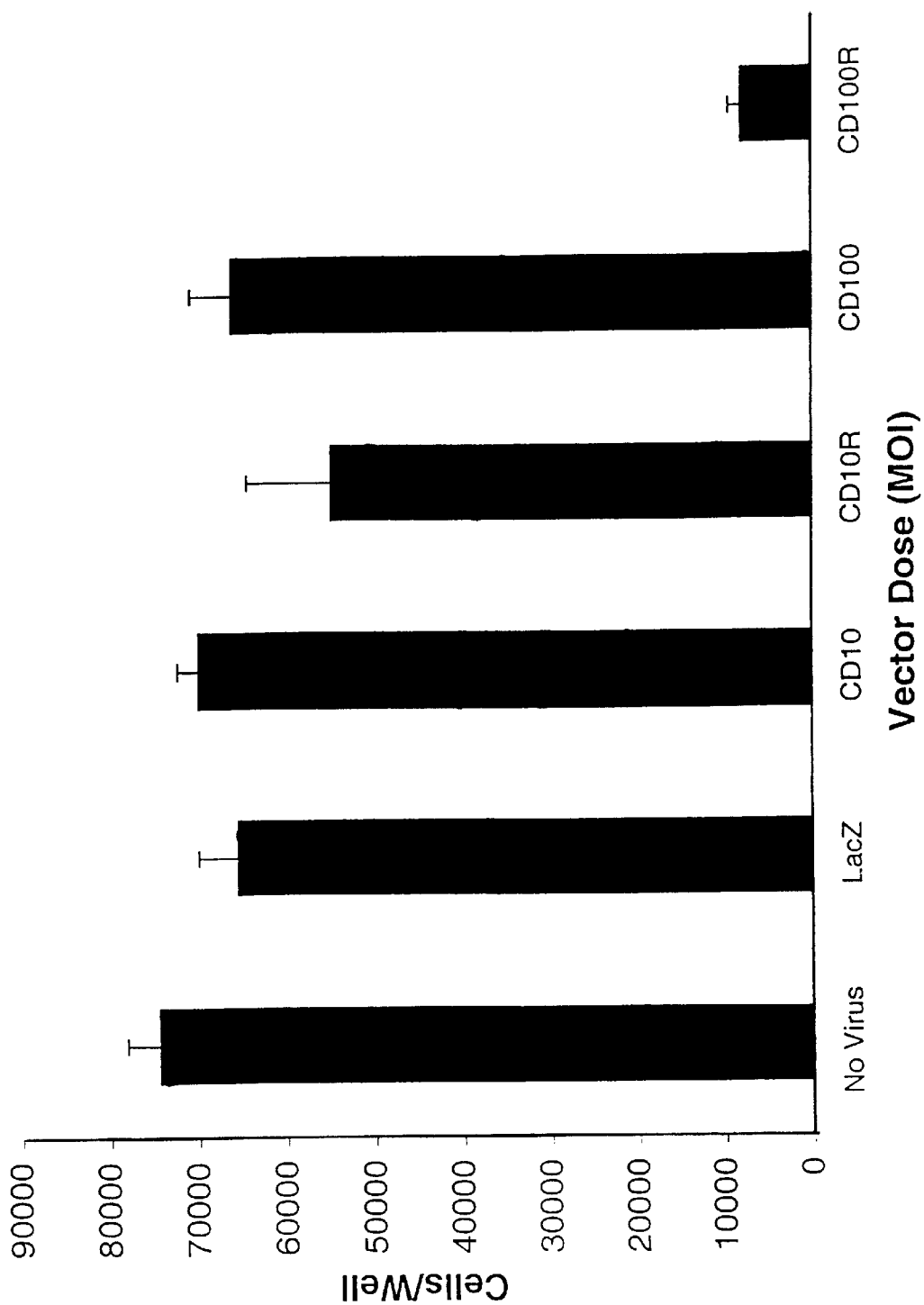

EXAMPLE 24
Determination of Differential Cytotoxicity in Pancreatic and Cholangiocarcinoma Cells Based Upon FGF2 Redirection of AdCMVCD The ability of adenoviral vector redirection to enhance the sensitivity of tumors in the context of the CD/5-FC approach was evaluated. Cytotoxicity to hepatobiliary cells transduced by AdCMVCD or AdCMVCD+Fab-FGF2 and exposed to 5 μg/ml 5-FC is shown (FIG. 11). The greatest cytotoxic effects of AdCMVCD (10 MOI) were observed in SK-ChA-1 and BXPC-3 cells. These results are consistent with the 5-FU production data (FIG. 10). SK-ChA-1 cells infected with 5, 10, or 100 MOI AdCMVCD and exposed to 5-FC for 7 days had 41.4%, 26.8% and 11.7% of cells/well relative to cells infected with 100 MOI AdCMVLacZ and exposed to 5-FC for 7 days (FIG. 11A). BXPC-3 cells infected with 1, 2, or 10 MOI AdCMVCD and exposed to 5-FC for 6 days had 73.3%, 47.7% and 19.9% of cells/well relative to cells infected with 100 MOI AdCMVLacZ and exposed to 5-FC for 6 days (FIG. 11B).

No increase in cytotoxicity was observed in the CFPAC-1 cells with increasing MOI of AdCMVCD from 5 to 100. The cell lines which converted significant amounts of 5-FC into 5-FU, had the greatest cytotoxicity following infection with AdCMVCD and exposure to 5 μg/ml 5-FC.

Cytotoxic effects induced by AdCMVCD were enhanced by pre-incubation of AdCMVCD with Fab-FGF2 prior to infection of the cells. SK-ChA-1 cells infected with 5, 10 and 100 MOI AdCMVCD+Fab-FGF2 and exposed to 5-FC for 7 days (FIG. 11A) had significantly more toxicity relative to cells infected with 5, 10 and 100 MOI AdCMVCD and exposed to 5-FC for 7 days (p=0.0001, 0.0001 and 0.0001, respectively). In BXPC-3 cells following infection with 10 or 100 MOI of AdCMVCD+Fab-FGF2 compared to AdCMVCD, retargeting with Fab-FGF2 did not result in differential cytotoxicity. The overall level of cell killing was significantly greater than no treatment controls. As BXPC-3 cells were shown to be relatively sensitive to 5-FU mediated killing with an $IC_{50}$ value of 0.134 μg/ml, the dose of AdCMVCD was decreased to 1 and 2 MOI in these cells. BXPC-3 cells transduced at these lower MOIs resulted in a differential cytotoxic effect between AdCMVCD and AdCMVCD+Fab-FGF2 infected BXPC-3 cells (p=0.0001) (FIG. 11B). In contrast, CFPAC-1 cells which did not readily convert 5-FC to 5-FU, showed induction of cytotoxicity only at 100 MOI AdCMVCD+Fab-FGF2 (p=0.0001). This data correlates with 5-FU production data (FIG. 10C).

Figure 12:
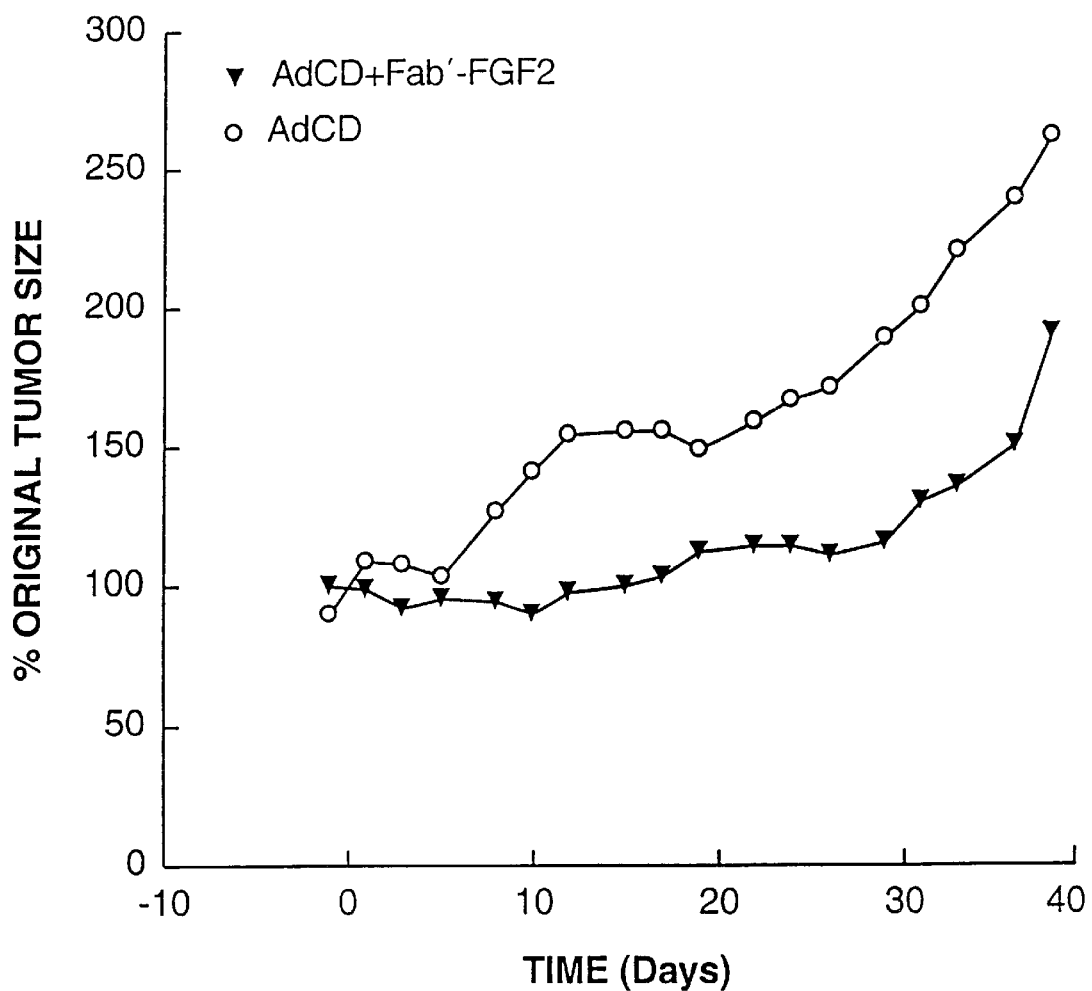
FIG. 12 shows growth of BXPC-3 tumors following treatment with AdCMVCD or AdCMVCD+Fab'-FGF2, 5-FC, and 5 Gy radiation. Mice received 2×10$^7$ BXPC-3 cells by s.c. injection, and tumors with diameters of 5 to 10 mm formed in 7 days. At this time, AdCMVCD or AdCMVCD+Fab'-FGF2 (5×10$^7$ pfu) was administered by intratumoral injection on Day −2 relative to radiation treatment. All animals received 5-FC (400 mg/kg twice daily by i. p. injection) beginning on Day −2 for 7 days. Animals received 5 Gy $^{60}$Co (Day 0) to their tumor. Data points represent the mean change in tumor surface area relative to Day 0. n=5 tumors/group.

EXAMPLE 25
In Vivo Determination of Therapeutic Efficacy of Multimodality Therapy for Pancreatic Tumors Utilizing Fab'-FGF2 Redirected AdCMVCD, 5-FC Administration, and External Beam Radiotherapy For BXPC-3 tumors injected with AdCMVCD+Fab'-FGF2, systemic 5-FC, and external beam radiotherapy, the time to tumor doubling was extended compared to tumors injected with AdCMVCD, systemic 5-FC, and external beam radiotherapy (FIG. 12). Based on the 95% confidence interval, adenoviral retargeting extended the time to tumor doubling by 1 to 28 days.

EXAMPLE 26
Tumor Cell Conversion of 5-FC to 5-FU via MRS Over Time in Human Pancreatic and Colon Cancer Cells both in vitro and in vivo In vitro models of molecular chemotherapy were developed using the AdCMVCD cytosine deaminase toxin gene for the transfection of both human pancreatic and colon cancer cell lines (BXPC-3, WiDR, LS174T). These lines when transfected with the AdCMVCD have demonstrated >75–80% cytotoxicity after the addition of 5-FC to the media. In this study, an in vitro treatment model was proposed using 3×10$^6$ BXPC-3 pancreatic tumor cells transfected at a MOI of 100 with AdCMVCD. These cells were then examined by MRS at 0, 2, 6 and 24 hours for conversion of 5-FC to 5-FU.

Initial studies have shown the sensitivity of fluorine spectroscopy by its ability to detect 3.8 mM 5-FC when initially added to transfected BXPC-3 cells. Initial data shows that after 90 minutes, no significant change in signal intensity of the 5-FC was identified with minimal 5-FU detected. However, after 120 minutes, the signal for 5-FC had dropped to 50% of its original intensity and the signal for 5-FU had increased to approximately 40% of the original 5-FC signal indicating conversion of 5-FC to 5-FU.

EXAMPLE 27
Optimize the Conditions to Achieve Prolonged Maximal Production of 5-FU in Mouse Tumor Models Monitored by MRS MRS was used to optimize the prodrug approach using mouse tumor models. Metastatic hepatic tumor models of colon and pancreatic cancer were developed. Special delivery procedures for adenovirus and the delivery of the prodrug were proposed. Pancreatic and colon tumors were grown both subcutaneously and in the liver following intrasplenic injection and the tumors were transduced with cytosine deaminase containing adenovirus. The adenovirus will be targeted to the tumors in the liver via basic fibroblast growth factor. The animals and tumors will then be subjected to varying dosing schedules of the prodrug, to varying amounts of radiation and to multiple doses of the adenovirus. MRS allows a continuous in vivo detection system for 5-FU during these treatment conditions in the same animal over time. Through this, each mouse will be monitored over time and the pharmacokinetics measured of the prodrug 5-FC, the active drug 5-FU, along with monitoring which combination of procedures produces the greatest inhibition of tumor growth. It is expected that the use of MRS can help maximize the tumoricidal properties of CD/5-FC gene therapy and that planned human trials will also incorporate MRS into the experimental design and will directly benefit from this improved efficacy.

Figure 13:
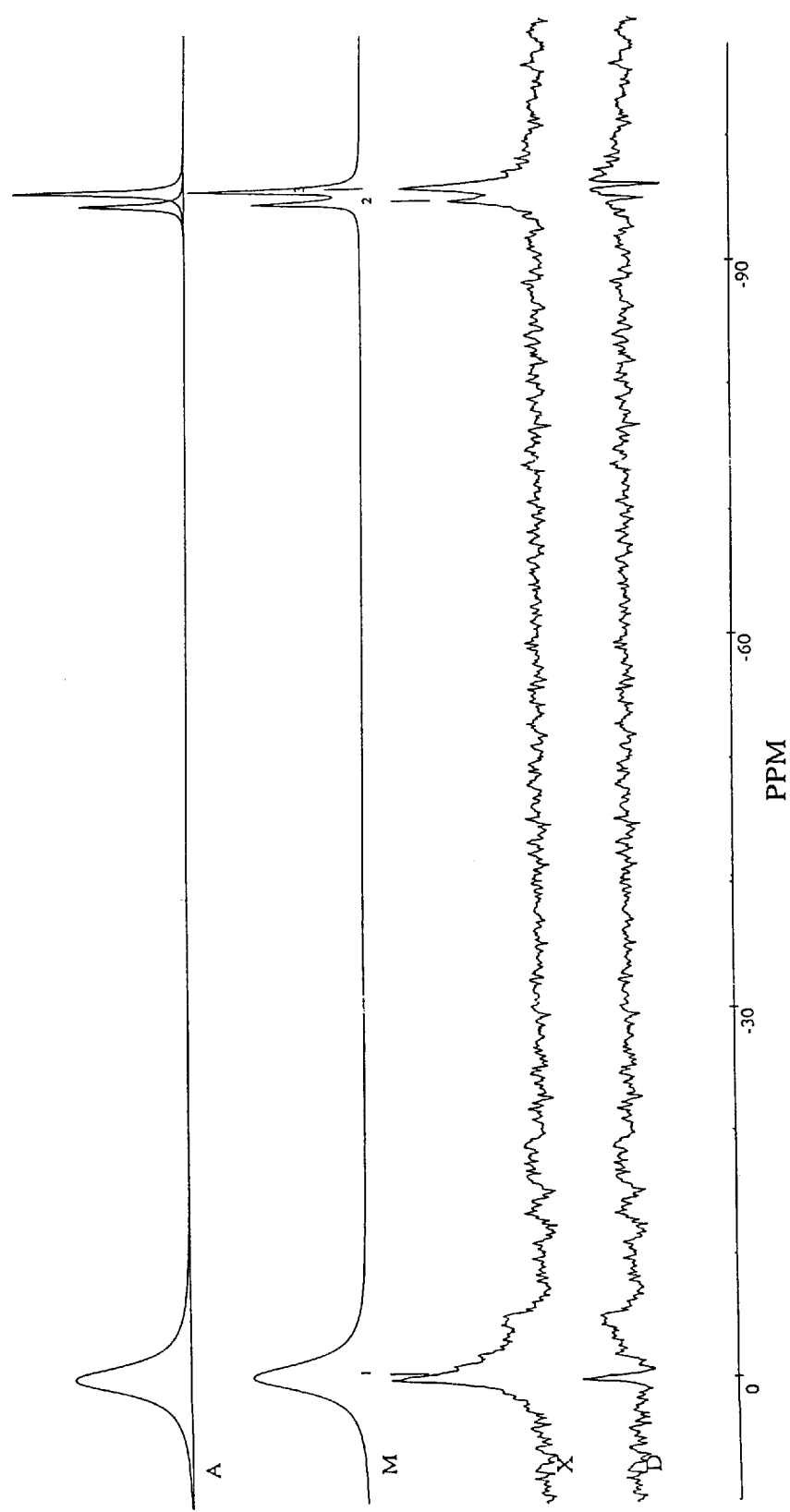
FIG. 13 shows a significant peak for 5-FU at the initial time point when evaluated by MRS. 2×10$^7$ LS174T cells transfected at a MOI of 100 with AdCMVCD were injected into a subcutaneous area in the flank of a nude mouse. Locally, approximately 50 microliters of 3.8 mM 5-FC were injected at the site of the tumor after which these animals were placed in the magnet and evaluated for the presence of 5-FC and the conversion of 5-FC to 5-FU by the adenoviral cytosine deaminase gene.
Figure 14:
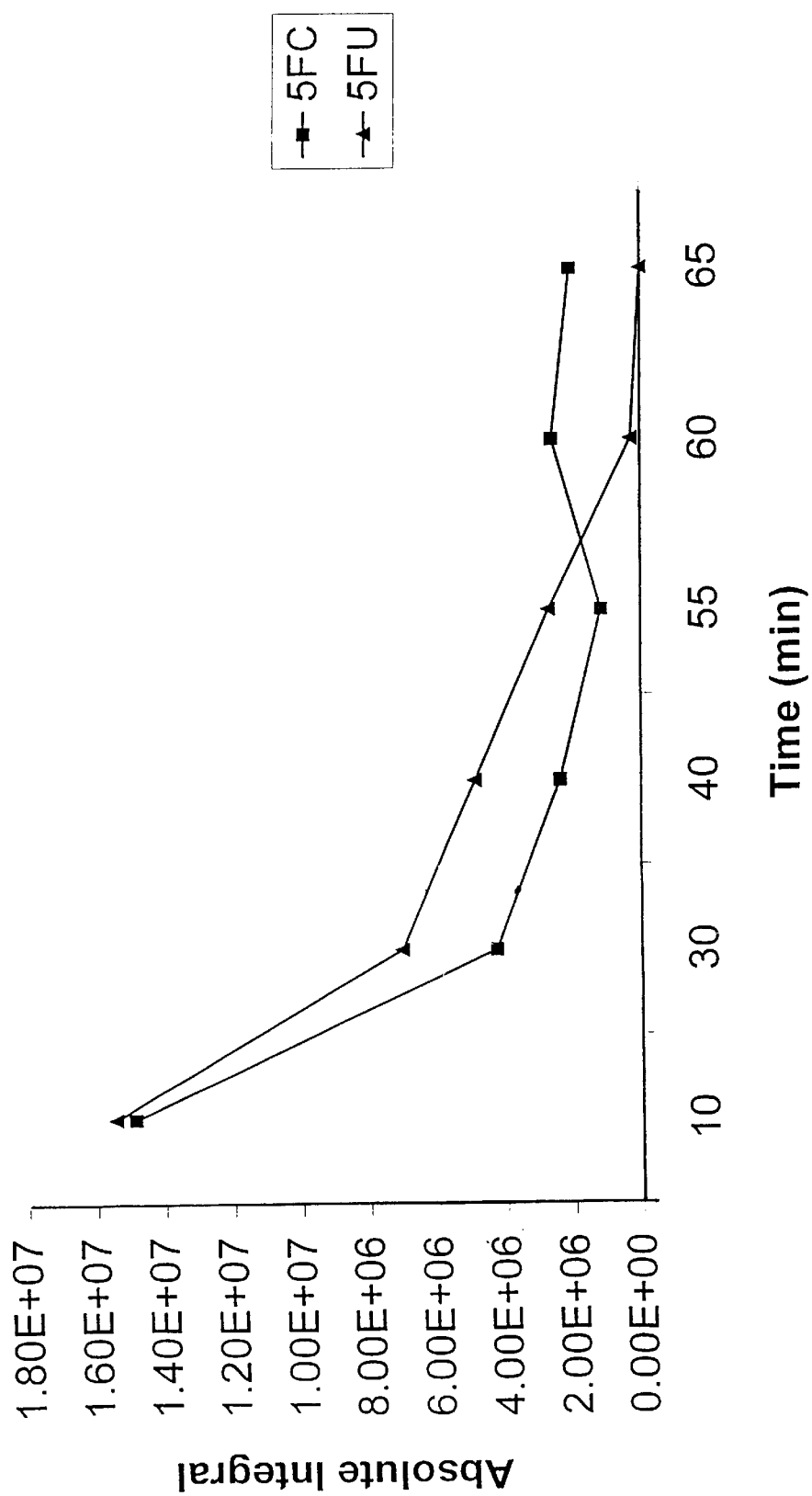
FIG. 14 shows that the integral of the 5-FU peak exceeded that of the 5-FC peak for 55 minutes. The experimental procedure is the same as that in FIG. 13.

In vivo model: $2 \times 10^7$ LS174T cells transfected at a MOI of 100 with AdCMVCD were injected into a subcutaneous area in the flank of a nude mouse. Locally, approximately 50 microliters of 3.8 mM 5-FC was injected at the site of the tumor after which these animals were placed in the magnet and evaluated for the presence of 5-FC and the conversion of 5-FC to 5-FU by the adenoviral cytosine deaminase gene. The results demonstrate that the initial time point evaluated was at 10 minutes at which there was a significant peak for 5-FU (FIG. 13). The integral of the 5-FU peak exceeded that of the 5-FC peak for 55 minutes (FIG. 14).

EXAMPLE 28

Correlate the Levels of 5-FU Produced with Therapeutic Outcome in Tumors Treated with Cytosine Deaminase Encoding Adenovirus, 5-FC and Radiation Therapy Therapy studies will be performed concurrently with the imaging studies described in Example 27. The results obtained will demonstrate the correlation between 5-FU production in the tumor and the therapeutic efficacy of the therapy protocol.

The enhancement of gene expression in pancreatic and cholangiocarcinoma cell lines was augmented 10–100 times with the Fab-FGF2 redirected virus, and was blocked by an excess of FGF2 and by free heparin sulfate. As shown by Goldman et al. (39), there was enhancement of cellular transduction mediated by Fab-FGF2 redirection of adenoviral infection in human Kaposi's sarcoma (KS) cells (39). To attempt to distinguish whether the enhanced luciferase gene expression was due to increased gene expression within each cell, or to enhanced transduction efficiency of the AdCMVCD+Fab-FGF2 conjugated virus, redirection experiments with AdCMVLacZ were performed. In vitro, the transduction efficiency of SK-ChA-1 and BXPC-3 cells was substantially improved by the Fab-FGF2 moiety (FIG. 8), indicating that significantly greater number of cells were transduced with the redirected virus.

An objective of the present invention was to demonstrate that cytosine deaminase mediated cytotoxicity was enhanced by Fab-FGF2 redirection resulting in greater cytotoxicity. At low viral MOIs in SK-ChA-1 and BXPC-3 cells, there was significantly increased cytosine deaminase gene function measured by conversion of 5-FC into 5-FU, and induction of cytotoxicity. The CFPAC-1 cell line did not demonstrate the degree of enhanced 5-FU production or induction of cytotoxicity with redirected AdCMVCD at low MOIs. Cytotoxicity was only seen with the Fab-FGF2 retargeted virus at high viral doses. This has important implications to treatment of in situ tumors in a clinical setting, as the effectiveness of a single vector administration may be substantially improved. The in vivo experiments indicated that in a multimodality therapy model of human pancreatic cancer, the Fab'-FGF2 redirected AdCMVCD resulted in enhanced tumor growth inhibition compared to native virus alone.

These observations have clear importance in clinical gene therapy applications. Methodologies to enhance the therapeutic effect of the first dose of vector are very important, as many studies have shown decreasing effectiveness of repeat adenoviral vector administration. Additionally, limited clinical experience indicates that multi-modality therapy incorporating neoadjuvant 5-FU chemotherapy and radiation therapy may improve treatment for other refractory malignancies (e.g. rectal or rectosigmoid). Improved treatment of established human tumors is a clinically important goal as patients with both cholangiocarcinoma and pancreatic carcinoma generally present with advanced disease, refractory to current treatment. The present invention indicates a n improved tumor response to therapy with AdCMVCD+Fab'-FGF2 compared to AdCMVCD alone in combination with 5-FC treatment and external beam radiotherapy. These results demonstrate that the retargeted AdCMVCD in conjunction with systemic 5-FC administration and external beam radiotherapy was more efficacious in treating established pancreatic tumors in vivo. Thus, this finding validates the efficacy of FGF2-retargeting with this therapeutic gene and a human interventional trial.

In conclusion, the enhanced gene delivery obtained in hepatobiliary cancer cells with the Fab-FGF2 redirected adenoviruses translated into enhanced cytotoxicity to pancreatic and cholangiocarcinoma cells utilizing the CD/5-FC toxin gene prodrug system both in vitro and in vivo. These findings provide the rationale for investigating such tropism modified adenoviruses in a clinical setting.

The preliminary data of continuous monitoring conversion of 5-FC to 5-FU via MRS confirm the possibility of detecting the conversion of 5-FC to 5-FU in both an in vitro and in vivo setting. Future studies involves in vivo pancreatic and colon tumor models to evaluate the efficacy of AdCMVCD with and without radiation (5×3 Gy fractions) in the treatment of pancreatic and colon tumor correlated to the conversion of 5-FC to 5-FU detected by MRS. Conversion studies will for the first time allow the use of a noninvasive method to evaluate the role of gene therapy in the treatment of a lethal tumor by determining intratumoral levels of 5-FU as it is converted from 5-FC via the cytosine deaminase gene. Alternate adenoviral, 5-FC and radiation delivery schedules will be devised based on the data obtained from the initial optimization study. These studies will also provide the basis for development of further subcutaneous and liver metastatic models which will allow for the combined treatment of 5-FU and radiation along with noninvasive detection using MRS. The long term goal of these studies is application to the clinical setting for the detection of intratumoral 5-FU established through molecular chemotherapy.

EXAMPLE 30

Sensitivity of Glioma Cells to 5-fluorouracil

Systemically administered 5-fluorouracil (5-FU) (70, 71) is the mainstay for chemotherapy of several malignancies, particularly colon, pancreatic and other carcinomas of the gastrointestinal (GI) tract. 5-fluorouracil has also been investigated both in vitro and in vivo for glioma chemotherapy (85–87). However, 5-fluorouracil is not routinely used in patients with gliomas, and pharmacokinetic factors, systemic toxicity, and tumor sensitivity have limited its use with other non-gastrointestinal tumors as well. To determine if glioma cells are sensitive to 5-fluorouracil if it is directly administered to the cells, the in vitro toxicity of 5-FU to 4 human glioma cell lines was examined. Two human colon (LS174T, WiDR) and two pancreatic (AsPC-1, BxPC-3) carcinoma cell lines were included as references.

Tumor cells ($5 \times 10^4$) were plated in 96 well plates and allowed to adhere overnight. Cells were then incubated continuously in the presence of increasing concentrations of 5-FU (0–200 μg/ml) and assayed for toxicity using an MTS assay (Promega, Madison Wis.) after 5-days. $IC_x$ values were calculated as previously described (82). U251MG glioma cells were as sensitive to 5-FU as LS174T and WiDR colon carcinoma cells, while D54MG, U87MG and U118MG glioma cells and AsPC-1 pancreatic carcinoma cells were 3-fold less sensitive (Table 2).

TABLE 2

Sensitivity of human tumor cell lines to 5-FU in vitro

| | | 5-FU ($\mu$g/ml) | | |
|---|---|---|---|---|
| Cell Line | Tissue | $IC_{20}$ | $IC_{50}$ | $IC_{80}$ |
| BxPC-3 | Pancreas | 0.01 | 0.04 | 0.69 |
| WiDr | Colon | 0.03 | 0.13 | 1.70 |
| LS174T | Colon | 0.11 | 0.30 | 2.33 |
| U251MG | Glioblastoma | 0.07 | 0.38 | 3.81 |
| U118MG | Glioblastoma | 0.24 | 1.06 | 61.49 |
| U87MG | Glioblastoma | 0.37 | 1.06 | 14.02 |
| D54MG | Glioblastoma | 0.33 | 1.10 | 8.53 |
| AsPC-1 | Pancreas | 0.04 | 1.58 | 39.4 |

Further characterization of the in vitro 5-FU toxicity to human cell lines derived from gliomas (D54MG, U118MG, U251MG, U87MG), prostate (DU145, LNCaP, PC-3), colon (LS174T, WiDR), and pancreatic carcinomas (AsPC-1, BxPC-3, MiaPaca-2) confirmed that that non-gastrointestinal cells are inherently as sensitive to 5-FU as are GI cells ($IC_{50}$ 0.04–4.97 $\mu$g/ml).

EXAMPLE 31
Potential Advantages of CD/5-FC Therapy Against Gliomas

The in vitro toxicity of 5-FU to non-gastrointestinal cells suggests that direct delivery of 5-FU to the tumor cells by means of an enzyme/prodrug gene therapy system might be effective for treatment of tumors in vivo. Thus, administration of replication-defective adenovirus (Ad) vectors encoding cytosine deaminase (AdCMVCD) followed by subsequent administration of 5-fluorocytosine (5-FC) may be an effective regimen against glioma cells.

Adenovirus-mediated CD/5-FC therapy offers several distinct advantages over the HSV-tk/GCV systems currently in clinical trials for the treatment of gliomas and other central nervous system tumors. These advantages include a bystander effect that does not require cell-cell contact through gap junctions (63–66), which are known to be down-regulated in gliomas (67–69). In addition, 5-FU is capable of sensitizing cells to the effects of ionizing radiation (70, 71). On the other hand, a major factor limiting 5-FU-based therapy and potentially CD/5-FC gene therapy is 5-FU resistance, which is due in part to increased 5-FU catabolism to inactive metabolites by the enzyme dihydropyrimidine dehydrogenase (DPD, 72–75).

EXAMPLE 32
Expression of Green Gluorescent Protein in in vitro Cultured Glioma Cells Following Replication Defective Adenovirus Admninistration To determine if administration of genes by replication deficient adenoviral vectors would be effective in glioma cells, delivery of green fluorescent protein to glioma cells via an adenoviral vector was examined. Tumor cells ($10^6$) were plated in 6 well plates and allowed to adhere overnight. Cells were then infected with increasing MOI of AdCMVGFP (0–500 pfu/cell) for 1 h at 37° C. Transduction efficiency was assayed by flow cytometry 24 h post infection and quantified as the MOI effecting GFP expression (above background) in x percent of cells ($MOI_x$). The results are presented in Table 3.

TABLE 3

Quantification of AdCMVGFP gene transfer to human tumor cells

| | AdCMVGFP (pfu/cell) | | |
|---|---|---|---|
| Cell line | $MOI_{20}$ | $MOI_{50}$ | $MOI_{80}$ |
| U251MG | 1.5 | 3.7 | 7.6 |
| D54MG | 6.1 | 13.0 | 41.4 |
| LS174T | 2.7 | 16.2 | 64.4 |
| WiDr | 6.1 | 26.7 | 84.9 |
| U87MG | 11.0 | 47.9 | 130.8 |
| AsPC-1 | 47.3 | 138.6 | 362.6 |
| U118MG | 36.6 | 139.3 | 367.8 |
| BxPC-3 | 34.9 | 204.7 | 649.0 |

Differential Ad transduction efficiency was not a trivial explanation, since efficiency of reporter gene transfer using an Ad-green fluorescent protein vector (AdCMVGFP) was similar in U251MG, LS174T and WiDR cells ($MOI_{50}$ 4–27, Table 3).

EXAMPLE 33
Administration of CD/5-FC to Cultured Glioma Cells by Replication Deficient Adenovirus Next, cytosine deaminase was administered to glioma cells via the replication deficient adenovirus. Glioma cells plated in T25 flasks were infected with AdCMVCD at several multiplicities of infection (MOI 0–300 pfu/cell) for 1 h at 37° C. At twenty-four hours post-infection, cells were harvested, replated at $5 \times 10^3$ cells/well in 96 well plates, and allowed to adhere overnight. Cells were then incubated continuously in the presence of increasing concentrations of 5-FC (0–200 $\mu$g/ml) and $IC_x$ values determined at day 5 as described in Table 2. The results are shown in Tables 4 and 5.

TABLE 4

Sensitivity of human glioma cells to 5-FC upon infection with AdCMVCD in vitro

| | AdCMVCD MOI | 5-FC $IC_{50}$ | |
|---|---|---|---|
| Cell Line | (pfu/cell) | $\mu$g/ml | $r^2$ |
| D54MG | 10 | — | — |
| | 30 | — | |
| | 100 | 59.9 ± 75.1 | |
| | 300 | 7.9 ± 2.9 | |
| U87MG | 10 | — | — |
| | 30 | — | |
| | 100 | 64.0 | |
| | 300 | 43.0 ± 14.4 | |
| U118MG | 10 | — | — |
| | 30 | — | |
| | 100 | 42.2 | |
| | 300 | 18.7 | |
| U251MG | 10 | 18.4 | 0.96 |
| | 30 | 13.1 ± 11.5 | (p < 0.001) |
| | 100 | 3.3 ± 1.4 | |
| | 300 | 1.0 ± 0.4 | |

TABLE 5

Sensitivity of human gastrointestinal carcinoma cells to 5-FC upon infection with AdCMVCD in vitro

| | AdCMVCD MOI | 5-FC $IC_{50}$ | |
|---|---|---|---|
| Cell Line | (pfu/cell) | $\mu$g/ml | $r^2$ |
| AsPC-1 | 10 | — | 0.14 |
| | 30 | 85.1 ± 9.5 | (p = 0.04) |

TABLE 5-continued

Sensitivity of human gastrointestinal carcinoma cells to 5-FC upon infection with AdCMVCD in vitro

| Cell Line | AdCMVCD MOI (pfu/cell) | 5-FC IC$_{50}$ μg/ml | r$^2$ |
|---|---|---|---|
| | 100 | 114.5 ± 15.8 | |
| | 300 | 58.6 ± 8.7 | |
| BxPC-3 | 10 | 18.8 ± 5.5 | 0.41 |
| | 30 | 10.2 ± 3.0 | (p < 0.001) |
| | 100 | 2.4 ± 0.5 | |
| | 300 | 1.9 ± 0.4 | |
| LS174T | 10 | 55.3 ± 8.3 | 0.80 |
| | 30 | 8.4 ± 0.9 | (p < 0.001) |
| | 100 | 4.0 ± 0.6 | |
| | 300 | 0.8 ± 0.1 | |
| WiDR | 10 | 33.4 ± 1.9 | 0.96 |
| | 30 | 7.8 ± 0.3 | (p < 0.001) |
| | 100 | 2.7 ± 0.1 | |
| | 300 | 1.4 ± 0.1 | |

U251MG cells were as susceptible as LS174T and WiDR cells to 5-FC after infection with AdCMVCD at 10, 30 and 100 MOI (Tables 4 and 5). As expected, a dose-dependent increase in CD mRNA expression with increasing AdCMVCD MOI was detected in all cell lines tested using a quantitative RT-PCR (TaqMan) assay (data not shown). The log (IC$_{50}$) of 5-FC was inversely proportional to the log (AdCMVCD MOI) for most cell lines tested (p<0.01), demonstrating a direct inverse correlation.

AdCMVCD/5-FC produced toxicity results similar to 5-FU and a strong inverse linear relationship between AdCMVCD MOI and 5-FC IC$_{50}$ (p<0.01) was found with 7 of 8 cell lines tested. These results indicate that the in vitro response of human glioma cells to 5-FU and to AdCMVCD/5-FC is similar to that of human GI tumor cells. In the samples examined, Ad transduction efficiency was highly variable, with gene transfer levels correlating directly with the level of cell surface CAR, but not αv integrin expression. These findings suggest that CAR expression may be a major limiting factor to the success of Ad-based cancer gene therapy, particularly for malignant gliomas. Since only a subset of patients may have tumors that are efficiently infected by Ad vectors upon intralesional injection, screening of patients' tumors for CAR and αv integrin expression may prove extremely useful in selecting patients who might receive maximum benefit from Ad-based gene therapy.

Taken together, these results indicate that human glioma cells are not inherently refractory to either 5-FU or to CD/5-FC, suggesting that CD/5-FC-based gene therapy may be of clinical utility for these patients.

EXAMPLE 34

In vivo Administration of CD/5-FC to Glioma Cells

Orthotopic, intracranial murine models using human glioma xenografts may closely approximate the therapeutic response clinically achievable with CD/5-FC enzyme/prodrug therapy. Since the response of human gliomas to CD/5-FC will likely be heterogeneous in the patient population, analysis of AdCMVCD/5-FC-based therapy in multiple models might give a more comprehensive assessment of its potential clinical utility. Three intracranial xenograft models of human glioma in immunodeficient mice are being explored. The models are: U87MG, D54MG, and U251MG.

U87MG and D54MG cells (5×10$^5$) were stereotactically injected into the right frontal cortex of SCID mice. Tumors were established for 5 days before intratumoral injection of AdCMVCD (10$^8$ or 10$^9$ pfu/mouse). Mice were then treated IP with 5-FC (500 mg/kg bid) on days 2–9 post infection and monitored for survival. Kaplan-Meier survival curves and median and 20% survival values were calculated by standard methods. As shown in Tables 6 and 7, intratumoral AdCMVCD plus systemic 5-FC significantly prolonged survival of SCID mice bearing intracranial U87MG or D54MG gliomas (p<0.01), compared to SCID mice treated with an irrelevant Ad vector encoding somatostatin receptor (AdSSTR2). The therapeutic effect was dose-dependent, as a significant increase in median survival was seen with 10$^9$ pfu versus 10$^8$ pfu of AdCMVD in the U87MG model (Table 8).

TABLE 6

Survival of SCID Mice Bearing Intracranial U87MG Human Gliomas Treated with Intratumoral AdCMVCD and Systemic 5-FC

| Treatment | | | Survival | |
|---|---|---|---|---|
| Virus | PFU/Mouse | Drug | Median | 20% |
| Saline | — | 5-FC | 50 | 61 |
| AdCMVCD | 10$^9$ | Saline | 51 | 55 |
| AdCMVCD | 10$^9$ | 5-FC | 67.5 | 73 |
| AdCMVSSTR | 10$^9$ | Saline | 48 | 59 |
| AdCMVSSTR | 10$^9$ | 5-FC | 55 | 61 |

TABLE 7

Survival of SCID Mice Bearing Intracranial D54MG Human Gliomas Treated with Intratumoral AdCMVCD and Systemic 5-FC

| Treatment | | | Survival | |
|---|---|---|---|---|
| Virus | PFU/Mouse | Drug | Median | 20% |
| Saline | — | 5-FC | 29 | 30 |
| AdCMVCD | 10$^9$ | Saline | 33 | 33 |
| AdCMVCD | 10$^9$ | 5-FC | 44 | 62 |
| AdCMVSSTR | 10$^9$ | Saline | 33 | 37 |
| AdCMVSSTR | 10$^9$ | 5-FC | 30 | 34 |

TABLE 8

Survival of SCID Mice Bearing Intracranial U87MG Human Gliomas Treated with Intratumoral AdCMVCD and Systemic 5-FC

| Treatment | | | Survival | |
|---|---|---|---|---|
| Virus | PFU/Mouse | Drug | Median | 20% |
| Saline | — | 5-FC | 34 | 34 |
| AdCMVCD | 10$^8$ | Saline | 39 | 41 |
| AdCMVCD | 10$^8$ | 5-FC | 42.5 | 51 |
| AdCMVCD | 10$^9$ | Saline | 34 | 41 |
| AdCMVCD | 10$^9$ | 5-FC | 62 | 91 |

These results indicate intratumoral injection of AdCMVCD significantly prolonged the survival of mice bearing established, intracranial D54MG, U251MG, and U87MG tumors following systemic 5-FC administration (p<0.01).

EXAMPLE 35

Concurrent Administration of CD/5-FC and Ionizing Radiation to Glioma Cell

This therapeutic effect of AdCMVCD/5-FC on glioma cells could be further enhanced with concurrent fractionated ionizing external beam radiation (Table 9). U87MG cells (5×10$^5$) were stereotactically injected into the right frontal cortex of athymic nude mice. Tumors were established for 5 days before intratumoral injection of AdCMVCD (10$^9$ pfu/ mouse). Mice were then treated IP with 5-FC (500 mg/kg bid) on days 2–9 post infection, irradiated with local external beam 330 cGy $^{60}$Co radiation on days 4 and 7 post-infection, and monitored for survival. Kaplan-Meier survival curves and median and 20% survival values were calculated by standard methods. The results are presented in Table 9. Local fractionated external beam radiation ($^{60}$Co) significantly prolonged survival of mice treated with AdCMVCD/5-FC compared to animals receiving AdCMVCD/5-FC alone (p<0.01).

TABLE 9

Survival of Nude Mice Bearing Intracranial U87MG Human Gliomas Treated with Intratumoral AdCMVCD, Systemic 5-FC, and External Beam Radiation

| Treatment | | | Survival | |
|---|---|---|---|---|
| Virus | Drug | XRT | Median | 20% |
| Saline | 5-FC | – | 28 | 55 |
| Saline | 5-FC | + | 31 | 32 |
| AdCMVCD | 5-FC | – | 31.5 | 67 |
| AdCMVCD | 5-FC | + | 52 | 80 |
| AdCMVLuc | 5-FC | – | 27.5 | 39 |
| AdCMVLuc | 5-FC | + | 56 | 58 |

EXAMPLE 36
CD/5-FC with Selectively Replicating Adenovirus

One factor limiting the potential clinical efficacy of Ad-based CD/5-FC therapy is the poor tumor penetration of replication-defective Ad vectors. Intratumoral injection of such vectors is limited to cells adjacent to the needle track. Replication-competent Ad vectors may potentially overcome this limitation by selectively replicating in tumors cells, significantly increasing the level of transgene expression in infected cells as compared to non-replicative Ad while also exerting a direct oncolytic effect. Thus, it was hypothesized that a similar virus capable of selectively replicating only in tumor cells might further enhance the therapeutic response seen with replication-incompetent AdCMVCD/5-FC.

An adenoviral vector (AdE1ACD) was constructed by homologous recombination between the AdE1A-tk adenoviral vector (88) and a linearized plasmid containing the *E. coli* CD gene into which the adenoviral E1A region had been cloned. This resulted in a n adenoviral vector (AdE1ACD) which encodes both CD and a functional E1A gene but lacks the entire E1B region. Deletion of E1B gene permits the selective replication of Ad in cells harboring lesions in the p53 pathway. Replicative virus was generated by infecting 293 cells with 1 MOI of ADE1ACD for two hours. After 48 hours, the cells were harvested. The cells were resuspended at 5×10$^6$ cells/ml in media containing 2% heat inactivated fetal bovine serum and were lysed by freezing and thawing or by sonication.

Figure 15:
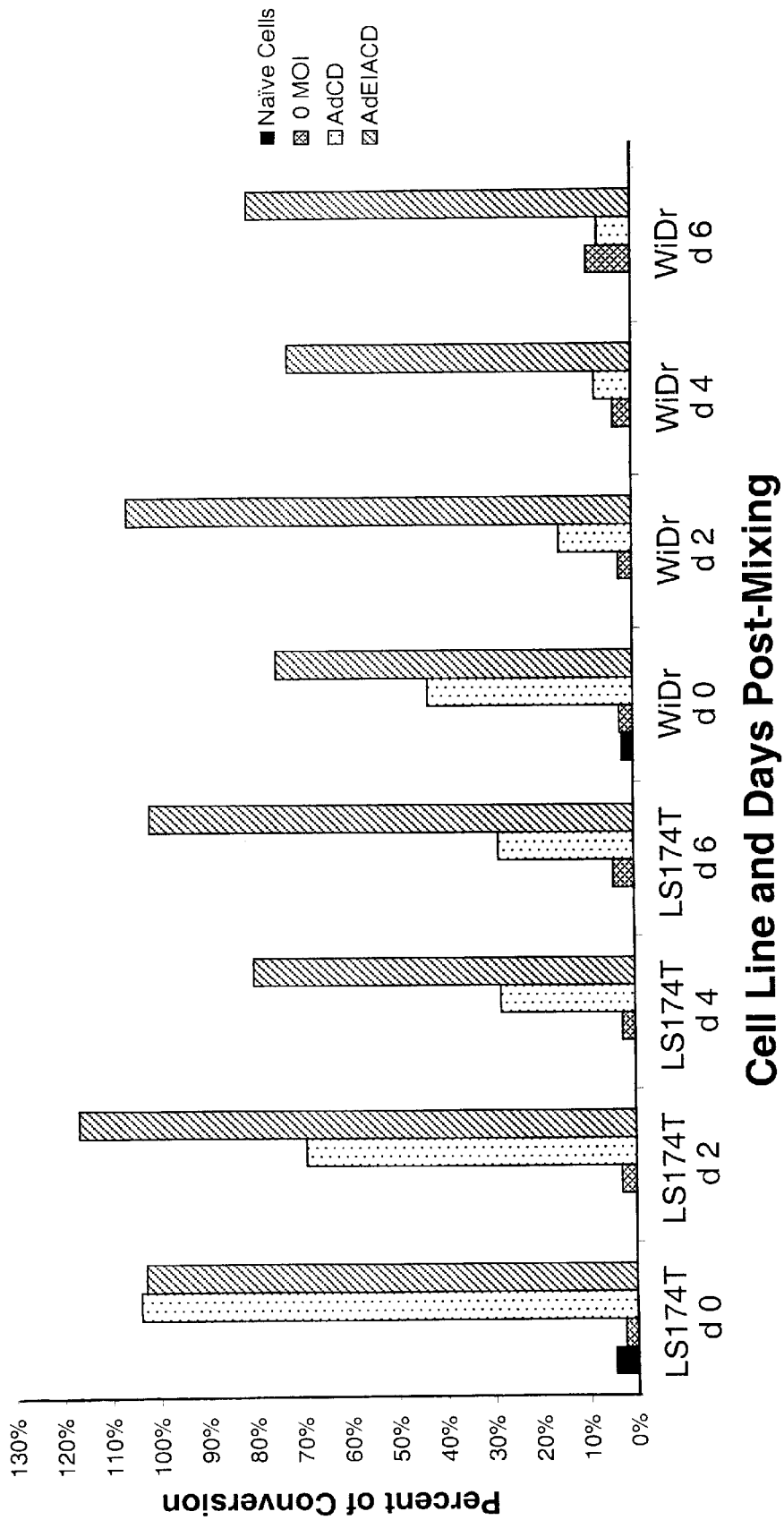
FIG. 15 shows the results of a mixing experiment in which the conversion of 5-FC to 5-FU was assayed at various time points after mixing of AdE1ACD-infected and uninfected LS174T and WiDr human colon cancer cells.

To demonstrate that infection with the selectively replicating virus augments the conversion of 5-FC to 5-FU in infected cells, a "mixing experiment" was performed. LS174T and WiDr human colon cancer cells were infected with AdCD or AdE1ACD for two hours and were harvested after 48 hours of additional incubation. The infected cells were mixed with uninfected cells at ratio of 25% infected cells per total cells. After 2, 4, and 6 days of further incubations, the cells were harvested and assayed for the ability to convert 5-FC to 5-FU. The results are presented in FIG. 15. While the conversion of 5-FC to 5-FU decreases with time after mixing with nonreplicative AdCD-infected cells, the conversion of 5-FC to 5-FU remains constant with time after mixing with the AdE1ACD infected cells as a result of increased CD production from newly infected cells.

Figure 16:
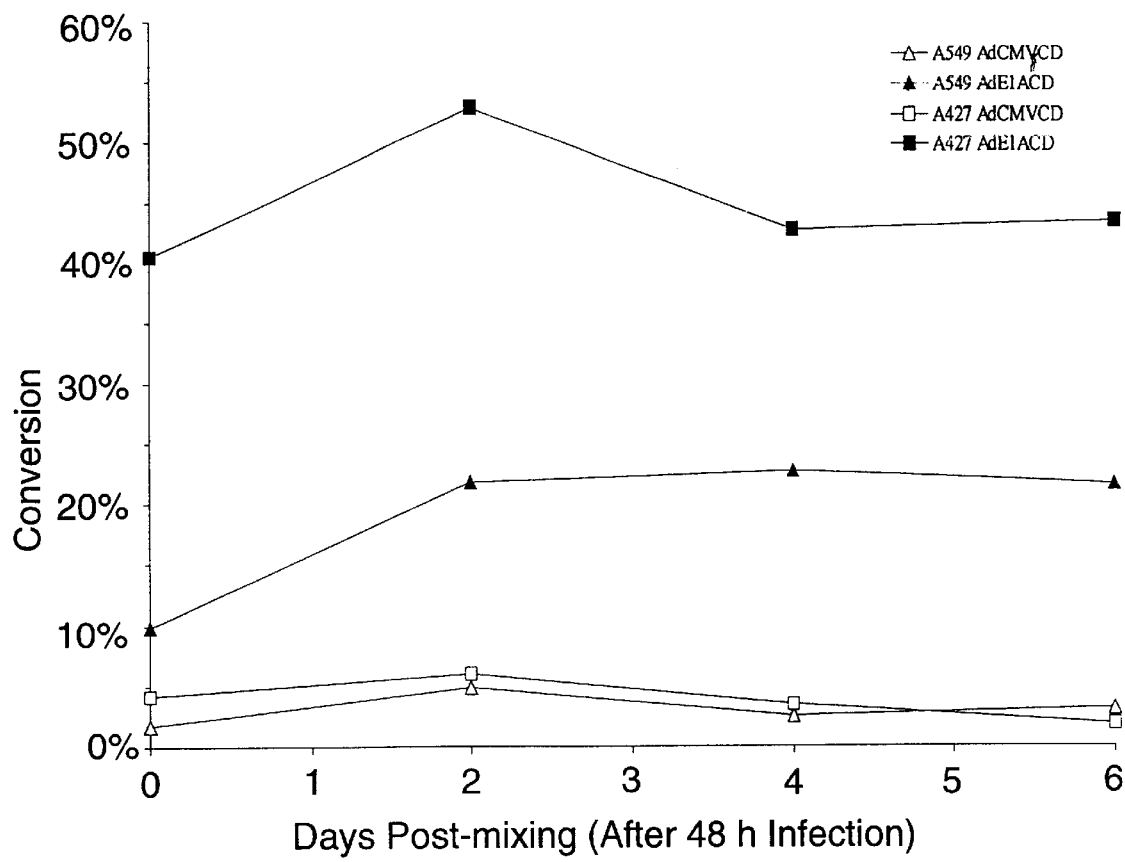
FIG. 16 shows a timecourse of CD activity in A549 and A427 cells infected with AdCMVCD or AdE1ACD (MOI 10 pfu/cell). Cells were infected for 48 h then harvested and mixed 25:75 with uninfected cells (Day 0). On the indicated day post-mixing, cells were lysed and assayed for CD activity using ($^3$H)5-FC.

Various tumor cell types were infected for 48 h with AdE1ACD at MOI 1. The cells were harvested and resuspended at 5×10$^6$ cells/ml. Lysates (4×freeze/thaw) were prepared and titered on 293 cells. While no virus could be recovered from cells infected with AdCMVCD, selectively replicating AdE1ACD efficiently replicates to high titer (10$^7$–10$^9$ pfu/ml) in human GI, prostate and lung tumor cell lines (Table 10). AdE1ACD also expresses functional CD enzyme, as determined by 5-FC to 5-FU conversion assays (FIG. 16), and increased CD protein upon intratumoral injection of nude mice bearing subcutaneous LS174T human colon carcinoma xenografts, as determined by CD immunohistochemistry. Thus, intratumoral spread of AdE1ACD may increase CD transgene expression.

TABLE 10

AdE1ACD Replication in Human Tumor Cell Lines

| Cell Line | Tissue | Titer (Log pfu/ml) |
|---|---|---|
| LS174T | Colon | 9.5 |
| WiDR | Colon | 7.6 |
| BxPC-3 | Pancreas | 6.4 |
| AsPC-1 | Pancreas | 7.4 |
| DU145 | Prostate | 6.0 |
| PC-3 | Prostate | 7.5 |

EXAMPLE 37
Survival of SCID Mice Hearing Intracranial U87MG Human Gliomas Treated Intratumorally with Selectively Replicating AdE1ACD and Systemic 5-FC U87MG cells (5×10$^5$), the stringent glioma model, were stereotactically injected into the right frontal cortex of SCID mice. Tumors were established for 5 days before intratumoral injection of AdE1ACD or AdCMVCD (10$^8$ or 10$^9$ pfu/mouse). Mice were then treated IP with 5-FC (500 mg/kg bid) on days 2–9 post infection and monitored for survival. Kaplan-Meier survival curves and median and 20% survival values were calculated by standard methods. The results are presented in Table 11. Intratumoral administration of 10$^6$ pfu of AdE1ACD and systemic 5-FC significantly prolonged the median survival of tumor-bearing animals compared to animals receiving AdE1ACD without systemic 5-FC (p<0.01, Table 11). The therapeutic effect of AdE1ACD/5-FC was critically dependent upon systemic 5-FC with surprisingly minimal anti-tumor response directly attributable to viral oncolysis.

TABLE 11

Survival of SCID Mice Bearing Intracranial U87MG Human Gliomas Treated Intratumorally with Conditionally-replicative AdE1ACD and Systemic 5-FC

| Treatment | | | Survival | |
|---|---|---|---|---|
| Virus | PFU/Mouse | Drug | Median | 20% |
| Saline | — | 5-FC | 57 | 60 |
| AdE1ACD | 10$^6$ | Saline | 49 | 54 |
| AdE1ACD | 10$^6$ | 5-FC | 84 | 86 |

Figure 17:
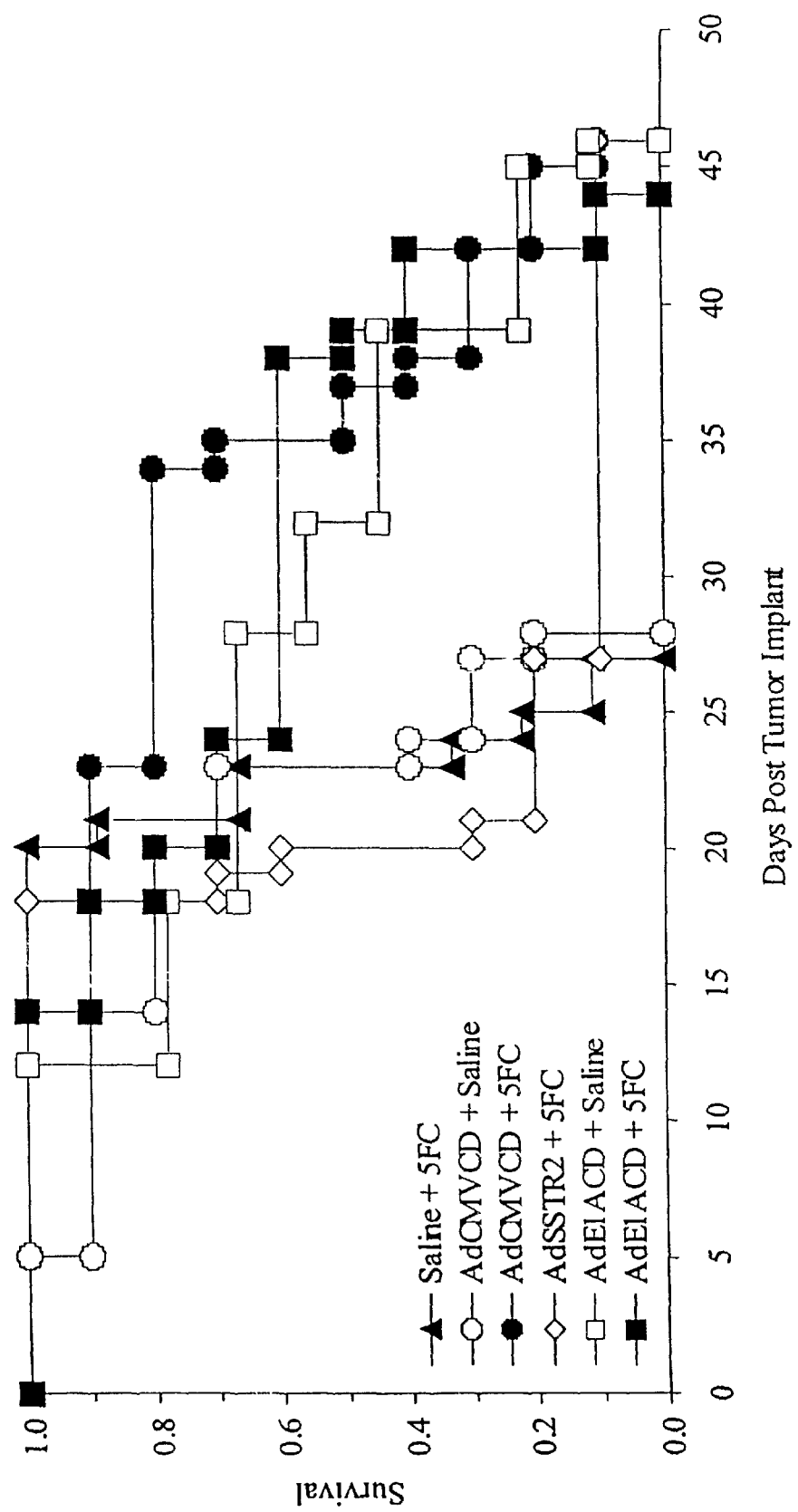
FIG. 17 shows intracranial Ad-mediated CD/systemic 5-FC therapy of mice bearing U251MG human glioma xenografts. Tumors (5.0×10$^5$ cells/mouse) were established in the right frontal cerebral hemisphere of SCID mice (9–11 mice/group) and allowed to grow for 5 days. Tumors were then directly injected with 10 μl saline, AdCMVCD or control virus AdSSTR2 (10$^9$ pfu), or AdE1ACD (10$^7$ pfu). Two days post-infection, mice were treated ip with saline or 500 mg/kg 5-FC b.i.d. for 7 days and subsequently monitored for survival.

Additional experiments were performed on intracranial tumors derived from all three glioma models. SCID mice bearing intracranial U251MG gliomas that were treated with AdE1ACD/5-FC had a significant survival advantage (median 39 days) over animals receiving replication-defective AdCMVCD/5-FC (36 days), AdE1ACD/saline (32 days), or no virus/5-FC (23 days, p<0.01; FIG. 17 and Table 12). Similar results were obtained with SCID mice bearing intracranial U87MG gliomas (AdE1ACD/5-FC 84 days, AdE1ACD/saline 49 days, no virus/5-FC 57 days, p<0.01; Table 11 and Table 12). Taken together, these results demonstrate the superior efficacy of the selectively replication-competent AdE1ACD for CD/5-FC therapy.

TABLE 12

Intratumoral Ad-mediated CD/systemic 5-FC therapy in three intracranial SCID mouse models of human glioma

| Tumor | AdCMVCD/5-FC[a] | | AdE1ACD | AdE1ACD |
|---|---|---|---|---|
| | Expt 1 | Expt 2 | Saline[b] | 5-FC[b] |
| U87MG | 1.13 | 1.35 | 0.86 | 1.47 |
| D54MG | 1.52 | 2.47 | ND | ND |
| U251MG | 1.57 | ND | 1.39 | 1.70 |

[a]Relative increase in median survival of animals receiving AdCMVCD ($10^9$ pfu) and systemic 5-FC (500 mg/kg bid ip for 7 days) versus animals receiving no virus plus 5-FC. Animals receiving AdCMVCD/saline displayed no survival advantage (data not shown).
[b]Relative increase in median survival of mice receiving AdE1ACD ($10^7$ pfu) and either saline or systemic 5-FC (500 mg/kg bid ip for 7 days) versus animals receiving no virus plus 5-FC.

While the therapeutic response of these tumors was variable (U251MG>D54MG>U87MG), the response correlated well with the in vitro sensitivity of these cells to 5-FU and to AdCMVCD/5-FC.

EXAMPLE 38
Replication Defective Adenovirus Expressing a Cytosine Deaminase (CD)/Uracil Phosihoribosyltransferase (UPRT) Fusion Protein Another factor that may limit CD/5-FC efficacy is the intratumoral expression of dihydropyrimidine dehydrogenase (DPD), the rate-limiting enzyme in 5-FU catabolism. DPD activity in peripheral blood mononuclear cells and hepatocytes significantly affects 5-FU pharmacokinetics after systemic administration, catabolizing over 90% of the injected dose to inactive metabolites. The remaining 10% of 5-FU is the active fraction that reaches GI tumors, which express low levels of DPD. However, cell lines derived from non-GI tumors (gliomas) express high levels of DPD mRNA. To overcome this potential limitation, a replication-defective Ad vector was constructed encoding a fusion protein between CD and an additional enzyme, uracil phosphoribosyltransferase (UPRT, AdCDUPRT). UPRT catalyzes the first step in 5-FU anabolism, the production of 5-fluoruridine monophosphate (5-FUMP). It was hypothesized that simultaneous expression of CD and UPRT may overcome intratumoral DPD expression by shunting CD-produced 5-FU away from the DPD-dependent catabolic pathway and into the UPRT-mediated anabolic pathway.

To test this hypothesis, 5-FC toxicity ($IC_{50}$) was compared in cells infected with AdCMVCD versus AdCDUPRT. Results with human DPD-positive glioma cells, and with prostate cancer cells, demonstrated an 18–280 fold decrease in 5-FC $IC_{50}$ with AdCDUPRT-infected versus AdCMVCD-infected cells at an equal multiplicity of infection (MOI 100 pfu/cell; Table 13). Potentiation of 5-FC toxicity by CDUPRT was due to UPRT, since expression of CDUPRT, but not CD, could increase the toxicity of glioma cells to 5-FU (571–1125 fold decrease in 5-FU $IC_{50}$ at MOI of 100 pfu/cell; Table 14). These results demonstrate the potential of UPRT to increase CD/5-FC toxicity in vitro. Taken together, these results show that selective sensitization of tumors by direct intratumoral gene transfer of a prodrug-activating enzyme may hold promise as a means to improve the therapeutic index of standard chemotherapeutic drugs.

TABLE 13

AdCMVCD and AdCDUPRT 5-FC toxicity

| | | | 5-FC $IC_{50}$ (µg/ml) | | |
|---|---|---|---|---|---|
| Cell Line | Tissue | MOI | AdCMVCD | AdCDUPRT | Enhancement |
| D54MG | Glioma | 10 | 37.8 | 0.31 | 122 |
| | | 30 | 19.6 | 0.17 | 115 |
| | | 100 | 9.1 | 0.06 | 152 |
| | | 300 | 4.7 | 0.02 | 235 |
| U251MG | Glioma | 10 | 9.9 | 0.04 | 248 |
| | | 30 | 9.1 | ND | |
| | | 100 | 2.8 | 0.01 | 280 |
| | | 300 | ND | ND | |
| U87MG | Glioma | 10 | >200 | 17.71 | |
| | | 30 | >200 | 0.88 | |
| | | 100 | 95.9 | 1.18 | 81 |
| | | 300 | 33.0 | 0.92 | 36 |
| DU145 | Prostate | 10 | >200 | 21.38 | |
| | | 30 | ND | 13.00 | |
| | | 100 | 25.0 | 0.62 | 42 |
| | | 300 | ND | 0.28 | |
| LNCaP | Prostate | 10 | 4.6 | 0.021 | 219 |
| | | 30 | ND | ND | |
| | | 100 | 1.0 | 0.007 | 143 |
| | | 300 | ND | 0.0001 | |
| PC-3 | Prostate | 10 | 26.6 | 1.26 | 21 |
| | | 30 | ND | 1.54 | |
| | | 100 | 4.2 | 0.23 | 18 |
| | | 300 | 4.6 | 0.07 | 67 |

Mean 5-FC $IC_{50}$ obtained from 2–5 separate experiments. Cells infected with AdCMVCD or AdCDUPRT at the indicated MOI (pfu/cell) for 1 h at 37° C. 5-FC toxicity determined by MTS assay 5 days after drug addition. ND, not determined.

TABLE 14

AdCDUPRT Enhancement of 5-FU toxicity

| | | 5-FU $IC_{50}$ (µg/ml) | | |
|---|---|---|---|---|
| Cell Line | MOI | AdCMVCD | AdCDUPRT | Enhancement |
| D54MG | 0 | 1.3 | | |
| | 10 | | 0.0023 | |
| | 30 | | 0.0016 | |
| | 100 | 0.9 | 0.0010 | 900 |
| | 300 | | 0.0006 | |
| U251MG | 0 | 0.4 | | |
| | 10 | | 0.0016 | |
| | 30 | | 0.0015 | |
| | 100 | 0.4 | 0.0007 | 571 |
| | 300 | | 0.0015 | |
| U87MG | 0 | 1.8 | | |
| | 10 | | 0.0081 | |
| | 30 | | 0.0025 | |
| | 100 | 2.7 | 0.0024 | 1125 |
| | 300 | | 0.0007 | |

Cells infected with AdCMVCD or AdCDUPRT at the indicated MOI (pfu/cell) for 1 h at 37° C. 5-FC toxicity ($IC_{50}$) determined by MTS assay 5 days after drug addition.

EXAMPLE 39
In vitro Quantification of Ad Gene Transfer Efficiency and CAR and αv Integrin Expression Indirect immunocytofluorimetry assays are developed for quantification of Ad gene transfer efficiency in vitro and for analysis of CAR and αv integrin expression in cultured primary pediatric brain tumors. Short-term primary cultures of pediatric brain tumors are established (81) from surgically excised tumor specimens obtained from patients at University of Alabama Hospital. Ad gene transfer efficiency is quantified as described and statistical comparisons of the MOI necessary to achieve 50% transfection ($MOI_{50}$) are made. Cell surface expression of CAR, αvβ3, and αvβ5 integrin proteins are determined by indirect immunofluorescence using RmcB (ATCC), LM609 (Chemicon, Temecula Calif.) and P1F6 (Chemicon), respectively. U118MG (CAR−) and human CAR (hCAR)-transfected U118MG (CAR+) cells serve as controls.

EXAMPLE 40
CAR Staining of Frozen and Paraffin-Embedded Tissue Sections

CAR expression in pediatric gliomas likely dictates the clinical success of Ad-based gene therapy. A facile immunohistochemical method to determine CAR expression on histological samples is devised. Various methods are explored to detect CAR on both fresh-frozen and fixed, paraffin embedded sections of freshly excised tumors using the RmcB monoclonal antibody. RmcB binds specifically to CAR by immunoblot, immunoprecipitation and flow cytometry assays, but no data exists on either its use in immunohistochemistry or on the effects of tissue processing on the RmcB epitope of CAR. These effects are explored by processing the following cell lines into standard paraffin-embedded histological sections using HistoGel (Lab Storage Systems, Warrenton, Mo.): CHO and a CHO clone stably expressing human CAR (CHO-hCAR, AQ17) and U118MG and U118MG-hCAR, which has already been constructed and shown to express high levels of CAR by RmcB flow cytometry. Various fixatives are tested prior to HistoGel embedding and paraffin processing of these cells to optimize RmcB staining specificity and intensity. Antigen retrieval techniques, including low and high temperature microwave processing, are explored if needed. Pediatric tumor samples are screened for CAR expression as well as expression of αvβ3 and αvβ5 integrins using either heterodimer specific antibodies (eg. LM609 and P1F6) or subunit specific antibodies (eg. αv-P3G8, β3-AB1932, β5-AB1926, Chemicon) as previously described (89). These results are useful in determining: (1) the prevalence of CAR/αv integrin expression on pediatric gliomas; (2) heterogeneity of CAR/αv integrin expression on single tumor samples; and, (3) the pattern of CAR/αv integrin expression on CNS cell types, as well as in correlating CAR/αv integrin expression with Ad gene transfer efficiency.

EXAMPLE 41
CD/5-FC-based Enzyme/Prodrug Therapy in Animal Models of Pediatric Glioma Two animal model systems are used to assess the efficacy of the CD/5-FC-based gene therapies. SCID mice are employed for studies with orthotopic, intracranial xenografts of human gliomas. These animals are monitored for survival following therapy and moribund mice are sacrificed and their brains harvested for pathological examination with routine hematoxylin/eosin staining. Due to lethality of local external beam radiation to the cranium of SCID mice, Balb/c nude mice are used for studies with concurrent radiation. Appropriate groups are included to control for any inter-model differences in survival following identical treatment protocols. Subcutaneous tumor models using athymic nude mice are utilized to monitor the kinetics of tumor volume reduction and the potential for and latency of rebound tumor growth. Results of these tumors are compared to the response of subcutaneous WiDR human colon xenografts, and potentially other GI tumors such as BxPC-3 pancreatic carcinomas, to assess the differential in response of tumors from these tissues. Immunohistochemical staining for CD and Ad hexon expression on both intracranial and subcutaneous tumors is performed to assess CD and Ad gene expression efficiency, distribution, and kinetics after intratumoral AdCMVCD injection.

EXAMPLE 42
Animal Studies Investigating Intratumoral AdCMVCD with Systemic 5-FC Therapy Further studies with AdCMVCD/5-FC and concurrent external beam radiation are being performed with all three cell lines in the intracranial and subcutaneous nude mouse models. Studies with concurrent CD/5-FC and radiation are limited to the use of replication-incompetent AdCMVCD virus.

The results with AdE1ACD in intracranial U87MG SCID mouse xenografts has prompted further exploration of the efficacy of this therapy in all three glioma models. In addition to allowing assessment of differential efficacy of this approach, results with D54MG and U87MG tumors permit evaluation of transduction efficiency on efficacy of AdE1ACD therapy, since these cell lines displayed similar 5-FU and AdCMVCD/5-FC sensitivities in vitro. To determine the extent of viral oncolysis versus 5-FU mediated cytotoxicity, an analogous replication-competent vector encoding HSV-tk is utilized (AdE1Atk) (88).

EXAMPLE 43
Determination of the Mechanism of Interaction of CD-5-FC-based Gene Therapy Combined with Conventional Treatment Modalities Clonogenic survival assays are performed in vitro, with fractionated radiation therapy as described above. These data provide the foundation for in vivo studies with these glioma lines. A series of in vitro studies is conducted with eniluracil, the inhibitor of Dihydropyrimidine dehydrogenase enzyme. DPD expression has been shown to be low in colon cell lines, and high in gliomas by microarray analysis (90, 91). By inhibiting DPD, an even greater 5-FU effect is achieved. DPD expression is quantified by TaqMan and DPD enzyme assays on cell lines (colon/pancreatic carcinomas and gliomas) as previously described (92). Importantly, a large panel of pediatric brain tumor tissues collected over the last 13 years is screened and cryopreserved in a repository. This provides clinical relevance to this inhibitory approach. The effect is assessed by in vitro toxicity of 5-FU±eniluracil with gliomas and GI lines as described above. This is followed by extensive dose-response testing by in vitro toxicity of AdCMVCD+ 5FC±eniluracil with gliomas and GI lines. These data provide a rational basis to conduct defined in vivo studies using both U87MG and U251MG intracranial models with the most efficacious combinations of AdCMVCD+5FC, with or without various doses of eniluracil. These studies are preceded by in vivo testing of eniluracil pharmacokinetics/pharmacodynamics to assess the most appropriate route and dosing parameters to achieve an effective biological effect in intracranial brain tumors.

The following references were cited herein.
1. Roth & Cristiano, *J. Natl. Cancer Inst.* 89, 21–39, 1997.
2. Rosenberg, et al., *Hum. Gene Ther.* 7, 1621–47, 1996.
3. Yang, et al., *Ann. Surg.* 224, 405–14, 1996.
4. Batra, et al., *J. Biol. Chem.* 272, 11736–43, 1997.
5. Lawrence, T. S., et al., *Semin. Radiat. Oncol.* 7, 247–334, 1997.
6. Hsue, et al., *Int. J. Radiat. Oncol. Biol. Phys.* 34, 445–450, 1996.
7. Oberfield, R. A., et al., *World J. Surg.* 12, 105–108, 1988.
8. Buchsbaum, D. J., et al., *Gene Ther.* 3, 1042–1068, 1996.
9. Weichselbaum, R. R., et al., *Cancer Res.* 54, 4266–4269, 1994.
10. Hallahan, D. E., et al., *Nature Med.* 1, 786–791, 1995.
11. Kim, J. H., et al., *Cancer Res.* 54, 6053–6056, 1994.
12. Kim, et al., *Int. J. Radiat. Oncol. Biol. Phys.* 33, 861–868, 1995.
13. Khil, M. S., et al., *Clin. Cancer Res.* 2, 53–57, 1996.
14. Pederson, L. C., et al., *Cancer Res.* 57, 4325–4332, 1997.
15. Pederson, et al., *J. Gastrointestinal Surg.* 2, 283–291 1998.
16. Gallardo, D., et al., *Cancer Res.* 56, 4891–4893, 1996.
17. Spitz, F. R., et al., *Clin. Cancer Res.* 2, 1665–1671, 1996.
18. Raben, D., et al., *Cancer Gene Ther.* 2, 330, 1995.
19. Raben, D., et al., *Gene Ther.* 3, 567–580, 1996.
20. Rogers, B. E., et al., *J. Nucl. Med.* 38, 1221–1229, 1997.
21. Rosenfeld, M. E., et al., *Clin. Cancer Res.* 3, 1187–1194, 1997.
22. Austin, E. A., et al., *Mol. Pharmacol.* 43, 380–387, 1993.
23. Hamstra, et al., *Human Gene Therapy* 10, 1993–2003, 1999.
24. Huber, B. E., et al., *Cancer Res.* 53, 4619–4626, 1993.
25. Dong, Y., et al., *Human Gene Ther.* 7, 713–720, 1996.
26. Hirschowitz, E. A., et al., *Hum. Gene Ther.* 6, 1055–1063, 1995.
27. Rogulski, K. R., et al., *Human Gene Ther.* 8, 73–85, 1997.
28. Becker, T. C., et al., *Meth. Cell Biol.* 43, 161–189, 1994.
29. Ohwada, A., et al., *Human Gene Ther.* 7, 1567–1576, 1996.
30. Saunders, K., et al., *Am. Surg.* 57, 816–820, 1991.
31. Vauthey, J.-N., et al., *Semin. Liver Dis.* 14, 109–114, 1994.
32. Denning, C., et al., *Human Gene Ther.* 8, 1825–1835, 1997.
33. Paillard, F., *Human Gene Ther.* 8, 1733–1736, 1997.
34. Sosnowski et al., *J. Biol. Chem.* 271, 33647–53, 1996.
35. Rosenfeld et al., *Clin. Cancer Res.* 1, 1571–1580, 1995.
36. Towbin et al., *PNAS* 76, 4350–4354, 1979.
37. Haack, et al., *Human Gene Therapy* 8, 1395–401, 1997.
38. Haberkorn et al., *J. Nucl. Med.* 37, 87–94, 1996.
39. Goldman, *Cancer Research* 57, 1447–1451, 1997.
40. Kievit, E., et al., *Cancer Research* 59, 1417–1421, 1999.
41. Aboagye, et al., *Cancer Research* 58, 4075–4078, 1998.
42. Kramer, et al. *J. Natl. Cancer Inst.* 70: 49–55. 1983.
43. Russell, et al., Pathology of tumours of the nervous system, 4th edition. Baltimore: Williams & Wilkins, 1977.
44. Silverberg, et al. 1986. CA Cancer J. Clin. 36: 9–25. 1986.
45. Central Brain Tumor Registry of the United States. Year 2000 standard statistical report. 1999.
46. Phuphanich, et al. J. Neurosurg. 60: 495–499. 1984.
47. Panitch, et al., Am J Dis Child. 119: 465–472. 1970.
48. Marchese, et al. Cancer. 65: 2771–2778. 1990.
49. Albright, et al., J. Neurosurg. 65: 751–755. 1986.
50. Packer, et al., Pediatr. Neurosci. 12: 272–282. 1985.
51. Packer, et al., J. Neurosurg. 70: 707–713. 1989.
52. Park, et al., J. Neurosurg. 58: 543–552. 1983.
53. Zhang, et al., Cancer Gene Ther. 6: 113–138. 1999.
54. Akli, et al., Nat. Genet. 3: 224–228. 1993.
55. Bajocchi, et al., Nat. Genet. 3: 229–234. 1993.
56. Davidson, et al., Nat. Genet. 3: 219–223. 1993.
57. Wickham, et al., Cell. 73: 309–319. 1993.
58. Bergelson, et al., Science. 275: 1320–1323. 1997.
59. Ichikawa, et al., Cancer Gene Ther. 7: 74–82. 2000.
60. Li, et al., Clin. Cancer Res. 5: 637–642. 1999.
61. Eck, et al., Hum. Gene Ther. 7: 1465–1482. 1996.
62. Springer, et al., J. Clin. Invest. 105: 1161–1167. 2000.
63. Lawrence, et al., Cancer Res. 58: 2588–2593. 1998.
64. Touraine, et al., Gene Ther. 5: 1705–1711. 1998.
65. Dilber, et al., Cancer Res. 57: 1523–1528. 1997.
66. Elshami, et al., Gene Ther. 3: 85–92. 1996.
67. Yamasaki, et al., Novartis Found Symp. 219: 241–254; discussion 254–260. 1999.
68. Huang, et al., J. Surg. Oncol. 70: 21–24. 1999.
69. Huang, et al., Cancer Res. 58: 5089–5096. 1998.
70. Rich, T. Oncology (Huntingt). 13: 131–134. 1999.
71. Lowy, et al., Oncology (Huntingt). 13: 121–130. 1999.
72. Diasio, R. Prog. Exp. Tumor Res. 36: 115–123. 1999.
73. Diasio, R. B. Oncology (Huntingt). 12: 23–27. 1998.
74. Diasio, R. Oncology (Huntingt). 13: 17–21. 1999.
75. Milano, et al., Eur. J. Cancer. 36: 37–42. 2000.
76. Kirn, D., Nat. Med. 4: 1341–1342. 1998.
77. Bischoff, et al., Science. 274: 373–376. 1996.
78. Hermiston, T. J. Clin. Invest. 105: 1169–1172. 2000.
79. Heise, et al., J. Clin. Invest. 105: 847–851. 2000.
80. Freytag, et al., Hum. Gene Ther. 9: 1323–1333. 1998.
81. Miller, et al., Cancer Res. 58: 5738–5748. 1998.
82. Aghi, et al., J. Natl. Cancer Inst. 90: 370–380. 1998.
83. Wang, et al., J. Neuropathol. Exp. Neurol. 58: 847–858. 1999.
84. Ge, et al., Int. J. Cancer. 71: 675–679. 1997.
85. Kyritsis, A. Oncology (Huntingt). 7: 93–100; discussion 103. 1993.
86. Maruo, et al., Anticancer Res. 10: 209–212. 1990.
87. Rodriguez, et al., Neurosurgery. 22: 691–693. 1988.
88. Wu, et al., Tumor Targeting. 4: 170–178. 1999.
89. Gladson, et al., J. Clin. Invest. 88: 1924–1932. 1991.
90. Ross, et al., Nat. Genet. 24: 227–235. 2000.
91. Scherf, et al., Nat. Genet. 24: 236–244. 2000.
92. Johnson, et al., Anal. Biochem. 278: 175–184. 2000.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of treating an individual having a solid tumor, wherein cells comprising said tumor are capable of infection by an adenovirus encoding a cytosine deaminase gene and a uracil phosphoribosyltransferase gene and are capable of coexpression said genes, comprising the steps of:

treating said individual with the adenovirus encoding said cytosine deaminase gene and said uracil phosphoribosyltranserase gene;

administering 5-fluorocytosine to said individual; and treating said individual with radiation.

2. The method of claim 1, wherein said tumor is selected from the group consisting of colon cancer, pancreatic cancer, prostate cancer, lung cancer, brain cancer, head and neck cancer, cholangiocarcinoma, glioma, and central nervous system cancer.

3. The method of claim 1, wherein said adenovirus is under control of a tumor specific promoter.

4. The method of claim 3, wherein said promoter is selected from the group consisting of a carcinoembryonic antigen promoter, DF3/MUC1 promoter, a prostate specific antigen promoter, surfactant protein A promoter, leukoprotease inhibitor promoter, erbB-2 promoter, midkine promoter, cyclooxygenase-2 promoter, alpha fetoprotein promoter and E2F promoter.

5. The method of claim 1, wherein said cytosine deaminase gene is *E. coli* cytosine deaminase gene.

6. The method of claim 1, wherein said 5-fluorocytosine is administered in a dosage of about 400 mg/kg twice per day.

7. The method of claim 1, wherein said radiation therapy is brachytherapy.

8. The method of claim 1, wherein said cytosine deaminase and said uracil phosphoribosyltransferase are expressed as a fusion protein.

9. The method of claim 1, wherein said adenovirus is AdCDUPRT.

10. The method of claim 1, wherein said radiation is administered as a single fraction or as multiple fractions.

11. The method of claim 10, wherein said single fraction is a daily dose of about 2 Gy to about 3 Gy administered over a 4 to 6 week period.

12. The method of claim 10, wherein said single fraction is a dose of about 2 Gy to about 10 Gy.

13. The method of claim 1, wherein said multiple fraction is a three fraction dose of 5 Gy.

14. The method of claim 10, wherein said multiple fraction is a five fraction dose of 2 Gy.

* * * * *